United States Patent
Sakamoto et al.

(10) Patent No.: US 10,934,246 B2
(45) Date of Patent: Mar. 2, 2021

(54) MIXTURE OF POLYMERIZABLE COMPOUND AND METHOD OF PRODUCING THE SAME

(71) Applicant: ZEON CORPORATION, Tokyo (JP)

(72) Inventors: Kei Sakamoto, Tokyo (JP); Kumi Okuyama, Tokyo (JP); Kanako Sanuki, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 16/744,489

(22) Filed: Jan. 16, 2020

(65) Prior Publication Data
US 2020/0148622 A1 May 14, 2020

Related U.S. Application Data

(62) Division of application No. 15/560,646, filed as application No. PCT/JP2016/060580 on Mar. 30, 2016, now Pat. No. 10,577,306.

(30) Foreign Application Priority Data

Mar. 31, 2015 (JP) .............................. JP2015-072950

(51) Int. Cl.
| | |
|---|---|
| *C07C 67/58* | (2006.01) |
| *C07C 67/14* | (2006.01) |
| *C07C 69/75* | (2006.01) |
| *C07D 277/82* | (2006.01) |
| *G02B 5/30* | (2006.01) |
| *C07C 69/017* | (2006.01) |
| *C07C 67/08* | (2006.01) |

(Continued)

(52) U.S. Cl.
CPC .............. *C07C 67/58* (2013.01); *C07C 67/08* (2013.01); *C07C 67/14* (2013.01); *C07C 67/52* (2013.01); *C07C 69/017* (2013.01); *C07C 69/75* (2013.01); *C07D 277/82* (2013.01); *G02B 5/30* (2013.01); *C07C 2601/14* (2017.05); *G02B 1/08* (2013.01)

(58) Field of Classification Search
CPC ....... C07C 67/58; C07C 69/017; C07C 67/08; C07C 67/52; C07C 67/14; C07C 69/75; C07C 2601/14; G02B 5/30; G02B 1/08; C07D 277/82
See application file for complete search history.

(56) References Cited

U.S. PATENT DOCUMENTS 5,567,349 A 10/1996 Kelly et al.
6,139,771 A 10/2000 Walba et al.
(Continued)

FOREIGN PATENT DOCUMENTS

EP 3357902 A1 8/2018
JP H1068816 A 3/1998
(Continued)

OTHER PUBLICATIONS

Jun. 29, 2020, Communication pursuant to Article 94(3) EPC issued by the European Patent Office in the corresponding European Patent Application No. 16773074.6.
(Continued)

*Primary Examiner* — Andrew J. Oyer

(57) ABSTRACT

Disclosed is a mixture containing compound (I) and polymerizable compound (II) wherein compound (I) accounts for 50 mol % or more of the entire mixture and 1,4-cyclohexanedicarboxylic acid accounts for less than 5 mol % of the entire mixture; a method of producing the mixture which includes reacting in a water-immiscible organic solvent 1,4-cyclohexanedicarboxylic acid dichloride with compound (IV) in the presence of a base, and washing the obtained reaction solution with a weakly acidic buffer solution; etc. The disclosure provides mixtures useful for low-cost production of polymerizable compounds which have low melting points suitable for practical use, show superior solubility to general-purpose solvents, can be produced at low costs, and allow for provision of optical films capable of uniform polarized light conversion over a wide wavelength range, and methods of producing the mixtures.

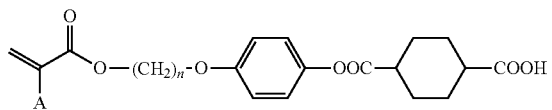

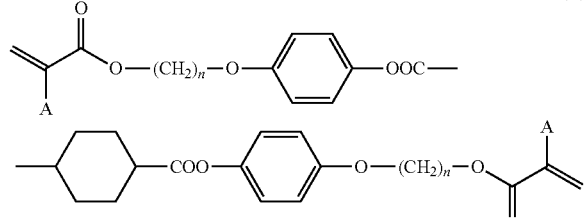

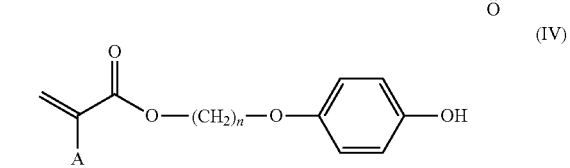

where A represents hydrogen, methyl group or chlorine, and n represents an integer of 1 to 20.

6 Claims, No Drawings

(51) Int. Cl.
  *C07C 67/52* (2006.01)
  *G02B 1/08* (2006.01)

(56) References Cited

U.S. PATENT DOCUMENTS

| | | |
|---|---|---|
| 6,203,724 B1 | 3/2001 | Reiffenrath et al. |
| 6,565,974 B1 | 5/2003 | Uchiyama et al. |
| 2002/0159005 A1 | 10/2002 | Arakawa et al. |
| 2003/0102458 A1 | 6/2003 | Nishikawa et al. |
| 2007/0176145 A1 | 8/2007 | Nishikawa et al. |
| 2007/0298191 A1 | 12/2007 | Yamahara et al. |
| 2009/0072194 A1 | 3/2009 | Yamahara et al. |
| 2009/0189120 A1 | 7/2009 | Takeuchi |
| 2010/0201920 A1 | 8/2010 | Adlem et al. |
| 2010/0301271 A1 | 12/2010 | Adlem et al. |
| 2015/0175564 A1 | 6/2015 | Sakamoto et al. |
| 2016/0200841 A1 | 7/2016 | Sakamoto |

FOREIGN PATENT DOCUMENTS

| | | |
|---|---|---|
| JP | H1090521 A | 4/1998 |
| JP | H1152131 A | 2/1999 |
| JP | 2000284126 A | 10/2000 |
| JP | 2001004837 A | 1/2001 |
| JP | 2002267838 A | 9/2002 |
| JP | 2003160540 A | 6/2003 |
| JP | 2005208414 A | 8/2005 |
| JP | 2005208415 A | 8/2005 |
| JP | 2005208416 A | 8/2005 |
| JP | 2005289980 A | 10/2005 |
| JP | 2006330710 A | 12/2006 |
| JP | 2009179563 A | 8/2009 |
| JP | 2009249526 A | 10/2009 |
| JP | 2009256327 A | 11/2009 |
| JP | 2010031223 A | 2/2010 |
| JP | 2010537954 A | 12/2010 |
| JP | 2010537955 A | 12/2010 |
| JP | 2011006360 A | 1/2011 |
| JP | 2011006361 A | 1/2011 |
| JP | 2011042606 A | 3/2011 |
| WO | 2000026705 A1 | 5/2000 |
| WO | 2006052001 A1 | 5/2006 |
| WO | 2014010325 A1 | 1/2014 |
| WO | 2015025793 A1 | 2/2015 |

OTHER PUBLICATIONS

Jun. 14, 2016, International Search Report issued in the International Patent Application No. PCT/JP2016/060580.

Oct. 16, 2018, the Extended European Search Report issued by the European Patent Office in the corresponding European Patent Application No. 16773074.6.

Oct. 21, 2019, Communication pursuant to Article 94(3) EPC issued by the European Patent Office in the corresponding European Patent Application No. 16773074.6.

Oct. 3, 2017, International Preliminary Report on Patentability issued in the International Patent Application No. PCT/JP2016/060580.

MIXTURE OF POLYMERIZABLE COMPOUND AND METHOD OF PRODUCING THE SAME

CROSS-REFERENCE TO RELATED APPLICATION

This application is a divisional application of U.S. application Ser. No. 15/560,646 filed Sep. 22, 2017, which is a National Stage Application of PCT/JP2016/060580 filed Mar. 30, 2016, which claims priority based on Japanese Patent Application No. 2015-072950 filed Mar. 31, 2015. The disclosures of the prior applications are hereby incorporated by reference herein in their entirety.

TECHNICAL FIELD

The present disclosure is directed to mixtures useful for low-cost production of polymerizable compounds which have low melting points suitable for practical use, show superior solubility to general-purpose solvents, can be produced at low costs, and allow for provision of optical films capable of uniform polarized light conversion over a wide wavelength range; and methods of producing the mixtures.

Phase difference plates include quarter-wave plates that convert linearly polarized light into circularly polarized light and half-wave plates that rotate the plane of vibration of linearly polarized light by 90 degrees. These phase difference plates can achieve exact $\lambda/4$ or $\lambda/2$ phase difference for particular monochromatic light.

However, the conventional phase difference plates have the drawback of undesirably converting the polarized light emitting from the phase difference plate into colored one. The cause of this is that the material of the phase difference plate has wavelength dispersion of phase difference and white light, or composite waves which include different rays in the visible range, shows a distribution of polarization states at different wavelengths and hence incident light cannot be converted into polarized light having its phase retarded by exactly $\lambda/4$ or $\lambda/2$ over the entire wavelength range.

To address such a drawback, studies have been made for wide-band phase difference plates which may provide uniform phase difference over a wide wavelength range, i.e., phase difference plates having so-called reverse wavelength dispersion (see, e.g., PTLS 1 to 6).

Improvements in the function of portable information terminals such as mobile PCs and cellular phones and their widespread use are increasingly requiring that flat panel display devices be thinned as much as possible. Correspondingly, it is also required to make thinner the phase difference plates which constitute the flat panel display devices.

The method of making thinner phase difference plates which is deemed most effective in recent years involves applying polymerizable compositions containing low-molecular weight polymerizable compounds on film substrates. This led to many developments of low-molecular weight polymerizable compounds that show superior wavelength dispersion or polymerizable compositions containing such low-molecular weight polymerizable compounds (see, e.g., PTLS 7 to 24).

However, the low-molecular weight compounds or compositions described in these literatures have met with many challenges in terms of performance, including inadequate reverse wavelength dispersion, difficulty in being applied in film form due to high-melting points unsuitable for processing in the industrial process, extremely narrow temperature ranges of liquid crystallinity, and low solubility to solvents commonly used in the industrial process. Moreover, since these low-molecular weight compounds or compositions are synthesized in multiple stages by employing synthesis methods that involve the use of very expensive reagents, they also have challenges in terms of costs.

CITATION LIST

Patent Literature

[PTL 1] JPH1068816A
[PTL 2] JPH1090521A
[PTL 3] JPH1152131A
[PTL 4] JP2000284126A (US20020159005A1)
[PTL 5] JP20014837A
[PTL 6] WO2000/026705A
[PTL 7] JP2002267838A
[PTL 8] JP2003160540A (US20030102458A1)
[PTL 9] JP2005208414A
[PTL 10] JP2005208415A
[PTL 11] JP2005208416A
[PTL 12] JP2005289980A (US20070176145A1)
[PTL 13] JP2006330710 (US20090072194A1)
[PTL 14] JP2009179563A (US20090189120A1)
[PTL 15] JP201031223A
[PTL 16] JP20116360A
[PTL 17] JP20116361A
[PTL 18] JP201142606A
[PTL 19] JP2010537954A (US20100201920A1)
[PTL 20] JP2010537955A (US20100301271A1)
[PTL 21] WO2006/052001 (US20070298191A1)
[PTL 22] U.S. Pat. No. 6,139,771
[PTL 23] U.S. Pat. No. 6,203,724
[PTL 24] U.S. Pat. No. 5,567,349

SUMMARY

Technical Problem

As the compound capable of solving the foregoing problem, the inventors previously proposed a polymerizable compound having the following formula (III) (hereinafter occasionally referred to as "polymerizable compound (III)") (WO2014/010325):

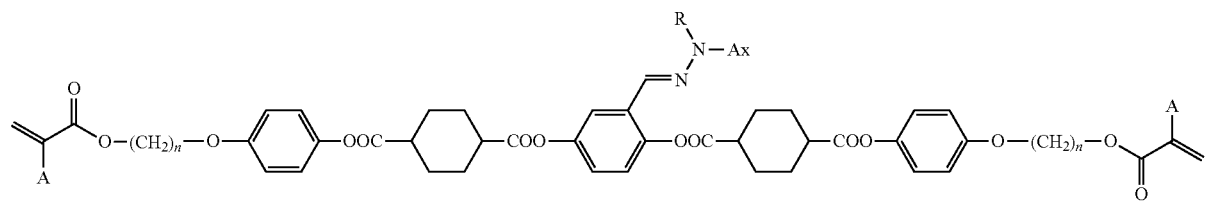

where A represents hydrogen, methyl group or chlorine, R represents hydrogen or C1-C20 organic group, Ax represents aromatic group which may have a substituent, and n represents an integer of 1 to 20.

Polymerizable compound (III) can be produced by the following process:

(1) with a carboxylic acid or carboxylic acid derivative having Formula (Ib) to afford a compound having Formula (2) (hereinafter occasionally referred to as "compound (2)"), and reacting compound (2) with a hydrazine compound having Formula (3) (hereinafter occasionally referred to as "compound (3)").

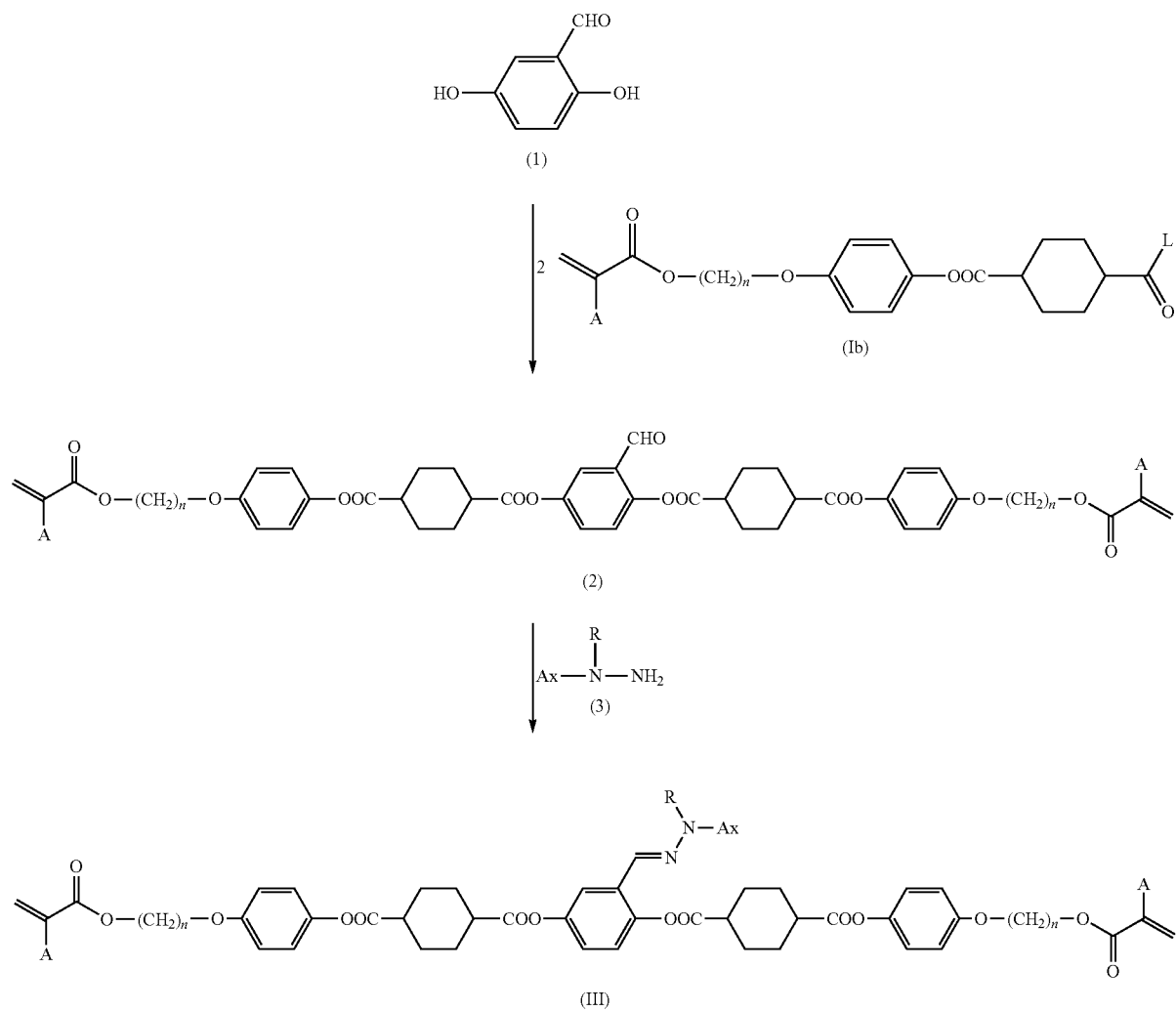

where A, R, Ax and n are as defined above and L represents a leaving group such as hydroxyl group, halogen, alkylsulfonyloxy group or aryl sulfonyl oxy group.

That is, the target polymerizable compound (III) is obtainable by reacting a benzaldehyde compound having Formula The compound having Formula (Ib) (compound where L in the formula is hydroxyl group) used in the above production method can be produced for example by the following process:

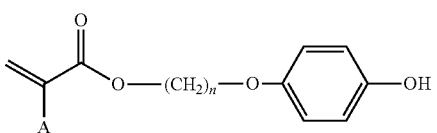

(IV)

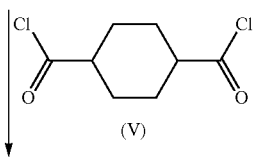

(V)

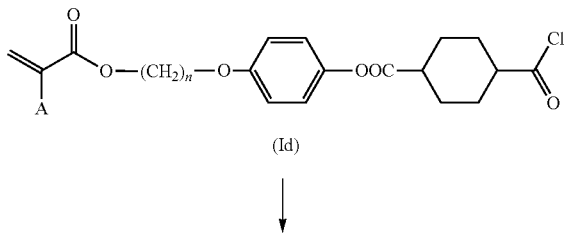

(Id)

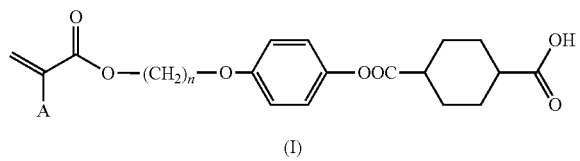

(I)

That is, the compound having Formula (I) (hereinafter occasionally referred to as "compound (I)") is obtained by reacting a compound having Formula (IV) (hereinafter occasionally referred to as "compound (IV)") with 1,4-cyclohexanedicarboxylic acid dichloride having Formula (V) to afford an acid chloride having Formula (Id), and hydrolyzing the acid chloride (or as a result of the acid chloride being hydrolyzed).

However, this production process has the drawback of producing a by-product having the following formula (II) (hereinafter occasionally referred to as "compound (II)") by the reaction of 1,4-cyclohexanedicarboxylic acid dichloride with two molecules of compound (IV).

The production of by-product compound (II) causes the raw material 1,4-cyclohexanedicarboxylic acid to remain in the reaction solution as an unreacted substance. As a result, because the carboxyl group of cyclohexane dicarboxylic acid cannot be distinguished from the carboxyl group of compound (I), the yield of the reaction in the subsequent step (reaction to obtain compound (2)) is lowered.

The present disclosure was accomplished in light of such a circumstance and it would be helpful to provide a mixture (production intermediate) useful for industrially advantageous production of polymerizable compound (III) which has a low melting point suitable for practical use, shows superior solubility to general-purpose solvents, and allows for provision of an optical film capable of uniform polarized light conversion over a wide wavelength range; and a method of producing the mixture.

Solution to Problem

Aiming to solve the foregoing problem, the inventors made extensive studies on methods of industrially advantageous production of polymerizable compound (III), and completed the present disclosure.

According to the present disclosure, there are provided mixture (1), methods (2) to (8) for producing the mixture, method (9) for producing compound (2), and methods (10) to (12) for producing polymerizable compound (III) given below:

(1) A mixture including:
compound (I) having the following Formula (I):

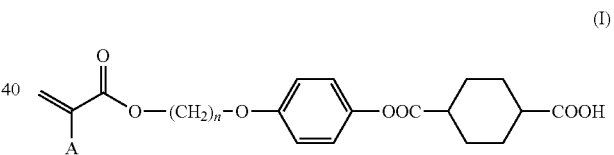

where A represents hydrogen, methyl group or chlorine, and n represents an integer of 1 to 20; and
polymerizable compound (II) having the following Formula (II):

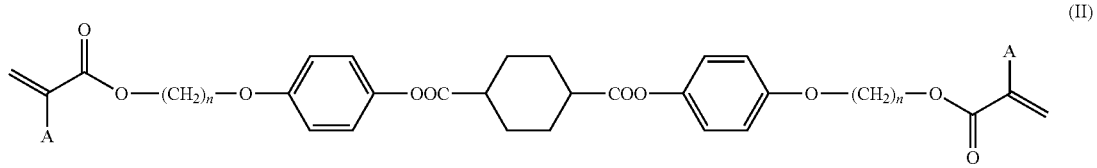

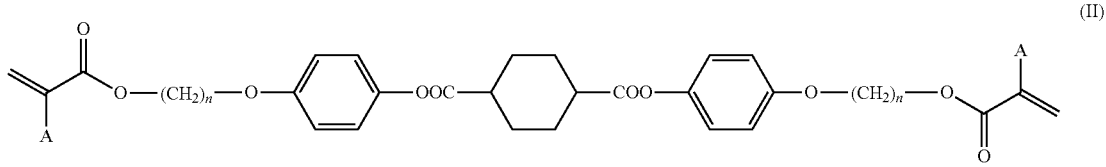

where A and n are as defined above
wherein compound (I) accounts for 50 mol % or more of the entire mixture, and 1,4-cyclohexanedicarboxylic acid as an impurity accounts for less than 5 mol % of the entire mixture.

(2) A method of removing 1,4-cyclohexanedicarboxylic acid or 1,4-cyclohexanedicarboxylic acid dichloride, including:
reacting in an organic solvent a hydroxy compound having the formula Q-OH (where Q represents an organic group which may have a substituent) with 1,4-cyclohexanedicarboxylic acid dichloride or 1,4-cyclohexanedicarboxylic acid to afford a reaction solution containing a monoester compound having the following Formula (TB):

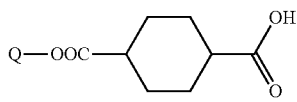

(where Q is as defined above) and 1,4-cyclohexanedicarboxylic acid dichloride or 1,4-cyclohexanedicarboxylic acid; and
washing the reaction solution with a weakly acidic buffer solution to remove 1,4-cyclohexanedicarboxylic acid or 1,4-cyclohexanedicarboxylic acid dichloride from the reaction solution.

(3) A method of producing a mixture of (1), including:
reacting in a water-immiscible organic solvent 1,4-cyclohexanedicarboxylic acid dichloride with compound (IV) having the following formula (IV):

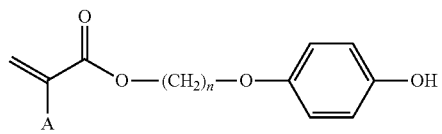

where A represents hydrogen, methyl group or chlorine, and n represents an integer of 1 to 20
in the presence of a base to afford a reaction solution; and
washing the reaction solution with a weakly acidic buffer solution.

(4) A method of producing a mixture of (1), including:
reacting in a water-immiscible organic solvent 1,4-cyclohexanedicarboxylic acid dichloride with compound (IV) having the following formula (IV):

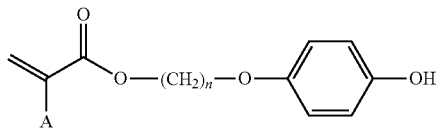

where A represents hydrogen, methyl group or chlorine, and n represents an integer of 1 to 20
in the presence of a base to afford a reaction solution;
washing the reaction solution with water; and
washing the reaction solution after washing with water with a weakly acidic buffer solution.

(5) The method of (3) or (4), wherein the buffer solution is a buffer solution having a pH of 5.0 to 6.0.

(6) The method of any one of (3) to (5), wherein the buffer solution is a mixed buffer solution of acetic acid and sodium acetate, or a mixed buffer solution of potassium hydrogen phthalate and sodium hydroxide.

(7) The method of any one of (3) to (6), wherein the water-immiscible organic solvent is an organic solvent having a Hildebrand solubility parameter of 14.0 to 22.0 (MPa$^{1/2}$).

(8) The method of any one of (3) to (7), further including, after washing with the weakly acid buffer solution, cooling an obtained organic layer to 5° C. or lower to precipitate polymerizable compound (II), and removing the precipitate.

(9) A method of producing a compound having the following Formula (2):

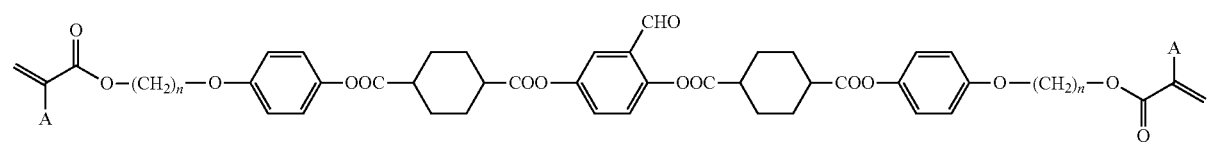

where A represents hydrogen, methyl group or chlorine, and n represents an integer of 1 to 20 the method including:

reacting in a solvent either 1) compound (I) having the following Formula (I) contained in a mixture of (1) or a mixture obtained by the method of any one of (3) to (8):

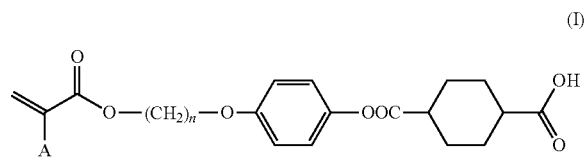

where A and n are as defined above or 2) a compound having the following Formula (IA) derived from compound (I) contained in the mixture:

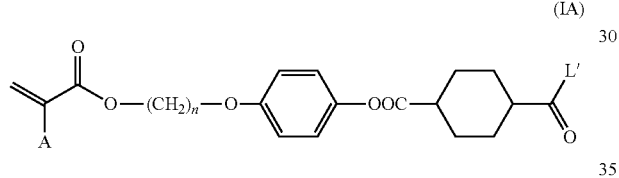

where A and n are as defined above and L' represents a leaving group other than hydroxyl group with benzaldehyde compound (1) having the following Formula (1):

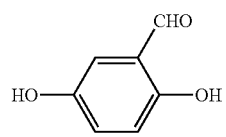

at a molar ratio of compound (I) contained in the mixture to benzaldehyde compound (1) of 1:0.3 to 1:0.5.

(10) A method of producing a polymerizable compound having the following Formula (III):

where A represents hydrogen, methyl group or chlorine, R represents hydrogen or C1-C20 organic group, Ax represents aromatic group which may have a substituent, and n represents an integer of 1 to 20 the method including:

reacting in a solvent either 1) compound (I) having the following Formula (I) contained in a mixture of (1) or a mixture obtained by the method of any one of (3) to (9):

(I)

where A and n are as defined above or 2) a compound having the following Formula (IA) derived from compound (I) contained in the mixture:

(IA)

where A and n are as defined above and L' represents a leaving group other than hydroxyl group with benzaldehyde compound (1) having the following Formula (1):

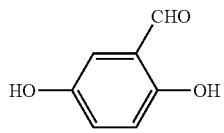

at a molar ratio of compound (I) contained in the mixture to benzaldehyde compound (1) of 1:0.3 to 1:0.5 to afford a compound having the following Formula (2):

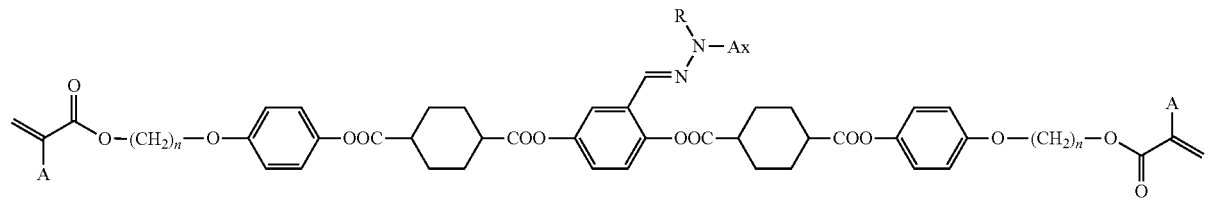

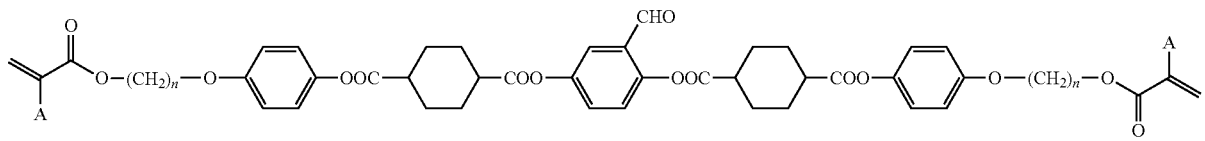

(2)

where A and n are as defined above; and
reacting the compound having Formula (2) with a hydrazine compound having the following Formula (3):

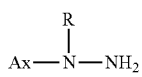

(3)

where R and Ax are as defined above.
(11) The method of (10), wherein Ax has the following Formula (4):

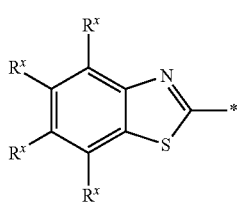

(4)

where $R^x$ each independently represents hydrogen, halogen, C1-C6 alkyl group, cyano group, nitro group, C1-C6 fluoroalkyl group, C1-C6 alkoxy group, C1-C6 alkylthio group, disubstituted amino group, or —C(=O)—O—$R^1$ where $R^1$ represents hydrogen or C1-C10 alkyl group which may have a substituent, and where each C—$R^x$ constituting the ring may be replaced by nitrogen.

The method of (10) or (11), wherein the hydrazine compound has Formula (3) where R is C1-C20 alkyl group which may have a substituent, C2-C20 alkenyl group which may have a substituent, C2-C20 alkynyl group which may have a substituent, C3-C12 cycloalkyl group which may have a substituent, or C1-C20 organic group having at least one aromatic ring selected from the group consisting of aromatic hydrocarbon ring and aromatic heterocyclic ring.

Advantageous Effect

According to the disclosed mixture, it is possible to achieve industrially advantageous (high-yield and low-cost) production of polymerizable compound (III) which has a low melting point suitable for practical use, shows superior solubility to general-purpose solvents, and allows for provision of an optical film capable of uniform polarized light conversion over a wide wavelength range.

According to the disclosed production method, it is possible to easily obtain the disclosed mixture.

DETAILED DESCRIPTION

The present disclosure will now be described in detail in the following sections: 1) Mixture, 2) Method of Removal; 3) Method of Producing Mixture; 4) Method of Producing Compound having Formula (2); and 5) Method of Producing Polymerizable Compound having Formula (III).

The phrase "may have a substituent" as used herein means "substituted or unsubstituted."

1) Mixture

The disclosed mixture comprises compounds (I) and (II) described above, wherein compound (I) accounts for 50 mol % or more of the entire mixture, and 1,4-cyclohexanedicarboxylic acid as an impurity accounts for less than 5 mol % of the entire mixture.

In Formulas (I) and (II) above, A represents hydrogen, methyl group or chlorine, preferably hydrogen or methyl group, and n represents an integer of 1 to 20, preferably an integer of 2 to 10.

In the disclosed mixture, compound (I) accounts for 50 mol % or more, preferably 58 mol % or more, more preferably 61 mol % or more, of the entire mixture.

In the disclosed mixture, 1,4-cyclohexanedicarboxylic acid accounts for less than 5 mol %, preferably less than 3 mol %, more preferably less than 1 mol %, of the entire mixture.

As described later, the disclosed mixture is particularly useful as a raw material for producing compound (2), an intermediate for producing polymerizable compound (III).

Any method can be used to produce the disclosed mixture; an exemplary method involves reacting a benzaldehyde compound having Formula (1) with 1,4-cyclohexanedicarboxylic acid dichloride having Formula (V). Among other production methods, the disclosed method of producing the mixture is preferred, which is later described.

2) Method of Removing 1,4-Cyclohexanedicarboxylic Acid or 1,4-Cyclohexanedicarboxylic Acid Dichloride The disclosed method of removal involves reacting in an organic solvent a hydroxy compound having the formula Q-OH (where Q represents an organic group which may have a substituent) with 1,4-cyclohexanedicarboxylic acid dichloride or 1,4-cyclohexanedicarboxylic acid to afford a reaction solution containing a monoester compound having the following Formula (IB):

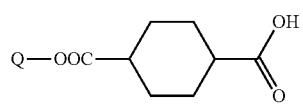

(IB)

(where Q is as defined above) and 1,4-cyclohexanedicarboxylic acid dichloride or 1,4-cyclohexanedicarboxylic acid, and washing the reaction solution with a weakly acidic buffer solution to remove 1,4-cyclohexanedicarboxylic acid or 1,4-cyclohexanedicarboxylic acid dichloride from the reaction solution.

In the formula Q-OH which represents a hydroxy compound used in the present disclosure, Q represents an organic group which may have a substituent. The organic group represented by Q is bound to a hydroxyl group via a carbon atom.

The organic group represented by Q may have any number of carbon atoms, preferably 1 to 30 carbon atoms.

Examples of organic groups include substituted or unsubstituted aliphatic group such as substituted or unsubstituted C1-C30 alkyl group, substituted or unsubstituted C2-C30 alkenyl group, substituted or unsubstituted C2-C30 alkynyl group, and substituted or unsubstituted C3-C30 cycloalkyl group; substituted or unsubstituted C6-C30 aromatic hydrocarbon group; and substituted or unsubstituted C1-C30 aromatic heterocyclic group.

The hydroxy compound having the formula Q-OH used in the present disclosure may be an alcohol compound where Q is a substituted or unsubstituted aliphatic group, or a phenol compound where Q is a substituted or unsubstituted C6-C30 aromatic hydrocarbon group or substituted or unsubstituted C1-C30 aromatic heterocyclic group. In the present disclosure, the hydroxy compound is preferably a phenol compound from the perspective of utility as, for example, an intermediate for the production of the polymerizable liquid compound, more preferably a phenol compound where Q is a substituted or unsubstituted C6-C30 aromatic hydrocarbon group, even more preferably a phenol compound where Q is a substituted or unsubstituted phenyl group, particularly preferably a compound having the following formula (IV):

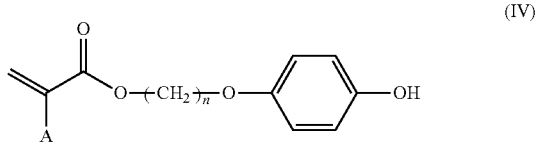

(IV)

where A represents hydrogen or methyl group, and n represents an integer of 1 to 20, preferably an integer of 1 to 12, more preferably an integer of 2 to 10.

The compound having Formula (IV) is a known substance and can be produced by methods known in the art (see, e.g., WO2014/010325A).

1,4-Cyclohexanedicarboxylic acid dichloride and 1,4-cyclohexanedicarboxylic acid used in the present disclosure may be cis or trans isomers, or may isomeric mixtures. From the perspective of the capability of obtaining a desired target compound, however, trans isomer is preferred.

1,4-Cyclohexanedicarboxylic acid dichloride, 1,4-cyclohexanedicarboxylic acid and compound (IV) can be produced by methods known in the art (see e.g., WO2014/010325). Alternatively, commercially available products can be used directly.

Examples of organic solvents used in the reactions includes ethers such as cyclopentyl methyl ether, methyl-t-butyl ether, diethyl ether, dibutyl ether, diisopropyl ether, and 1,2-dimethoxyethane; ketones such as 2-butanone and methyl isobutyl ketone; halogenated hydrocarbons such as dichloromethane, chloroform and 1,2-dichloroethane; esters such as ethyl acetate and propyl acetate; aromatic hydrocarbons such as benzene, toluene and xylene; alicyclic hydrocarbons such as cyclopentane and cyclohexane; amides such as N,N-dimethylformamide, N,N-dimethylacetamide and N-methyl-2-pyrrolidone; nitriles such as acetonitrile and propionitrile; and mixed solvents of the foregoing.

Among the organic solvents described above, when 1,4-cyclohexanedicarboxylic acid dichloride is used, it is preferred to use a water-immiscible organic solvent as a reaction solvent. The water-immiscible organic solvent refers to an organic solvent having the property of, even when mixed with water, separating two phases from each other without becoming compatible with water. The solubility of the water-immiscible organic solvent in water is 10 g (organic solvent)/100 mL (water) or less, preferably 1 g (organic solvent)/100 mL (water) or less, more preferably 0.1 g (organic solvent)/100 mL (water) or less.

Specific examples include ethers such as cyclopentyl methyl ether, methyl-t-butyl ether, diethyl ether, dibutyl ether, diisopropyl ether, 1,2-dimethoxyethane, and 2-butanone; halogenated hydrocarbons such as dichloromethane, chloroform and 1,2-dichloroethane; esters such as ethyl acetate and propyl acetate; aromatic hydrocarbons such as benzene, toluene and xylene; alicyclic hydrocarbons such as cyclopentane and cyclohexane; and mixed solvents of the foregoing.

The amount of organic solvent used is usually 1 to 1,000 ml, preferably 5 to 500 ml, per 10 g of 1,4-cyclohexanedicarboxylic acid dichloride.

In the present disclosure, reaction solutions to be subjected to washing with a weakly acidic buffer solution include, for example, the following:

(a) when 1,4-cyclohexanedicarboxylic acid dichloride is used as a substance to be reacted with the hydroxy compound having the formula Q-OH, a reaction solution which contains a monoester compound having Formula (IB), a diester compound having Formula (II), and 1,4-cyclohexanedicarboxylic acid dichloride and/or 1,4-cyclohexanedicarboxylic acid, which is obtained by reacting a hydroxy compound having the formula Q-OH (where Q represents an organic group which may have a substituent) with 1,4-cyclohexanedicarboxylic acid dichloride in an organic solvent in the presence of a base; and (b) when 1,4-cyclohexanedicarboxylic acid is used as a substance to be reacted with a hydroxy compound having the formula Q-OH, a monoester compound-containing reaction solution which contains a monoester compound having Formula (IB) and 1,4-cyclohexanedicarboxylic acid, which is obtained by reacting a hydroxy compound having the formula Q-OH (where Q represents an organic group which may have a substituent) with 1,4-cyclohexanedicarboxylic acid in an organic solvent in the presence of a dehydration condensation agent.

Examples of the base used in the case of (a) include organic bases such as triethylamine, diisopropylethylamine, phenyldimethylamine, pyridine, picoline, lutidine, and 4-(dimethylamino) pyridine; and inorganic bases such as sodium hydroxide, potassium hydroxide, magnesium hydroxide, calcium hydroxide, sodium carbonate, and potassium carbonate. These bases can be used alone or in combination.

Of these bases, preferred are organic bases from the perspective of their capability of obtaining high yield of the target product, with tertiary amines such as triethylamine and diisopropylethylamine being more preferred, and triethylamine being particularly preferred.

The base is usually used at an amount of 1 to 3 moles, preferably 1 to 2 moles, based on 1,4-cyclohexanedicarboxylic acid dichloride.

Examples of the dehydration condensation agent used in the case of (b) include N,N'-dicyclohexylcarbodiimide (DCC), N,N'-diisopropylcarbodiimide (DIC), 1-ethyl-3-(3-dimethylaminopropyl)carbodiimide (EDC), 1-ethyl-3-(3-dimethylaminopropyl)carbodiimide hydrochloride (EDC.HCl), 1H-benzotriazol-1-yloxytris(dimethylamino)

phosphonium hexafluorophosphate (BOP), 1H-benzotriazol-1-yl oxytripyrrolidinophosphonium hexafluorophosphate (PyBOP), O-(benzotriazol-1-yl)-N,N,N',N-tetramethyluronium hexafluorophosphate (HBTU), O-(benzotriazol-1-yl)-N,N,N',N-tetramethyluronium tetrafluoroborate (TBTU), O-(7-azabenzotriazol-1-yl)-N,N,N',N'-tetramethyluronium hexafluorophosphate (HATU), O-(7-azabenzotriazol-1-yl)-N,N,N',N-tetramethyluronium tetrafluoroborate (TATU), and 1,1'-carbonylbis-1H-imidazole (CDI).

The dehydration condensation agent is usually used at an amount of 1 to 3 moles, preferably 1 to 1.5 moles, based on 1,4-cyclohexanedicarboxylic acid.

The reaction can be carried out for example by adding a hydroxy compound having the formula Q-OH (where Q is as defined above) into 1,4-cyclohexanedicarboxylic acid dichloride or 1,4-cyclohexanedicarboxylic acid in organic solvent solution, adding a base or dehydration condensation agent into the obtained reaction mixture, and stirring the whole mass.

Reaction temperature is usually 0° C. to 80° C., preferably 0° C. to 50° C., more preferably 0° C. to 30° C.

Reaction time is usually from several minutes to several hours, although it depends on the reaction scale or other conditions.

In the manner described above, a reaction solution containing a monoester compound can be obtained.

In either case, the obtained reaction mixture contains, in addition to the monoester compound having Formula (IB), a diester compound having the following formula (IC) as a by-product:

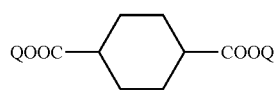

(IC)

Theoretically, the hydroxy compound having the formula Q-OH and 1,4-cyclohexanedicarboxylic acid dichloride or 1,4-cyclohexanedicarboxylic acid are used at a ratio of 1 mole of 1,4-cyclohexanedicarboxylic acid dichloride or 1,4-cyclohexanedicarboxylic acid to 1 mole of the hydroxy compound having the formula Q-OH. Thus, when the diester compound having Formula (IC) is produced as a by-product, unreacted 1,4-cyclohexanecarboxylic acid dichloride or 1,4-cyclohexanedicarboxylic acid remains in the reaction solution.

The present disclosure provides a method of removing 1,4-cyclohexanecarboxylic acid dichloride or 1,4-cyclohexanedicarboxylic acid from such a reaction solution which contains the monoester compound, 1,4-cyclohexanecarboxylic acid dichloride or 1,4-cyclohexanedicarboxylic acid, and the diester compound.

By washing the obtained reaction solution with a weakly acidic buffer solution, 1,4-cyclohexanedicarboxylic acid or 1,4-cyclohexanedicarboxylic acid dichloride can be removed from the reaction solution.

In the present disclosure the reaction solution may be washed with water (or salt water) before washing with a weakly acidic buffer solution. By washing with water, the hydrolysis reaction of cyclohexane dichloride proceeds. Alternatively, the reaction solution may be washed with a weakly acidic buffer solution after adding a water-immiscible organic solvent.

Any method can be used for washing with water (or salt water). An exemplary washing method involves adding distilled water (or salt water) to the reaction solution, stirring the mixture, and removing the aqueous layer. Stirring temperature is usually 10° C. to 60° C., preferably 20° C. to 60° C., and stirring time is usually several minutes to several hours. The washing operation may be divided into multiple steps.

Providing a step of washing the obtained reaction solution with a weakly acidic aqueous solution, preferably an aqueous solution having a pH of 5.0 to 6.0, more preferably a buffer solution having a pH of 5.0 to 6.0 reduces the amount of 1,4-cyclohexanedicarboxylic acid, a substance derived from the raw material 1,4-cyclohexanedicarboxylic acid dichloride, in the reaction solution to increase the proportion of the monoester compound in the mixture and prevent adverse effects of 1,4-cyclohexanedicarboxylic acid on the reaction in the subsequent step.

The buffer solution is an aqueous solution having a buffering action against hydrogen ion concentration, and is generally obtained by mixing a weak acid and its conjugate base, or a weak base and its conjugate acid.

Examples of buffer solutions used in the present disclosure include mixed buffer solutions of, for example, acetic acid and sodium acetate; potassium hydrogen phthalate and sodium hydroxide; potassium dihydrogen phosphate and sodium hydroxide; sodium citrate and sodium hydroxide; and potassium dihydrogen phosphate and citric acid.

Of these mixed buffer solutions, from the perspective of their capability of easily attaining the effect of the present disclosure, preferred is a mixed buffer solution of acetic acid and sodium acetate, or a mixed buffer solution of potassium hydrogen phthalate and sodium hydroxide.

The buffer solution can be prepared by methods known in the art. For example, a mixed buffer solution of acetic acid and sodium acetate having a pH of 5.6 (18° C.) can be prepared by mixing 1.9 ml of 0.2N acetic acid and 18.1 ml of 0.2M sodium acetate aqueous solution. In addition, a mixed buffer solution of potassium hydrogen phthalate and sodium hydroxide having a pH of 5.8 (20° C.) can be prepared by mixing 50 ml of 0.2M potassium hydrogen phthalate aqueous solution, 43.0 ml of 0.2N sodium hydroxide aqueous solution, and 107.0 ml of water.

Washing with buffer solution may be carried out any number of times and is usually carried out 1 to 5 times. Washing with buffer solution may be carried out after washing with water. The concentration of the buffer solution is preferably 0.1M to 2.0M, more preferably 0.5M to 1.5M.

According to the disclosed method of removing 1,4-cyclohexanedicarboxylic acid or 1,4-cyclohexanedicarboxylic acid dichloride, it is possible to simply and efficiently obtain a mixture wherein the monoester compound accounts for 50.0 mol % or more, preferably 58.0 mol % or more, more preferably 62.5 mol % or more, of the entire mixture and 1,4-cyclohexanedicarboxylic acid accounts for less than 5 mol %, preferably less than 3 mol %, more preferably less than 1 mol %, of the entire mixture.

3) Method of Producing Mixture

The disclosed method of producing mixture includes: Step 1 wherein 1,4-cyclohexanedicarboxylic acid dichloride and compound (IV) having the following formula (IV) are reacted in a water-immiscible organic solvent in the presence of a base; and Step 2 wherein the obtained reaction solution is washed with a weakly acidic buffer solution.

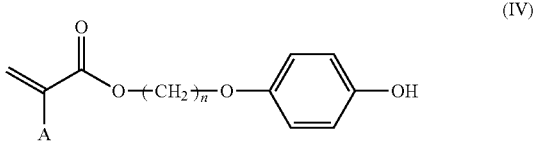

(IV)

where A and n are as defined above.

Preferably, the disclosed production method further includes, after Step 1 and prior to Step 2, Step 2a wherein the reaction solution obtained in Step 1 is washed with water.

According to the disclosed production method, it is possible to limit production of compound (II) as a by-product and thus allow for simple and efficient production of the disclosed mixture wherein compound (I) accounts for 50.0 mol % or more, preferably 58.0 mol % or more, more preferably 62.5 mol % or more, of the entire mixture and 1,4-cyclohexanedicarboxylic acid accounts for less than 5 mol %, preferably less than 3 mol %, more preferably less than 1 mol %, of the entire mixture.

[Step 1]

Step 1 is a step wherein 1,4-cyclohexanedicarboxylic acid dichloride and compound (IV) are reacted in a water-immiscible organic solvent in the presence of a base.

1,4-Cyclohexanedicarboxylic acid dichloride can be the one described as being usable in the method of removing 1,4-cyclohexanedicarboxylic acid or 1,4-cyclohexanedicarboxylic acid dichloride described above.

The water-immiscible organic solvent can be the one described as being usable in the method of removing 1,4-cyclohexanedicarboxylic acid or 1,4-cyclohexanedicarboxylic acid dichloride described above.

Preferred water-immiscible organic solvents used in the present disclosure are, in particular, organic solvents having a Hildebrand solubility parameter of preferably 14.0 to 22.0 (MPa$^{1/2}$), with organic solvents having a Hildebrand solubility parameter of 14.0 to 18.9 (MPa$^{1/2}$) being more preferred. Organic solvents having a Hildebrand solubility parameter of 14.0 to 18.0 (MPa$^{1/2}$) are particularly preferred.

The Hildebrand solubility parameter is a value (δ) introduced by Hildebrand, which provides a numerical estimate of the degree of interaction between materials, defined by regular solution theory. The use of such organic solvent makes easier the operation of the subsequent washing step and allows the target disclosed mixture to be efficiently obtained.

Preferred examples of organic solvents having a Hildebrand solubility parameter of preferably 14.0 to 22.0 (MPa$^{1/2}$) include ethers such as cyclopentyl methyl ether (Hildebrand solubility parameter (δ): 17.2 MPa$^{1/2}$), tetrahydrofuran ((δ): 18.6 MPa$^{1/2}$), methyl-t-butyl ether ((δ): 15.6 MPa$^{1/2}$), diethyl ether ((δ): 15.1 MPa$^{1/2}$), dibutyl ether ((δ): 14.9 MPa$^{1/2}$), diisopropyl ether ((δ): 14.1 MPa$^{1/2}$), 1,2-dimethoxyethane ((δ): 19.2 MPa$^{1/2}$), and 2-butanone ((δ): 19.0 MPa$^{1/2}$); halogenated hydrocarbons such as chloroform ((δ): 19.0 MPa$^{1/2}$); esters such as ethyl acetate ((δ): 18.6 MPa$^{1/2}$); aromatic hydrocarbons such as toluene ((δ): 18.2 MPa$^{1/2}$); alicyclic hydrocarbons such as cyclohexane ((δ): 16.7 MPa$^{1/2}$); and mixed solvents of the foregoing. When a mixed solvent is used, its solubility parameter can be calculated following the additivity rule.

The water-immiscible organic solvent is usually used at an amount of 1 to 1,000 ml, preferably 5 to 500 ml, per 10 g of 1,4-cyclohexanedicarboxylic acid dichloride.

The base used can be the one described as being usable in the method of removing 1,4-cyclohexanedicarboxylic acid or 1,4-cyclohexanedicarboxylic acid dichloride described above.

Of those bases, preferred are organic bases from the perspective of their capability of obtaining high yield of the target product, with tertiary amines such as triethylamine and diisopropylethylamine being more preferred, and triethylamine being particularly preferred.

The base is usually used at an amount of 1 to 3 moles, preferably 1 to 1.5 moles, based on 1,4-cyclohexanedicarboxylic acid dichloride.

1,4-Cyclohexanedicarboxylic acid dichloride and compound (IV) are usually used at a molar ratio of 1,4-cyclohexanedicarboxylic acid dichloride to compound (IV) (1,4-cyclohexanedicarboxylic acid dichloride:compound (IV)) of 1:1.1 to 2:1.

The reaction can be carried out for example by adding compound (IV) into 1,4-cyclohexanedicarboxylic acid dichloride in water-immiscible organic solvent solution, adding a base into the obtained reaction mixture, and stirring the whole mass.

Reaction temperature is usually 0° C. to 80° C., preferably 5° C. to 50° C., more preferably 5° C. to 30° C.

Reaction time is usually from several minutes to several hours, although it depends on the reaction scale or other conditions.

[Step 2a]

Step 2a is a step wherein the reaction solution obtained in Step 1 is washed with water after Step 1 and prior to Step 2. The hydrolysis reaction of the acid halide proceeds by washing with water.

Any washing method can be used. An exemplary washing method involves adding distilled water to the reaction solution obtained in Step 1, stirring the mixture, and removing the aqueous layer. Stirring temperature is usually 10° C. to 60° C., preferably 20° C. to 60° C., and stirring time is usually several minutes to several hours. The washing operation may be divided into multiple steps.

[Step 2]

Step 2 is a step wherein the reaction solution obtained in Step 1 or Step 2a is washed with a weakly acidic aqueous solution, preferably an aqueous solution having a pH of 5.0 to 6.0, more preferably a buffer solution having a pH of 5.0 to 6.0.

This step makes it possible to reduce the amount of 1,4-cyclohexanedicarboxylic acid, a substance derived from the raw material 1,4-cyclohexanedicarboxylic acid dichloride, in the mixture to increase the proportion of compound (I) in the mixture and prevent adverse effects of 1,4-cyclohexanedicarboxylic acid on the reaction in the subsequent step.

The buffer solution can be the one described as being usable in the method of removing 1,4-cyclohexanedicarboxylic acid or 1,4-cyclohexanedicarboxylic acid dichloride described above.

[Step 3]

Preferably, the disclosed method of producing a mixture further includes Step 3 wherein the organic layer obtained in Step 2 is cooled to 5° C. or lower to precipitate compound (II) and the precipitate (compound (II)) is removed. By this operation it is possible to further increase the proportion of compound (I) in the mixture.

After Step 2 (or Step 3), post-treatments commonly used in organic chemistry are performed to provide the disclosed mixture.

Specifically, poor solvent such as n-hexane is added to the obtained organic layer to precipitate crystals and the precipitated crystals are collected by filtration. The residues are then washed with poor solvent and dried to afford the disclosed mixture as a solid.

The amounts of compound (I), compound (II) and 1,4-cyclohexanedicarboxylic acid derived from the raw material in the obtained mixture can be measured using common analysis techniques, e.g., $^{13}$C-NMR spectroscopy (measurement solvent: N,N-dimethylformamide-d7), gas chromatography or high performance liquid chromatography (HPLC).

According to the disclosed method of producing a mixture, it is possible to simply and efficiently obtain a mixture wherein compound (I) accounts for 50 mol % or more of the entire mixture and 1,4-cyclohexanedicarboxylic acid accounts for less than 5 mol % of the entire mixture.

The disclosed mixture is either a mixture consisting of compounds (I) and (II) wherein compound (I) accounts for 50.0 mol % or more, preferably 58.0 mol % or more, more preferably 62.5 mol % or more, of the entire mixture [mixture (α)], or a mixture consisting of compounds (I) and (II) and 1,4-cyclohexanedicarboxylic acid wherein compound (I) accounts for 50.0 mol % or more, preferably 58.0 mol % or more, more preferably 62.5 mol % or more, of the entire mixture and 1,4-cyclohexanedicarboxylic acid accounts for less than 5 mol %, preferably less than 3 mol %, more preferably less than 1 mol %, of the entire mixture [mixture (β)].

The total amount of compounds (I) and (II) in mixture (α) is 95% by mass or more, preferably 98% by mass or more, more preferably 99% by mass or more. The total amount of compounds (I) and (II) and 1,4-cyclohexanedicarboxylic acid in mixture (13) is 95% by mass or more, preferably 98% by mass or more, more preferably 99% by mass or more.

4) Method of Producing Compound (2)

The disclosed method of producing compound (2) includes reacting either compound (I) having Formula (I) contained in the disclosed mixture or compound (IA) having Formula (IA) derived from compound (I) contained in the mixture with benzaldehyde compound (1) having Formula (1) at a molar ratio of compound (I) (in terms of compound (I) when compound (IA) is used) contained in the mixture to benzaldehyde compound (1) of 1:0.3 to 1:0.5 as follows:

Specifically, the disclosed method of producing compound (2) can be carried out in the manner described below.

(α) Method α

When compound (Ib) is a compound having Formula (Ib) where L is hydroxyl group (compound (I)), the disclosed mixture and benzaldehyde compound (1) can be reacted in suitable solvent in the presence of a dehydration condensation agent such as 1-ethyl-3-(3-dimethylaminopropyl)carbodiimide hydrochloride or dicyclohexylcarbodiimide to afford the target compound (2).

The dehydration condensation agent is usually used at an amount of 1 to 3 moles per 1 mole of benzaldehyde compound (1).

Examples of solvents used in the above reaction include chlorine solvents such as chloroform and methylene chloride; amide solvents such as N-methylpyrrolidone, N,N-dimethylformamide (DMF), N,N-dimethylacetamide, and hexamethylphosphoric acid triamide; ethers such as diethyl ether, 1,4-dioxane, cyclopentyl methyl ether, tetrahydrofuran (THF), tetrahydropyran, and 1,3-dioxolane; sulfur-containing solvents such as dimethylsulfoxide and sulfolane; aromatic hydrocarbon solvents such as benzene, toluene, and xylene; aliphatic hydrocarbon solvents such as n-pentane, n-hexane, and n-octane; alicyclic hydrocarbon solvents such as cyclopentane and cyclohexane; and mixed solvents of two or more of these solvents.

The solvent can be used at any amount and the amount can be determined as appropriate in view of the types of compounds used, reaction scale and other conditions. Usually, 1 to 20 g, preferably 2 to 10 g, of solvent is used per 1 g of the disclosed mixture.

The amount of benzaldehyde compound (1) used is usually such that the molar ratio of compound (I) in the mixture to benzaldehyde compound (1) (compound (I) in the mixture:benzaldehyde compound (1)) is 1:0.3 to 1:0.5, preferably 1:040 to 1:0.49.

For use, benzaldehyde compound (1) may be dissolved in an organic solvent.

Reaction temperature is usually from −20° C. to +30° C., preferably from −10° C. to +20° C. Reaction time is from

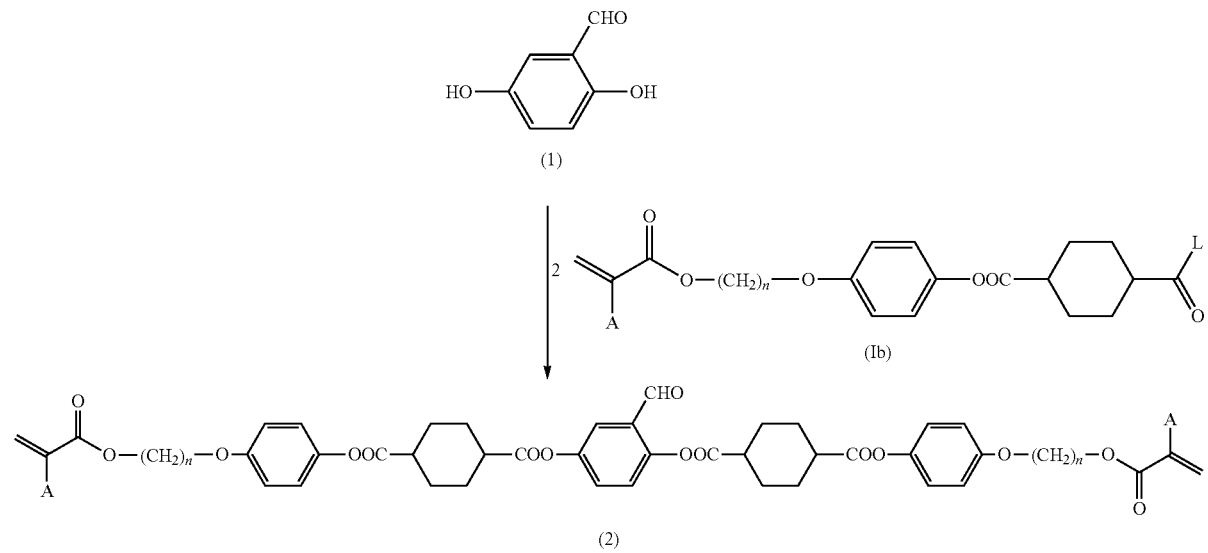

where A, n and L are as defined above.

several minutes to several hours although it depends on the reaction scale or other conditions.

(β) Method β3

When compound (Ib) is a compound having formula (Ib) where L is halogen (compound (Ic)), a halogenating agent is first allowed to act on the disclosed mixture in suitable solvent to covert compound (I) in the disclosed mixture into compound (Ic), which is then reacted with benzaldehyde compound (1) in the presence of a base to afford compound (2).

Specifically, a halogenating agent, e.g., a chlorinating agent such as thionyl chloride, sulfuryl chloride, oxalyl chloride, phosphorus trichloride or phosphorus pentachloride; or a brominating agent such as thionyl bromide is first allowed to act on the disclosed mixture to covert compound (I) in the disclosed mixture into compound (Ic), a compound having Formula (Ib) where L is halogen (Step 1).

The halogenating agent is generally used at an amount of 1 to 5 moles, preferably 1.1 to 2 moles, per 1 mole of compound (I) in the disclosed mixture.

In this case, as an activator, N,N-dimethylformamide (DMF), N,N-dimethylacetamide, or quaternary ammonium salt such as benzyltrimethylammonium chloride, benzyltriethylammonium chloride, tri(n-octyl)methylammonium chloride or trioctylmethylammonium chloride mixture may be added.

Examples of solvents used in the above reaction are those exemplified for "(α) Method α" above. The amount of solvent is also the same as that described in "(α) Method α" above.

Reaction temperature is usually from −20° C. to +30° C., preferably from −10° C. to +20° C. Reaction time is from several minutes to several hours although it depends on the reaction scale or other conditions.

After completion of the reaction, obtained compound (Ic) may be isolated, but without performing isolation, the reaction solution subjected to repeated cycles of concentration under reduced pressure, addition of fresh solvent and re-concentration under reduced pressure to remove sulfur dioxide, hydrogen halide and unreacted halogenating agent from the reaction solution may be prepared and directly used for the subsequent reaction with benzaldehyde compound (1).

Next, compound (2) can be obtained by reacting the mixture containing compound (Ic) obtained as described above and the benzaldehyde compound (1) in suitable solvent in the presence of a base.

Examples of reaction methods include i) adding benzaldehyde compound (1) to a solvent solution of the mixture containing compound (Ic) and base and stirring the whole mass; ii) adding a base to a solvent solution of the mixture containing compound (Ic) and benzaldehyde compound (1) and stirring the whole mass; and iii) adding the mixture containing compound (Ic) to a solvent solution of benzaldehyde compound (1) and base and stirring the whole mass.

Benzaldehyde compound (1) is usually used at an amount of 0.3 to 0.5 moles, preferably 0.40 to 0.49 moles, per 1 mole of compound (I) in the disclosed mixture.

For use, benzaldehyde compound (1) may be dissolved in an organic solvent.

Examples of organic solvents used are those exemplified for "(α) Method α" above. The amount of organic solvent is also the same as that described in "(α) Method α" above.

Examples of bases used include organic bases such as triethylamine and pyridine; and inorganic bases such as sodium hydroxide, sodium carbonate, and sodium hydrogencarbonate.

The base is usually used at an amount of 1 to 3 moles per 1 mole of compound (I) in the disclosed mixture used.

Reaction temperature is usually from −20° C. to +30° C., preferably from −10° C. to +20° C. Reaction time is from several minutes to several hours although it depends on the reaction scale or other conditions.

(γ) Method γ

In the case of a compound having Formula (Ib) where L is a group represented by Q-SO$_2$—O— (where Q represents methyl group, phenyl group or 4-methylphenyl group; the same applies below) (compound (Ie)), compound (2) can be obtained in the manner described below.

First, the disclosed mixture and a sulfonyl halide having the formula Q-SO$_2$—X (where Q is as defined above and X represents halogen) are reacted in suitable solvent in the presence of a base such as triethylamine, diisopropylethylamine, pyridine or 4-(dimethylamino)pyridine to covert compound (I) in the disclosed mixture into compound (Ie).

The sulfonyl halide is usually used at an amount of 1 to 3 equivalents per 1 equivalent of compound (I) in the disclosed mixture.

The base is usually used at amount of to 1 to 3 equivalents per 1 equivalent of compound (I).

Subsequently, the reaction mixture containing compound (Ie) obtained above and benzaldehyde compound (1) are reacted in the presence of a base as in Step 2 of Method (β) to afford compound (2).

Examples of reaction methods include i) adding benzaldehyde compound (1) to a solvent solution of the mixture containing compound (Ie) and base and stirring the whole mass; ii) adding a base to a solvent solution of the mixture containing compound (Ie) and benzaldehyde compound (1) and stirring the whole mass; and iii) adding the mixture containing compound (Ie) to a solvent solution of benzaldehyde compound (1) and base and stirring the whole mass.

Benzaldehyde compound (1) can be produced by methods known in the art. Alternatively, those commercially available can be used after purification as desired.

Without isolating compound (2) thus obtained, the reaction solution can be directly used for reaction with compound (3) described below.

5) Method of Producing Polymerizable Compound (III)

The disclosed method of producing polymerizable compound (III) includes obtaining compound (2) by the disclosed method of producing compound (2) described above, and reacting compound (2) with a hydrazine compound having the following Formula (3):

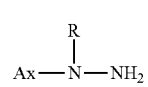

(3)

where R represents hydrogen or C1-C20 organic group and Ax represents aromatic group which may have a substituent as follows:

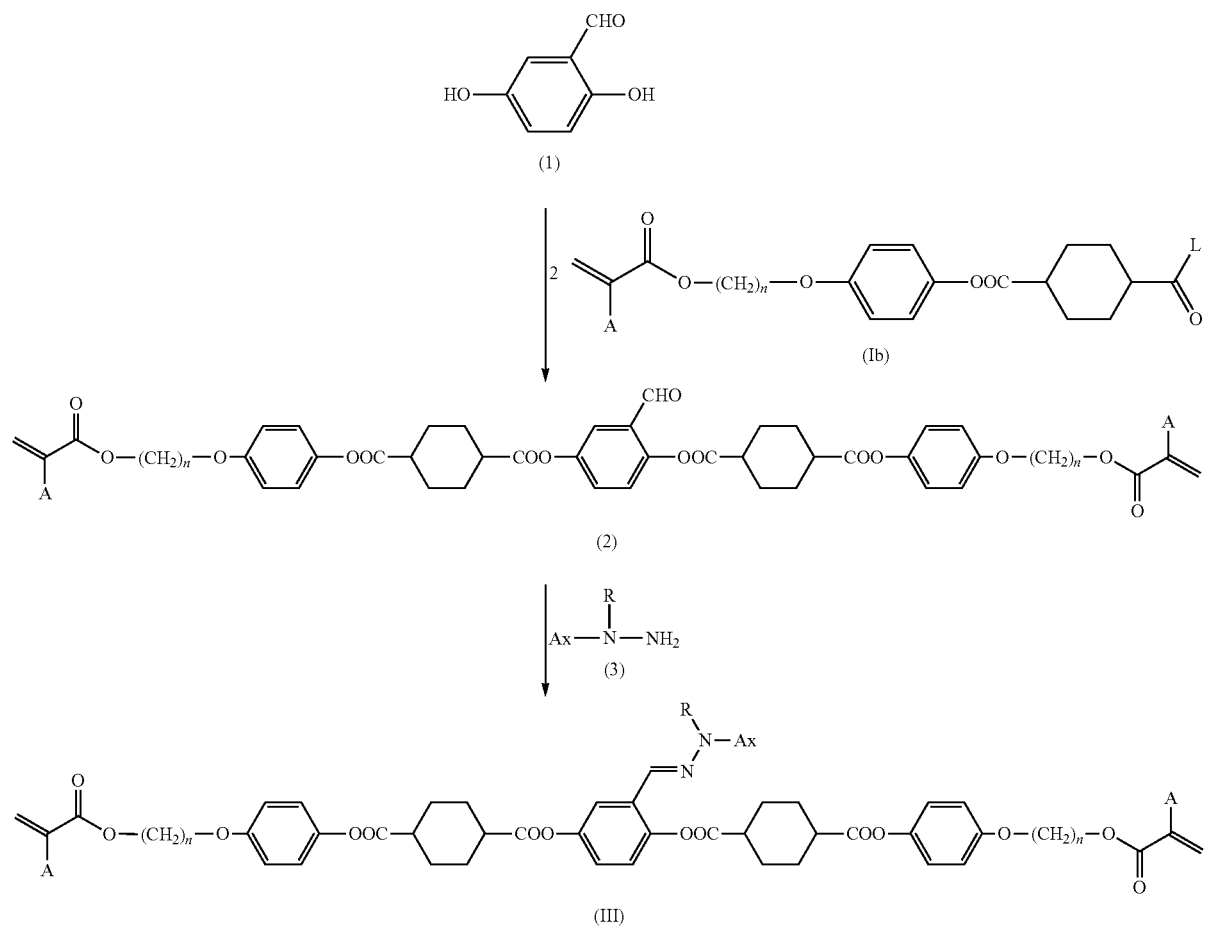

where A and n are as defined above, and R represents hydrogen or C1-C20 organic group which may have a substituent.

The C1-C20 organic group for R is not specifically limited and may be, for example, C1-C20 alkyl group which may have a substituent, C2-C20 alkenyl group which may have a substituent, C2-C20 alkynyl group which may have a substituent, C3-C12 cycloalkyl group which may have a substituent, or C2-C20 organic group having at least one aromatic ring selected from the group consisting of aromatic hydrocarbon ring and aromatic heterocyclic ring.

Of them, preferred for R are C1-C20 alkyl group which may have a substituent, C2-C20 alkenyl group which may have a substituent, C2-C20 alkynyl group which may have a substituent, and C2-C20 organic group having at least one aromatic ring selected from the group consisting of aromatic hydrocarbon ring and aromatic heterocyclic ring.

Examples of C1-C20 alkyl group of C1-C20 alkyl group which may have a substituent for R include methyl group, ethyl group, n-propyl group, isopropyl group, n-butyl group, isobutyl group, 1-methylpentyl group, 1-ethylpentyl group, sec-butyl group, t-butyl group, n-pentyl group, isopentyl group, neopentyl group, n-hexyl group, isohexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, and n-icosyl group. C1-C20 alkyl group which may have a substituent preferably has 1 to 12 carbon atoms, more preferably 4 to 10 carbon atoms.

Examples of C2-20 alkenyl group of C2-C20 alkenyl group which may have a substituent for R include vinyl group, propenyl group, isopropenyl group, butenyl group, isobutenyl group, pentenyl group, hexenyl group, heptenyl group, octenyl group, decenyl group, undecenyl group, dodecenyl group, tridecenyl group, tetradecenyl group, pentadecenyl group, hexadecenyl group, heptadecenyl group, octadecenyl group, nonadecenyl group, and icosenyl group.

C2-C20 alkenyl group preferably has 2 to 12 carbon atoms.

Examples of C2-C20 alkynyl group of C2-C20 alkynyl group which may have a substituent for R include ethynyl group, propynyl group, 2-propynyl group (propargyl group), butynyl group, 2-butynyl group, 3-butynyl group, pentynyl group, 2-pentynyl group, hexynyl group, 5-hexynyl group, heptynyl group, octynyl group, 2-octynyl group, nonanyl group, decanyl group, and 7-decanyl group.

Examples of C3-C12 cycloalkyl group of C3-C12 cycloalkyl group which may have a substituent include for R cyclopropyl group, cyclobutyl group, cyclopentyl group, cyclohexyl group, and cyclooctyl group.

Examples of substituents on C1-C20 alkyl group, C2-20 alkenyl group and C2-C20 alkynyl group for R include halogens such as fluorine and chlorine; cyano group; substituted amino group such as dimethylamino group; C1-C20 alkoxy group such as methoxy group, ethoxy group, isopropoxy group, and butoxy group; C1-C12 alkoxy group substituted with C1-12 alkoxy group, such as methoxymethoxy group and methoxyethoxy group; nitro group; aryl group such as phenyl group and naphthyl group; C3-C8 cycloalkyl group such as cyclopropyl group, cyclopentyl group, and cyclohexyl group; C3-C8 cycloalkyloxy group such as cyclopentyloxy group and cyclohexyloxy group; C2-C12 cyclic ether group such as tetrahydrofuranyl group, tetrahydropyranyl group, dioxolanyl group, and dioxanyl group; C6-C14 aryloxy group such as phenoxy group and naphthoxy group; C1-C12 fluoroalkyl group substituted with at least one fluorine atom, such as trifluoromethyl group, pentafluoroethyl group, and 2,2,2-trifluoroethyl group; benzofuryl group; benzopyranyl group; benzodioxolyl group; benzodioxanyl group; —C(=O)—$R^a$; —C(=O)—$OR^a$; —$SO_2R^b$; —SW; C1-C12 alkoxy group substituted with —SW; and hydroxyl group.

$R^a$ represents C1-C20 alkyl group, C2-20 alkenyl group, C3-C12 cycloalkyl group or C5-C12 aromatic hydrocarbon group. Examples of C1-C20 alkyl group, C2-20 alkenyl group and C3-C12 cycloalkyl group for $R^a$ are the same as those exemplified for R above. Examples of C5-C12 aromatic hydrocarbon group include phenyl group, 1-naphthyl group, and 2-naphthyl group.

$R^b$ represents C1-C20 alkyl group, C2-C20 alkenyl group, phenyl group or 4-methylphenyl group.

Examples of C1-C20 alkyl group and C2-C20 alkenyl group for $R^b$ are the same as those exemplified for R above.

Examples of substituents on C3-C12 cycloalkyl group for R include halogens such as fluorine and chlorine; cyano group; substituted amino group such as dimethylamino group; C1-C6 alkyl group such as methyl group, ethyl group and propyl group; C1-C6 alkoxy group such as methoxy group, ethoxy group, and isopropoxy group; nitro group; aryl group such as phenyl group and naphthyl group; C3-C8 cycloalkyl group such as cyclopropyl group, cyclopentyl group and cyclohexyl group; —C(=O)—$R^a$; —C(=O)—$OR^a$; —$SO_2R^b$; and hydroxyl group. $R^a$ and $R^b$ are as defined above.

The C2-C20 organic group having at least one aromatic ring selected from the group consisting of aromatic hydrocarbon ring and aromatic heterocyclic ring for R may have more than aromatic ring and may have an aromatic hydrocarbon ring and an aromatic heterocyclic ring.

Examples of the aromatic hydrocarbon ring include benzene ring, naphthalene ring, and anthracene ring. Examples of the aromatic heterocyclic ring include monocyclic aromatic heterocyclic rings such as pyrrole ring, furan ring, thiophene ring, pyridine ring, pyridazine ring, pyrimidine ring, pyrazine ring, pyrazole ring, imidazole ring, oxazole ring, and thiazole ring; and fused aromatic heterocyclic rings such as benzothiazole ring, benzoxazole ring, quinoline ring, phthalazine ring, benzimidazole ring, benzopyrazole ring, benzofuran ring, benzothiophene ring, thiazolopyridine ring, oxazolopyridine ring, thiazolopyrazine ring, oxazolopyrazine ring, thiazolopyridazine ring, oxazolopyridazine ring, thiazolopyrimidine ring, and oxazolopyrimidine ring;

The aromatic ring of R may have a substituent. Examples of such substituents include halogens such as fluorine and chlorine; cyano group; C1-C6 alkyl group such as methyl group, ethyl group and propyl group; C2-C6 alkenyl group such as vinyl group and allyl group; C1-C6 halogenated alkyl group such as trifluoromethyl group; substituted amino group such as dimethylamino group; C1-C6 alkoxy group such as methoxy group, ethoxy group, and isopropoxy group; nitro group; aryl group such as phenyl group and naphthyl group; —C(=O)—$R^c$; —C(=O)—$OR^c$; and —$SO_2R^d$.

$R^c$ represents C1-C20 alkyl group, C2-20 alkenyl group or C3-C12 cycloalkyl group. Examples of $R^c$ are the same as C1-C20 alkyl group, C2-20 alkenyl group and C3-C12 cycloalkyl group exemplified for R above.

$R^d$ represents C1-C20 alkyl group, C2-20 alkenyl group, phenyl group or 4-methylphenyl group. Examples of C1-C20 alkyl group and C2-20 alkenyl group are the same as those exemplified for R above.

The aromatic ring of R may have two or more same or different substituents, and adjacent substituents may be joined together to form a ring. The ring to be formed may be a monocyclic, fused polycyclic, unsaturated cyclic or saturated cyclic ring.

The number of carbon atoms of C2-C20 organic group for R refers to the total number of carbon atoms of the entire organic group, excluding the carbon atom(s) of the substituent(s).

Examples of C2-C20 organic group having at least one aromatic ring selected from the group consisting of aromatic hydrocarbon ring and aromatic heterocyclic ring for R include C6-C20 aromatic hydrocarbon ring group such as benzene group, naphthalene group, and anthracene group; C2-C20 aromatic heterocyclic group such as pyrrole group, furan group, thiophene group, pyridine group, pyridazine group, pyrimidine group, pyrazine group, pyrazole group, imidazole group, oxazole group, thiazole group, benzothiazole group, benzoxazole group, quinoline group, phthalazine group, benzoimidazole group, benzopyrazole group, benzofuran group, benzothiophene group, thiazolopyridine group, oxazolopyridine group, thiazolopyrazine group, oxazolopyrazine group, thiazolopyridazine group, oxazolopyridazine group, thiazolopyrimidine group, and oxazolopyrimidine group; C3-C20 alkyl group having at least one aromatic ring selected from the group consisting of aromatic hydrocarbon ring group and aromatic heterocyclic ring group; C4-C20 alkenyl group having at least one aromatic ring selected from the group consisting of aromatic hydrocarbon ring group and aromatic heterocyclic ring group; and C4-C20 alkynyl group having at least one aromatic ring selected from the group consisting of aromatic hydrocarbon ring group and aromatic heterocyclic ring group.

Ax represents an aromatic group which may have a substituent. Preferred but non-limiting specific examples of Ax are shown below. In each structural formula—represents a bond at any position on the ring, which binds with nitrogen (i.e., nitrogen which binds with Ax in Formula (V)).

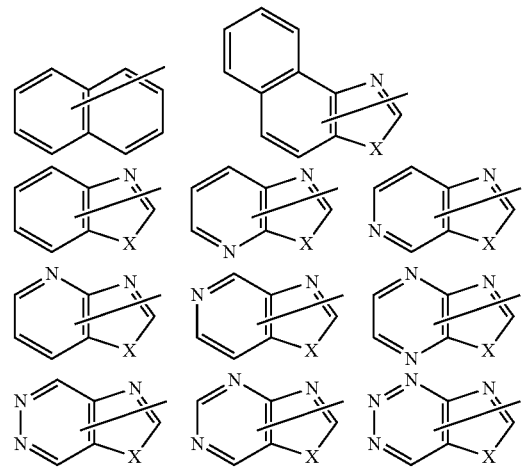

where X represents NR$^w$, oxygen, sulfur, —SO— or —SO$_2$— with the proviso that oxygen, sulfur, —SO— and —SO$_2$— are not adjacent to each other, and R$^w$ represents hydrogen or C1-C6 alkyl group such as methyl group, ethyl group or propyl group.

The rings shown above may have a substituent. Examples of such substituents include halogens such as fluorine, chlorine and bromine; C1-C6 alkyl group such as methyl group, ethyl group and propyl group; cyano group; C2-C6 alkenyl group such as vinyl group and allyl group; C1-C6 halogenated alkyl group such as trifluoromethyl group and pentafluoroethyl group; substituted amino group such as dimethylamino group; C1-C6 alkoxy group such as methoxy group, ethoxy group, and isopropoxy group; nitro group; aryl group such as phenyl group and naphthyl group; —C(=O)—R$^k$; —C(=O)—OR$^k$; and —SO$_2$R$^h$.

R$^h$ represents C1-C20 alkyl group, C2-20 alkenyl group, phenyl group or 4-methylphenyl group. R$^k$ represents hydrogen; C1-C6 alkyl group such as methyl group and ethyl group; or C6-C14 aryl group such as phenyl group.

R$^k$ preferably represents halogen, cyano group, C1-C6 alkyl group, or C1-C6 alkoxy group.

A more preferred example of Ax is the group having the following Formula (4):

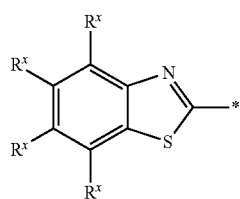

(4)

where * represents a binding point to nitrogen atom, and R$^x$ represents hydrogen; halogen such as fluorine, chlorine and bromine; C1-C6 alkyl group such as methyl group, ethyl group and propyl group; cyano group; nitro group; C1-C6 fluoroalkyl group such as trifluoromethyl group and pentafluoroethyl group; C1-C6 alkoxy group such as methoxy group, ethoxy group and isopropoxy group; C1-C6 alkylthio group such as methylthio group and ethylthio group; monosubstituted amino group such as methylamino group and ethylamino group; disubstituted amino group such as dimethylamino group and diethylamino group; or —C(=O)—O—R$^1$. R$^1$ represents hydrogen or C1-C10 alkyl group which may have a substituent.

Of them, each R$^x$ is preferably independently hydrogen, halogen, C1-C6 alkyl group, cyano group, nitro group, C1-C6 fluoroalkyl group, C1-C6 alkoxy group or —C(=O)—O—R$^1$. Particularly preferably, every R$^x$ is hydrogen.

Examples of C1-C10 alkyl group of C1-C10 alkyl group which may have a substituent for R$^1$ include methyl group, ethyl group, n-propyl group, isopropyl group, n-butyl group, isobutyl group, 1-methylpentyl group, 1-ethylpentyl group, sec-butyl group, t-butyl group, n-pentyl group, isopentyl group, neopentyl group, n-hexyl group, isohexyl group, n-heptyl group, n-octyl group, n-nonyl group, and n-decyl group. Examples of substituents on these groups are the same as those exemplified above as substituents on C1-C20 alkyl group etc. which may have a substituent for R.

Each R$^x$ may be the same or different. Any of C—R$^x$ constituting the ring may be replaced by nitrogen atom. Specific but non-limiting examples of the ring having R$^x$ in which C—R$^x$ is replaced by nitrogen atom are shown below:

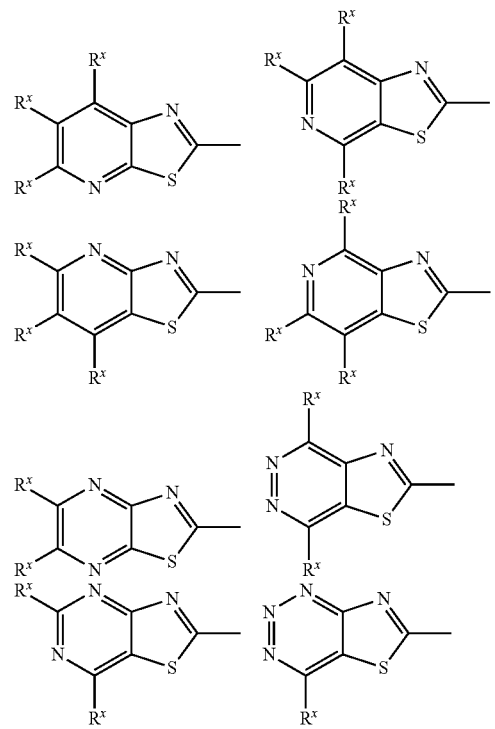

where R$^x$ is as defined above.

Of them, a ring in which every R$^x$ is hydrogen is preferred.

With regard to the reaction between compounds (2) and (3), the method of obtaining compound (3) etc., the methods described for example in PTL 25 can be employed.

Using the disclosed mixture as a production intermediate for production of polymerizable compound (III), polymerizable compound (III) can be produced at low cost and at high yield.

EXAMPLES

The present disclosure will now be described in detail with reference to Examples, which however shall not be construed as limiting the scope of the present disclosure in any way.

(Example 1) Production of Mixture 1

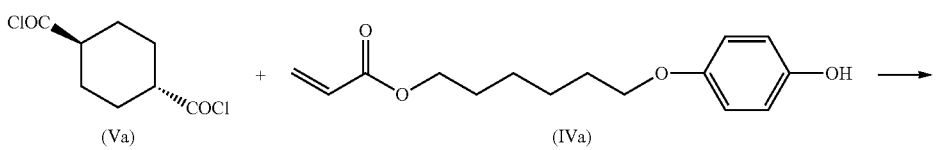

-continued

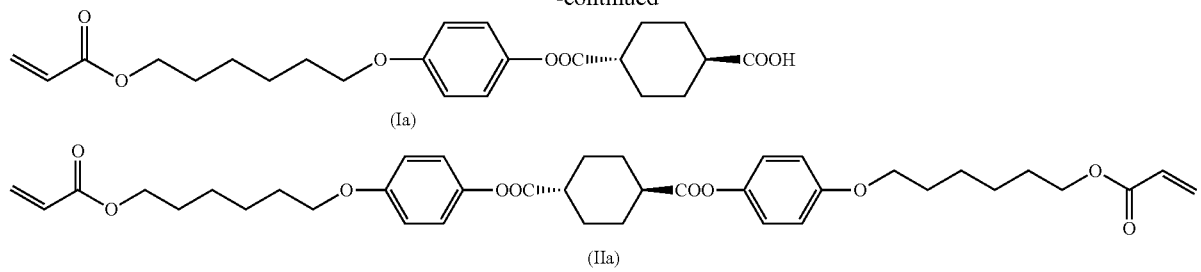

A three-necked reactor equipped with a thermometer was charged with 10.0 g (47.83 mmol) of trans-1,4-cyclohexanedicarboxylic acid dichloride having Formula (Va) and 200 ml of cyclopentyl methyl ether (CPME) under a nitrogen stream. To the reactor was added 12.64 g (47.83 mmol) of 4-(6-acryloyloxy-hex-1-yloxy)phenol (manufactured by DKSH) having Formula (IVa). The reactor was immersed in an ice bath to lower the internal temperature of the reaction solution to 0° C. 4.83 g (47.83 mmol) of triethylamine was slowly added dropwise over 5 minutes while keeping the internal temperature of the reaction solution at 10° C. or below. After completion of the dropwise addition, the temperature of the whole mass was raised back to 25° C. and stirring was further performed for 1 hour.

To the obtained reaction solution was added 100 ml of distilled water and after washing at 25° C. for 2 hours, the aqueous layer was withdrawn. The organic layer was further washed twice with 250 ml of a 0.5 mol/L buffer solution (pH 5.7) consisting of potassium hydrogen phthalate and sodium hydroxide, and then the buffer solution was withdrawn.

800 ml of n-hexane was added to the obtained organic layer to precipitate crystals, and the precipitated crystals were collected by filtration. The residues were washed with n-hexane and dried under vacuum to afford 17.84 g of mixture 1 as a white solid.

The obtained crystals were analyzed by high performance liquid chromatography (HPLC) and quantitated using a calibration curve. It was confirmed that the crystals contained 13.04 g (31.16 mmol) of a polymerizable compound having Formula (Ia) (hereinafter occasionally referred to as "monoester") and 4.76 g (7.15 mmol) of a polymerizable compound having Formula (IIa) (hereinafter occasionally referred to as "diester").

Further, the obtained crystals were analyzed by $^{13}$C-NMR (DMF-d7) to calculate the content of 1,4-cyclohexanedicarboxylic acid. It was confirmed and the crystals contained 40 mg (0.23 mmol) of 1,4-cyclohexanedicarboxylic acid. The molar proportions of the components calculated based on their compositional ratios were monoester: 80.84 mol %, diester: 18.56 mol %, and cyclohexanedicarboxylic acid: 0.60 mol %.

(Example 2) Production of Mixture 2

The same operation as in Example 1 was carried out except that 200 ml of CPME as a reaction solvent was replaced by 150 ml of tetrahydrofuran (THF). As a result, 17.91 g of a white solid was obtained.

Using the same method as in Example 1, the composition of the obtained solid was confirmed and it was confirmed that the solid contained 12.89 g (30.81 mmol) of the target monoester, 4.98 g (7.49 mmol) of diester, and 41 mg (0.24 mmol) of cyclohexanedicarboxylic acid. The molar proportions calculated based on their compositional ratios were monoester: 79.94 mol %, diester: 19.44 mol %, and cyclohexanedicarboxylic acid: 0.61 mol %.

(Example 3) Production of Mixture 3

The same operation as in Example 1 was carried out except that 200 ml of CPME as a reaction solvent was replaced by 200 ml of methyl tertiary butyl ether (MTBE). As a result, 17.70 g of a white solid was obtained.

The composition of the solid was confirmed using the same method and it was confirmed that the solid contained 12.52 g (29.92 mmol) of the target monoester, 5.14 g (7.73 mmol) of diester, and 43 mg (0.25 mmol) of cyclohexanedicarboxylic acid. The molar proportions calculated based on their compositional ratios were monoester: 78.94 mol %, diester: 20.39 mol %, and cyclohexanedicarboxylic acid: 0.67 mol %.

(Example 4) Production of Mixture 4

The same operation as in Example 1 was carried out except that 200 ml of CPME as a reaction solvent was replaced by 200 ml of diethyl ether. As a result, 17.36 g of a white solid was obtained.

The composition of the solid was confirmed using the same method and it was confirmed that the solid contained 11.91 g (28.46 mmol) of the target monoester, 5.40 g (8.13 mmol) of diester, and 48 mg (0.28 mmol) of cyclohexanedicarboxylic acid. The molar proportions calculated based on their compositional ratios were monoester: 77.20 mol %, diester: 22.05 mol %, and cyclohexanedicarboxylic acid: 0.75 mol %.

(Example 5) Production of Mixture 5

The same operation as in Example 1 was carried out except that 200 ml of CPME as a reaction solvent was replaced by 300 ml of dibutyl ether. As a result, 18.48 g of a white solid was obtained.

The composition of the solid was confirmed using the same method and it was confirmed that the solid contained 15.07 g (36.01 mmol) of the target monoester, 3.38 g (5.08 mmol) of diester, and 27 mg (0.16 mmol) of cyclohexanedicarboxylic acid. The molar proportions calculated based on their compositional ratios were monoester: 87.30 mol %, diester: 12.32 mol %, and cyclohexanedicarboxylic acid: 0.38 mol %.

(Example 6) Production of Mixture 6

The same operation as in Example 1 was carried out except that 200 ml of CPME as a reaction solvent was replaced by 300 ml of diisopropyl ether. As a result, 17.74 g of a white solid was obtained.

The composition of the solid was confirmed using the same method and it was confirmed that the solid contained 13.48 g (32.22 mmol) of the target monoester, 4.22 g (6.35 mmol) of diester, and 38 mg (0.22 mmol) of cyclohexanedicarboxylic acid. The molar proportions calculated based on their compositional ratios were monoester: 83.06 mol %, diester: 16.37 mol %, and cyclohexanedicarboxylic acid: 0.57 mol %.

(Example 7) Production of Mixture 7

The same operation as in Example 1 was carried out except that 200 ml of CPME as a reaction solvent was replaced by 200 ml of 1,2-dimethoxyethane. As a result, 17.76 g of a white solid was obtained.

The composition of the solid was confirmed using the same method and it was confirmed that the solid contained 11.26 g (26.90 mmol) of the target monoester, 6.45 g (9.70 mmol) of diester, and 50 mg (0.29 mmol) of cyclohexanedicarboxylic acid. The molar proportions calculated based on their compositional ratios were monoester: 72.91 mol %, diester: 26.30 mol %, and cyclohexanedicarboxylic acid: 0.79 mol %.

(Example 8) Production of Mixture 8

The same operation as in Example 1 was carried out except that 200 ml of CPME as a reaction solvent was replaced by 200 ml of 2-butanone. As a result, 16.29 g of a white solid was obtained.

The composition of the solid was confirmed using the same method and it was confirmed that the solid contained 10.56 g (25.22 mmol) of the target monoester, 5.68 g (8.54 mmol) of diester, and 58 mg (0.34 mmol) of cyclohexanedicarboxylic acid. The molar proportions calculated based on their compositional ratios were monoester: 73.96 mol %, diester: 25.05 mol %, and cyclohexanedicarboxylic acid: 0.99 mol %.

(Example 9) Production of Mixture 9

The same operation as in Example 1 was carried out except that 200 ml of CPME as a reaction solvent was replaced by 200 ml of chloroform. As a result, 17.25 g of a white solid was obtained.

The composition of the solid was confirmed using the same method and it was confirmed that the solid contained 11.63 g (27.80 mmol) of the target monoester, 5.57 g (8.37 mmol) of diester, and 50 mg (0.29 mmol) of cyclohexanedicarboxylic acid. The molar proportions calculated based on their compositional ratios were monoester: 76.24 mol %, diester: 22.97 mol %, and cyclohexanedicarboxylic acid: 0.79 mol %.

(Example 10) Production of Mixture 10

The same operation as in Example 1 was carried out except that 200 ml of CPME as a reaction solvent was replaced by 200 ml of ethyl acetate. As a result, 17.73 g of a white solid was obtained.

The composition of the solid was confirmed using the same method and it was confirmed that the solid contained 11.80 g (28.20 mmol) of the target monoester, 5.88 g (8.84 mmol) of diester, and 47 mg (0.28 mmol) of cyclohexanedicarboxylic acid. The molar proportions calculated based on their compositional ratios were monoester: 75.57 mol %, diester: 23.69 mol %, and cyclohexanedicarboxylic acid: 0.74 mol %.

(Example 11) Production of Mixture 11

The same operation as in Example 1 was carried out except that 200 ml of CPME as a reaction solvent was replaced by 200 ml of toluene. As a result, 17.04 g of a white solid was obtained.

The composition of the solid was confirmed using the same method and it was confirmed that the solid contained 12.30 g (29.39 mmol) of the target monoester, 4.70 g (7.06 mmol) of diester, and 46 mg (0.27 mmol) of cyclohexanedicarboxylic acid. The molar proportions calculated based on their compositional ratios were monoester:monoester: 80.04 mol %, diester: 19.23 mol %, and cyclohexanedicarboxylic acid: 0.73 mol %.

(Example 12) Production of Mixture 12

The same operation as in Example 1 was carried out except that 200 ml of CPME as a reaction solvent was replaced by a mixed solvent of 70 ml THF and 130 ml cyclohexane. As a result, 16.91 g of a white solid was obtained.

The composition of the solid was confirmed using the same method and it was confirmed that the solid contained 13.79 g (32.96 mmol) of the target monoester, 3.08 g (4.63 mmol) of diester, and 38 mg (0.22 mmol) of cyclohexanedicarboxylic acid. The molar proportions calculated based on their compositional ratios were monoester: 87.17 mol %, diester: 12.25 mol %, and cyclohexanedicarboxylic acid: 0.59 mol %.

(Example 13) Production of Mixture 13

The same operation as in Example 1 was carried out except that 200 ml of CPME as a reaction solvent was replaced by a mixed solvent of 150 ml CPME and 100 ml cyclohexane. As a result, 17.31 g of a white solid was obtained.

The composition of the solid was confirmed using the same method and it was confirmed that the solid contained 13.10 g (31.30 mmol) of the target monoester, 4.17 g (6.27 mmol) of diester, 41 mg (0.24 mmol) of cyclohexanedicarboxylic acid. The molar proportions calculated based on their compositional ratios were monoester: 82.77 mol %, diester: 16.59 mol %, and cyclohexanedicarboxylic acid: 0.63 mol %.

(Example 14) Production of Mixture 14

The same operation as in Example 1 was carried out except that 200 ml of CPME as a reaction solvent was replaced by a mixed solvent of 100 ml dibutyl ether and 100 ml CPME. As a result, 17.96 g of a white solid was obtained.

The composition of the solid was confirmed using the same method and it was confirmed that the solid contained 12.83 g (30.66 mmol) of the target monoester, 5.09 g (7.65 mmol) of diester, and 41 mg (0.24 mmol) of cyclohexanedicarboxylic acid. The molar proportions calculated based on their compositional ratios were monoester: 79.54 mol %, diester: 19.85 mol %, and cyclohexanedicarboxylic acid: 0.62 mol %.

(Example 15) Production of Mixture 15

The same operation as in Example 1 was carried out except that 200 ml of CPME as a reaction solvent was replaced by a mixed solvent of 150 ml dibutyl ether and 50 ml toluene. As a result, 17.56 g of a white solid was obtained.

The composition of the solid was confirmed using the same method and it was confirmed that the solid contained 12.61 g (30.14 mmol) of the target monoester, 4.90 g (7.38 mmol) of diester, and 43 mg (0.25 mmol) of cyclohexanedicarboxylic acid. The molar proportions calculated based on their compositional ratios were monoester: 79.80 mol %, diester: 19.53 mol %, and cyclohexanedicarboxylic acid: 0.67 mol %.

(Example 16) Production of Mixture 16

The same operation as in Example 1 was carried out except that 200 ml of CPME as a reaction solvent was replaced by a mixed solvent of 150 ml CPME and 50 ml toluene. As a result, 17.84 g of a white solid was obtained.

The composition of the solid was confirmed using the same method and it was confirmed that the solid contained 12.14 g (29.02 mmol) of the target monoester, 5.65 g (8.50 mmol) of diester, and 45 mg (0.26 mmol) of cyclohexanedicarboxylic acid. The molar proportions calculated based on their compositional ratios were monoester: 76.80 mol %, diester: 22.51 mol %, and cyclohexanedicarboxylic acid: 0.69 mol %.

(Example 17) Production of Mixture 17

A three-necked reactor equipped with a thermometer was charged with 10.0 g (47.83 mmol) of trans-1,4-cyclohexanedicarboxylic acid dichloride and 200 ml of CPME under a nitrogen stream. To the reactor was added 12.64 g (47.83 mmol) of 4-(6-acryloyloxy-hex-1-yloxy)phenol (manufactured by DKSH). The reactor was immersed in an ice bath to lower the internal temperature of the reaction solution to 0° C. 4.83 g (47.83 mmol) of triethylamine was slowly added dropwise over 5 minutes while keeping the internal temperature of the reaction solution at 10° C. or below. After completion of the dropwise addition, the temperature of the whole mass was raised back to 25° C. and stirring was further performed for 1 hour.

To the obtained reaction solution was added 100 ml of distilled water and after washing at 25° C. for 2 hours, the aqueous layer was withdrawn. The organic layer was further washed twice with 250 ml of a 1 mol/L buffer solution (pH 5.5) consisting of acetic acid and sodium acetate, and then the buffer solution was withdrawn. 800 ml of n-hexane was added to the obtained organic layer to precipitate crystals, and the precipitated crystals were collected by filtration. The residues were washed with n-hexane and dried under vacuum to afford 17.93 g of mixture 17 as a white solid.

The obtained crystals were analyzed by high performance liquid chromatography (HPLC) and monoester and diester were quantitated using a calibration curve. It was confirmed that the crystals contained 13.14 g (31.40 mmol) of the target monoester and 4.79 g (7.21 mmol) of diester. Further, the obtained crystals were analyzed by $^{13}$C-NMR (DMF-d7) to calculate the content of cyclohexanedicarboxylic acid. It was confirmed that cyclohexanedicarboxylic acid was below detection limit. The molar proportions of the components calculated based on their compositional ratios were monoester: 81.33 mol % and diester: 18.67 mol %.

(Example 18) Production of Mixture 18

The same operation as in Example 17 was carried out except that 200 ml of CPME as a reaction solvent was replaced by 150 ml of THF. As a result, 18.01 g of a white solid was obtained.

Using the same method, the composition of the obtained solid was confirmed and it was confirmed that the solid contained 12.99 g (31.04 mmol) of the target monoester and 5.02 g (7.55 mmol) of diester, with cyclohexanedicarboxylic acid being below detection limit. The molar proportions calculated based on their compositional ratios were monoester: 80.44 mol % and diester: 19.56 mol %.

(Example 19) Production of Mixture 19

The same operation as in Example 17 was carried out except that 200 ml of CPME as a reaction solvent was replaced by 200 ml of MTBE. As a result, 17.79 g of a white solid was obtained.

Using the same method, the composition of the obtained solid was confirmed and it was confirmed that the solid contained 12.61 g (30.14 mmol) of the target monoester and 5.18 g (7.79 mmol) of diester, with cyclohexanedicarboxylic acid being below detection limit. The molar proportions calculated based on their compositional ratios were monoester: 79.47 mol % and diester: 19.56 mol %.

(Example 20) Production of Mixture 20

The same operation as in Example 17 was carried out except that 200 ml of CPME as a reaction solvent was replaced by 200 ml of diethyl ether. As a result, 17.45 g of a white solid was obtained.

Using the same method, the composition of the obtained solid was confirmed and it was confirmed that the solid contained 12.00 g (28.68 mmol) of the target monoester and 5.44 g (8.19 mmol) of diester, with cyclohexanedicarboxylic acid being below detection limit. The molar proportions calculated based on their compositional ratios were monoester: 77.79 mol % and diester: 22.21 mol %.

(Example 21) Production of Mixture 21

The same operation as in Example 17 was carried out except that 200 ml of CPME as a reaction solvent was replaced by 300 ml of dibutyl ether. As a result, 18.59 g of a white solid was obtained.

Using the same method, the composition of the obtained solid was confirmed and it was confirmed that the solid contained 15.19 g (36.29 mmol) of the target monoester and 3.40 g (5.12 mmol) of diester, with cyclohexanedicarboxylic acid being below detection limit. The molar proportions calculated based on their compositional ratios were monoester: 87.63 mol % and diester: 12.37 mol %.

(Example 22) Production of Mixture 22

The same operation as in Example 17 was carried out except that 200 ml of CPME as a reaction solvent was replaced by 300 ml of diisopropyl ether. As a result, 17.84 g of a white solid was obtained.

Using the same method, the composition of the obtained solid was confirmed and it was confirmed that the solid contained 13.59 g (32.47 mmol) of the target monoester and 4.25 g (6.40 mmol) of diester, with cyclohexanedicarboxylic acid being below detection limit. The molar proportions calculated based on their compositional ratios were monoester: 83.53 mol % and diester: 16.47 mol %.

(Example 23) Production of Mixture 23

The same operation as in Example 17 was carried out except that 200 ml of CPME as a reaction solvent was replaced by 200 ml of 1,2-dimethoxyethane. As a result, 17.84 g of a white solid was obtained.

Using the same method, the composition of the obtained solid was confirmed and it was confirmed that the solid contained 11.34 g (27.10 mmol) of the target monoester and 6.50 g (9.78 mmol) of diester, with cyclohexanedicarboxylic acid being below detection limit. The molar proportions calculated based on their compositional ratios were monoester: 73.49 mol % and diester: 26.51 mol %.

(Example 24) Production of Mixture 24

The same operation as in Example 17 was carried out except that 200 ml of CPME as a reaction solvent was replaced by 200 ml of 2-butanone. As a result, 16.36 g of a white solid was obtained.

Using the same method, the composition of the obtained solid was confirmed and it was confirmed that the solid contained 10.64 g (25.42 mmol) of the target monoester and 5.72 g (8.61 mmol) of diester, with cyclohexanedicarboxylic acid being below detection limit. The molar proportions calculated based on their compositional ratios were monoester: 74.70 mol % and diester: 25.30 mol %.

(Example 25) Production of Mixture 25

The same operation as in Example 17 was carried out except that 200 ml of CPME as a reaction solvent was replaced by 200 ml of chloroform. As a result, 17.33 g of a white solid was obtained.

Using the same method, the composition of the obtained solid was confirmed and it was confirmed that the solid contained 11.72 g (28.01 mmol) of the target monoester and 5.61 g (8.44 mmol) of diester, with cyclohexanedicarboxylic acid being below detection limit. The molar proportions calculated based on their compositional ratios were monoester: 76.85 mol % and diester: 23.15 mol %.

(Example 26) Production of Mixture 26

The same operation as in Example 17 was carried out except that 200 ml of CPME as a reaction solvent was replaced by 200 ml of ethyl acetate. As a result, 17.81 g of a white solid was obtained.

Using the same method, the composition of the obtained solid was confirmed and it was confirmed that the solid contained 11.89 g (28.42 mmol) of the target monoester and 5.92 g (8.91 mmol) of the diester, with cyclohexanedicarboxylic acid being below detection limit. The molar proportions calculated based on their compositional ratios were monoester: 76.13 mol % and diester: 23.87 mol %.

(Example 27) Production of Mixture 27

The same operation as in Example 17 was carried out except that 200 ml of CPME as a reaction solvent was replaced by 200 ml of toluene. As a result, 17.13 g of a white solid was obtained.

Using the same method, the composition of the obtained solid was confirmed and it was confirmed that the solid contained 12.39 g (29.62 mmol) of the target monoester and 4.73 g (7.12 mmol) of diester, with cyclohexanedicarboxylic acid being below detection limit. The molar proportions calculated based on their compositional ratios were monoester: 80.63 mol % and diester: 19.37 mol %.

(Example 28) Production of Mixture 28

The same operation as in Example 17 was carried out except that 200 ml of CPME as a reaction solvent was replaced by a mixed solvent of 70 ml THF and 130 ml cyclohexane. As a result, 17.00 g of a white solid was obtained.

Using the same method, the composition of the obtained solid was confirmed and it was confirmed that the solid contained 13.90 g (33.21 mmol) of the target monoester and 3.10 g (4.67 mmol) of diester, with cyclohexanedicarboxylic acid being below detection limit. The molar proportions calculated based on their compositional ratios were monoester: 87.68 mol % and diester: 12.32 mol %.

(Example 29) Production of Mixture 29

The same operation as in Example 17 was carried out except that 200 ml of CPME as a reaction solvent was replaced by a mixed solvent of 150 ml CPME and 100 ml cyclohexane. As a result, 17.40 g of a white solid was obtained.

Using the same method, the composition of the obtained solid was confirmed and it was confirmed that the solid contained 13.20 g (31.53 mmol) of the target monoester and 4.20 g (6.32 mmol) of diester, with cyclohexanedicarboxylic acid being below detection limit. The molar proportions calculated based on their compositional ratios were monoester: 83.30 mol % and diester: 16.70 mol %.

(Example 30) Production of Mixture 30

The same operation as in Example 17 was carried out except that 200 ml of CPME as a reaction solvent was replaced by a mixed solvent of 100 ml dibutyl ether and 100 ml CPME. As a result, 18.05 g of a white solid was obtained.

Using the same method, the composition of the obtained solid was confirmed and it was confirmed that the solid contained 12.93 g (30.90 mmol) of the target monoester and 5.12 g (7.71 mmol) of the diester, with cyclohexanedicarboxylic acid being below detection limit. The molar proportions calculated based on their compositional ratios were monoester: 80.03 mol % and diester: 19.97 mol %.

(Example 31) Production of Mixture 31

The same operation as in Example 17 was carried out except that 200 ml of CPME as a reaction solvent was replaced by a mixed solvent of 150 ml dibutyl ether and 50 ml toluene. As a result, 17.65 g of a white solid was obtained.

Using the same method, the composition of the obtained solid was confirmed and it was confirmed that the solid contained 12.71 g (30.37 mmol) of the target monoester and 4.94 g (7.43 mmol) of diester, with cyclohexanedicarboxylic acid being below detection limit. The molar proportions calculated based on their compositional ratios were monoester: 80.34 mol % and diester: 19.66 mol %.

(Example 32) Production of Mixture 32

The same operation as in Example 17 was carried out except that 200 ml of CPME as a reaction solvent was replaced by a mixed solvent of 150 ml CPME and 50 ml toluene. As a result, 17.93 g of a white solid was obtained.

Using the same method, the composition of the obtained solid was confirmed and it was confirmed that the solid contained 12.24 g (29.24 mmol) of the target monoester and 5.70 g (8.57 mmol) of diester, with cyclohexanedicarboxylic acid being below detection limit. The molar proportions calculated based on their compositional ratios were monoester: 77.34 mol % and diester: 22.66 mol %.

(Example 33) Production of Mixture 33

A three-necked reactor equipped with a thermometer was charged with 10.0 g (47.83 mmol) of trans-1,4-cyclohexanedicarboxylic acid dichloride and 200 ml of CPME under a nitrogen stream. To the reactor was added 12.64 g (47.83 mmol) of 4-(6-acryloyloxy-hex-1-yloxy)phenol (manufactured by DKSH). The reactor was immersed in an ice bath to lower the internal temperature of the reaction solution to 0° C. 4.83 g (47.83 mmol) of triethylamine was slowly added dropwise over 5 minutes while keeping the internal temperature of the reaction solution at 10° C. or below. After completion of the dropwise addition, the temperature of the whole mass was raised back to 25° C. and stirring was further performed for 1 hour. To the obtained reaction solution was added 100 ml of distilled water and after washing at 25° C. for 2 hours, the aqueous layer was withdrawn. The organic layer was further washed twice with 250 ml of a 1 mol/L buffer solution (pH 5.5) consisting of acetic acid and sodium acetate, and then the buffer solution was withdrawn. The obtained organic layer was gradually cooled to 0° C. with stirring, and after stirred at 0° C. for 1 hour, the precipitated solid was filtered off. 500 ml of n-hexane was added to the filtrate to precipitate crystals, and the precipitated crystals were collected by filtration. The residues were washed with n-hexane and dried under vacuum to afford 14.34 g of mixture 33 as a white solid.

The obtained crystals were analyzed by HPLC and monoester and diester were quantitated using a calibration curve. It was confirmed that the crystals contained 13.14 g (31.40 mmol) of the target monoester and 1.20 g (1.80 mmol) of diester. Further, the obtained crystals were analyzed by $^{13}$C-NMR (DMF-d7) to calculate the content of cyclohexanedicarboxylic acid and it was confirmed that cyclohexanedicarboxylic acid was below detection limit. The molar proportions of the components calculated based on their compositional ratios were monoester: 94.57 mol % and diester: 5.43 mol %.

(Example 34) Production of Mixture 34

A three-necked reactor equipped with a thermometer was charged with 10.0 g (47.83 mmol) of trans-1,4-cyclohexanedicarboxylic acid dichloride and 300 ml of dibutyl ether under a nitrogen stream. To the reactor was added 12.64 g (47.83 mmol) of 4-(6-acryloyloxy-hex-1-yloxy) phenol (manufactured by DKSH). The reactor was immersed in an ice bath to lower the internal temperature of the reaction solution to 0° C. 4.83 g (47.83 mmol) of triethylamine was slowly added dropwise over 5 minutes while keeping the internal temperature of the reaction solution at 10° C. or below. After completion of the dropwise addition, the temperature of the whole mass was raised back to 25° C. and stirring was further performed for 1 hour. To the obtained reaction solution was added 100 ml of distilled water and after washing at 25° C. for 2 hours, the aqueous layer was withdrawn. The organic layer was further washed twice with 250 ml of a 1 mol/L buffer solution (pH 5.5) consisting of acetic acid and sodium acetate, and then the buffer solution was withdrawn. The obtained organic layer was gradually cooled to 0° C. with stirring, and after stirred at 0° C. for 1 hour, the precipitated solid was filtered off. 500 ml of n-hexane was added to the filtrate to precipitate crystals, and the precipitated crystals were collected by filtration. The residues were washed with n-hexane and dried under vacuum to afford 16.04 g of mixture 34 as a white solid.

The obtained crystals were analyzed by HPLC and monoester and diester were quantitated using a calibration curve. It was confirmed that the crystals contained 15.19 g (36.29 mmol) of the target monoester and 0.85 g (1.28 mmol) of diester. Further, the obtained crystals were analyzed by $^{13}$C-NMR (DMF-d7) to calculate the content of cyclohexanedicarboxylic acid and it was confirmed that cyclohexanedicarboxylic acid was below detection limit. The molar proportions of the components calculated based on their compositional ratios were monoester: 96.59 mol % and diester: 3.41 mol %.

(Example 35) Production of Mixture 35

A three-necked reactor equipped with a thermometer was charged with 10 g (58 mmol) of trans-1,4-cyclohexane and 30 g of N-methyl-2-pyrrolidone (NMP) under a nitrogen stream to prepare a solution. To the obtained solution were added 3.07 g (11.6 mmol) of 4-(6-acryloyloxy-hex-1-yloxy) phenol having Formula (IVa) (manufactured by DKSH) and 0.71 g (5.8 mmol) of 4-(dimethylamino)pyridine. 2.67 g (13.9 mmol) of 1-(3-dimethylaminopropyl)-3-ethylcarbodiimide hydrochloride was slowly added to the solution dropwise over 1 hour. The whole mass was stirred for 15 hours to effect esterification reaction. To the obtained reaction solution were added 250 ml of distilled water, 50 ml of salt water and 200 ml of ethyl acetate. After stirring the whole mass at 25° C., liquid separation was performed and the aqueous layer was withdrawn. The organic layer was further washed 5 times with 250 ml of a 1 mol/L buffer solution (pH 5.5) consisting of acetic acid and sodium acetate, and then the buffer solution was withdrawn. 800 ml of n-hexane was added to the obtained organic layer to precipitate crystals, and the precipitated crystals were collected by filtration. The residues were washed with n-hexane and dried under vacuum to afford 18.0 g of mixture 35 as a white solid.

The obtained crystals were analyzed by HPLC and monoester and diester were quantitated using a calibration curve. It was confirmed that the crystals contained 13.19 g (31.52 mmol) of the target monoester and 4.81 g (7.24 mmol) of diester. Further, the obtained crystals were analyzed by $^{13}$C-NMR (DMF-d7) to calculate the content of cyclohexanedicarboxylic acid and it was confirmed that cyclohexanedicarboxylic acid was below detection limit. The molar proportions of the components calculated based on their compositional ratios were monoester: 81.32 mol % and diester: 18.68 mol %.

(Example 36) Production of Mixture 36

A three-necked reactor equipped with a thermometer was charged with 10.0 g (47.83 mmol) of trans-1,4-cyclohexanedicarboxylic acid dichloride, 84 ml of CPME and 31 ml of THF under a nitrogen stream. To the reactor was added 12.04 g (45.55 mmol) of 4-(6-acryloyloxy-hex-1-yloxy) phenol (manufactured by DKSH). The reactor was immersed in an ice bath to lower the internal temperature of the reaction solution to 0° C. 4.83 g (47.83 mmol) of triethylamine was slowly added dropwise over 5 minutes while keeping the internal temperature of the reaction solution at 10° C. or below. After completion of the dropwise addition, stirring was further performed for 1 hour while keeping the temperature of the whole mass to 10° C. or below.

To the obtained reaction solution was added 30 ml of distilled water. After heating the reaction solution to 50° C., the reaction solution was washed for 2 hours (for hydrolysis reaction) and the aqueous layer was withdrawn. Further, after newly adding 30 ml of distilled water to the obtained organic layer, the whole mass was washed at 50° C. for 2 hours (for hydrolysis reaction), and the aqueous layer was withdrawn. After cooling the obtained organic layer to 40° C., 50 g of a 1 mol/L buffer solution (pH 5.5) consisting of acetic acid and sodium acetate was further added and stirred for washing. The buffer solution aqueous layer was then withdrawn to afford an organic layer. This washing operation with a buffer solution was performed 5 times in total. The obtained organic layer was further washed with 30 ml of distilled water, and the aqueous layer was withdrawn.

To the obtained organic layer was added 214 ml of n-hexane at 40° C., and then cooled to 0° C. to precipitate crystals. The precipitated crystals were collected by filtration. The residues were washed with n-hexane and dried under vacuum to afford 16.78 g of mixture 36 as a white solid.

The obtained crystals were analyzed by HPLC and monoester and diester were quantitated using a calibration curve. It was confirmed that the crystals contained 11.49 g (27.45 mmol) of the target monoester and 5.29 g (7.96 mmol) of diester. Further, the obtained crystals were analyzed by $^{13}$C-NMR (DMF-d7) to calculate the content of cyclohexanedicarboxylic acid and it was confirmed that cyclohexanedicarboxylic acid was below detection limit. The molar proportions of the components calculated based on their compositional ratios were monoester: 77.52 mol % and diester: 22.48 mol %.

(Comparative Example 1) Production of Mixture A

A three-necked reactor equipped with a thermometer was charged with 10.0 g (47.83 mmol) of trans-1,4-cyclohexanedicarboxylic acid dichloride and 200 ml of CPME under a nitrogen stream. To the reactor was added 12.64 g (47.83 mmol) of 4-(6-acryloyloxy-hex-1-yloxy)phenol (manufactured by DKSH). The reactor was immersed in an ice bath to lower the internal temperature of the reaction solution to 0° C. 4.83 g (47.83 mmol) of triethylamine was slowly added dropwise over 5 minutes while keeping the internal temperature of the reaction solution at 10° C. or below. After completion of the dropwise addition, the temperature of the whole mass was raised back to 25° C. and stirring was further performed for 1 hour. To the obtained reaction solution was added 100 ml of distilled water and after washing at 25° C. for 2 hours, the aqueous layer was withdrawn. 800 ml of n-hexane was added to the organic layer to precipitate crystals, and the precipitated crystals were collected by filtration. The residues were washed with n-hexane and dried under vacuum to afford 19.96 g of mixture A as a white solid.

The obtained crystals were analyzed by HPLC and monoester and diester were quantitated using a calibration curve. It was confirmed that the crystals contained 13.14 g (31.40 mmol) of the target monoester and 4.79 g (7.21 mmol) of diester. Further, the obtained crystals were analyzed by $^{13}$C-NMR (DMF-d7) and it was confirmed that the crystals contained 2.02 g (11.76 mmol) of cyclohexanedicarboxylic acid. The molar proportions of the components calculated based on their compositional ratios were monoester: 62.34 mol %, diester: 14.31 mol %, and cyclohexanedicarboxylic acid: 23.35 mol %.

(Comparative Example 2) Production of Mixture B

The same operation as in Comparative Example 1 was carried out except that 200 ml of CPME as a reaction solvent was replaced by 300 ml of dibutyl ether. As a result, 19.95 g of a white solid was obtained.

Using the same method as in Comparative Example 1, the composition of the obtained solid was confirmed and it was confirmed that the solid contained 15.19 g (36.29 mmol) of the target monoester, 3.40 g (5.12 mmol) of diester and 1.36 g (7.91 mmol) of cyclohexanedicarboxylic acid. The molar proportions calculated based on their compositional ratios were monoester: 73.58 mol %, diester: 10.38 mol % and cyclohexanedicarboxylic acid: 16.04 mol %.

(Comparative Example 3) Production of Mixture C

A three-necked reactor equipped with a thermometer was charged with 10.0 g (47.83 mmol) of trans-1,4-cyclohexanedicarboxylic acid dichloride and 100 ml of NMP under a nitrogen stream. To the reactor was added 12.64 g (47.83 mmol) of 4-(6-acryloyloxy-hex-1-yloxy)phenol (manufactured by DKSH). The reactor was immersed in an ice bath to lower the internal temperature of the reaction solution to 0° C. 4.83 g (47.83 mmol) of triethylamine was slowly added dropwise over 5 minutes while keeping the internal temperature of the reaction solution at 10° C. or below. After completion of the dropwise addition, the temperature of the whole mass was raised back to 25° C. and stirring was further performed for 1 hour. To the obtained reaction solution was added 1,000 ml of distilled water and after stirring at 25° C. for 2 hours, extraction was performed with 200 ml of ethyl acetate. 800 ml of n-hexane was added to the obtained organic layer to precipitate crystals, and the precipitated crystals were collected by filtration. The residues were washed with n-hexane and dried under vacuum to afford 20.46 g of mixture C as a white solid.

The obtained crystals were analyzed by HPLC and monoester and diester were quantitated using a calibration curve. It was confirmed that the crystals contained 6.98 g (16.68 mmol) of the target monoester and 9.54 g (14.34 mmol) of diester. Further, the obtained crystals were analyzed by $^{13}$C-NMR (DMF-d7) and it was confirmed that the crystals contained 3.94 g (22.91 mmol) of cyclohexanedicarboxylic acid. The molar proportions of the components calculated based on their compositional ratios were monoester: 30.92 mol %, diester: 26.60 mol %, and cyclohexanedicarboxylic acid: 42.48 mol %.

(Comparative Example 4) Production of Mixture D

A three-necked reactor equipped with a thermometer was charged with 10.0 g (47.83 mmol) of trans-1,4-cyclohexanedicarboxylic acid dichloride and 100 ml of γ-butyrolactone under a nitrogen stream. To the reactor was added 12.64 g (47.83 mmol) of 4-(6-acryloyloxy-hex-1-yloxy)phenol (manufactured by DKSH). The reactor was immersed in an ice bath to lower the internal temperature of the reaction solution to 0° C. 4.83 g (47.83 mmol) of triethylamine was slowly added dropwise over 5 minutes while keeping the internal temperature of the reaction solution at 10° C. or below. After completion of the dropwise addition, the temperature of the whole mass was raised back to 25° C. and stirring was further performed for 1 hour. To the obtained reaction solution was added 1,000 ml of distilled water and after stirring at 25° C. for 2 hours, extraction was performed with 200 ml of ethyl acetate. 800 ml of n-hexane was added to the obtained organic layer to precipitate crystals, and the precipitated crystals were collected by filtration. The residues were washed with n-hexane and dried under vacuum to afford 20.59 g of mixture D as a white solid.

The obtained crystals were analyzed by HPLC and monoester and diester were quantitated using a calibration curve. It was confirmed that the crystals contained 9.64 g (23.03 mmol) of the target monoester and 7.89 g (11.86 mmol) of diester. Further, the obtained crystals were analyzed by $^{13}$C-NMR (DMF-d7) and it was confirmed that the crystals contained 3.07 g (17.80 mmol) of cyclohexanedicarboxylic acid. The molar proportions of the components calculated based on their compositional ratios were monoester: 43.70 mol %, diester: 22.51 mol % and cyclohexanedicarboxylic acid: 33.79 mol %.

(Comparative Example 5) Production of Mixture E

A three-necked reactor equipped with a thermometer was charged with 10.0 g (47.83 mmol) of trans-1,4-cyclohexanedicarboxylic acid dichloride, 84 ml of CPME and 31 ml of THF under a nitrogen stream. To the reactor was added 12.04 g (45.55 mmol) of 4-(6-acryloyloxy-hex-1-yloxy) phenol (manufactured by DKSH). The reactor was immersed in an ice bath to lower the internal temperature of the reaction solution to 0° C. 4.83 g (47.83 mmol) of triethylamine was slowly added dropwise over 5 minutes while keeping the internal temperature of the reaction solution at 10° C. or below. After completion of the dropwise addition, stirring was further performed for 1 hour while keeping the temperature of the whole mass to 10° C. or below.

To the obtained reaction solution was added 30 ml of distilled water. After heating the reaction solution to 50° C., the reaction solution was washed for 2 hours (for hydrolysis reaction) and the aqueous layer was withdrawn. Further, after newly adding 30 ml of distilled water to the obtained organic layer, the whole mass was washed at 50° C. for 2 hours (for hydrolysis reaction), and the aqueous layer was withdrawn. The obtained organic layer was cooled to 40° C. To the organic layer was added 214 ml of n-hexane at 40° C. and then cooled to 0° C. to precipitate crystals. The precipitated crystals were collected by filtration. The residues were washed with n-hexane and dried under vacuum to afford 18.72 g of mixture E as a white solid.

The obtained crystals were analyzed by HPLC and monoester and diester were quantitated using a calibration curve. It was confirmed that the crystals contained 11.50 g (27.48 mmol) of the target monoester and 5.30 g (7.97 mmol) of diester. Further, the obtained crystals were analyzed by $^{13}$C-NMR (DMF-d7) and it was confirmed that the crystals contained 1.92 g (11.56 mmol) of cyclohexanedicarboxylic acid. The molar proportions of the components calculated based on their compositional ratios were monoester: 58.46 mol %, diester: 16.95 mol %, and cyclohexanedicarboxylic acid: 24.59 mol %.

(Example 37) Synthesis of Polymerizable Compound (IIIa)

Polymerizable compound (IIIa)

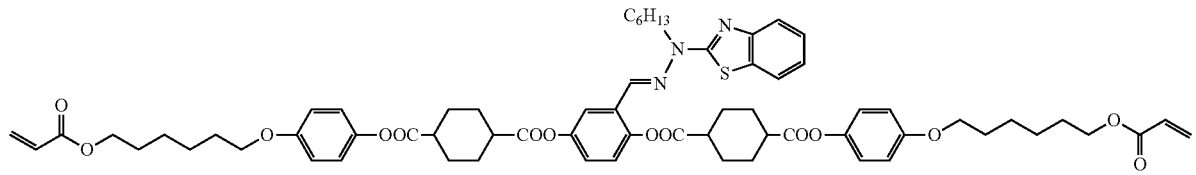

Step 1: Synthesis of Compound (3a)

Compound (3a)

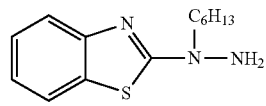

A four-necked reactor equipped with a thermometer was charged with 20.0 g (0.12 mol) of 2-hydrazinobenzothiazole and 200 ml of DMF under a nitrogen stream to prepare a homogeneous solution. To the solution were added 83.6 g (0.61 mol) of potassium carbonate and 30.8 g (0.15 mol) of 1-iodo-n-hexane, and the whole mass was stirred for 7 hours at 50° C. After completion of the reaction, the reaction solution was cooled to 20° C., and the reaction solution was poured into 1,000 ml of water and the mixture was extracted with 800 ml of ethyl acetate. The ethyl acetate layer was dried over anhydrous sodium sulfate and sodium sulfate was filtered off. Ethyl acetate was distilled off from the filtrate under reduced pressure on a rotary evaporator to afford a yellow solid. This yellow solid was purified by silica gel column chromatography (n-hexane/ethyl acetate=75:25 (v/v)) to afford 21.0 g of compound (3a) as a white solid (yield: 69.6%).

The structure of the target product was identified by $^1$H-NMR.

$^1$H-NMR (500 MHz, CDCl$_3$, TMS, δ ppm): 7.60 (dd, 1H, J=1.0 Hz, 8.0 Hz), 7.53 (dd, 1H, J=1.0 Hz, 8.0 Hz), 7.27 (ddd, 1H, J=1.0 Hz, 8.0 Hz, 8.0 Hz), 7.06 (ddd, 1H, J=1.0 Hz, 8.0 Hz, 8.0 Hz), 4.22 (s, 2H), 3.74 (t, 2H, J=7.5 Hz), 1.69-1.76 (m, 2H), 1.29-1.42 (m, 6H), 0.89 (t, 3H, J=7.0 Hz)

Step 2: Production of Polymerizable Compound (IIIa)

A three-necked reactor equipped with a thermometer was charged with 17.84 g (total amount) of mixture 1 synthesized in Example 1, 150 g of toluene and 1.5 g of DMF under a nitrogen stream, followed by cooling to 10° C. or lower. 5.94 g (50.0 mmol) of thionyl chloride was added dropwise while controlling the reaction temperature to 10° C. or lower. After completion of the dropwise addition, the temperature of the reaction solution was raised back to 25° C. and stirring was performed for 1 hour. After completion of the reaction, the reaction solution was concentrated to half of its volume on an evaporator, toluene was added to compensate for the volume lost during concentration, and the reaction solution was again concentrated to half of its volume on the evaporator. This series of operations was repeated 5 times to afford reaction solution 1.

Separately, 2.18 g (15.81 mmol) of 2,5-dihydroxybenzaldehyde and 4.80 g (47.44 mmol) of triethylamine were dissolved in 80 g of THF under a nitrogen stream in a three-necked reactor equipped with a thermometer, followed by cooling to 10° C. or below. To this solution was slowly added dropwise reaction solution 1 while keeping the internal temperature of the reaction solution at 10° C. or below. After completion of the dropwise addition, reaction was further effected for 1 hour while keeping the temperature of the reaction solution at 10° C. or below. The reaction solution became creamy due to precipitation of a hydrochloride salt of triethylamine produced by the reaction.

After completion of the reaction, 5.13 g (20.56 mmol) of compound (3a) synthesized in Step 1 above was added to the reaction solution while keeping the temperature at 10° C. or below, followed by addition of 20 g of 1.0N hydrochloric acid aqueous solution. The reaction solution was then heated to 40° C. and reacted for 5 hours. The hydrochloride salt of triethylamine which had precipitated upon heating to 40° C. was dissolved, forming a clear two-layered solution of toluene and water. After completion of the reaction, the reaction solution was cooled to 25° C., 300 g of ethyl acetate and 150 g of 10 wt % salt water were added for liquid separation, and the organic layer was separated. The obtained organic layer was further washed twice with 150 g of 2 wt % salt water. Thereafter, a volume of the obtained organic layer, corresponding to about 15% of total volume, was withdrawn on an evaporator. This concentrated solution was brought to 25° C. and a mixed solvent of 150 g methanol and 40 g water was slowly added dropwise. The solution was then cooled to 10° C. to precipitate crystals and the precipitated crystals were collected by filtration. 160 g of THF, 160 g of methanol and 10 mg of 2,6-di-tertiary-butyl-4-methylphenol were added to the residues and the residues were dissolved by heating the whole mass to 50° C. The solution was subjected to hot filtration at 50° C. The obtained filtrate was slowly cooled to 10° C. for recrystallization. The obtained crystals were isolated by filtration and dried using a vacuum dryer to afford 11.57 g of polymerizable compound (IIIa) (yield: 62.5%).

The structure of the target product was identified by $^1$H-NMR.

$^1$H-NMR (400 MHz, CDCl$_3$, TMS, δ ppm): 7.75 (d, 1H, J=2.5 Hz), 7.67-7.70 (m, 3H), 7.34 (ddd, 1H, J=1.0 Hz, 7.0 Hz, 7.5 Hz), 7.17 (ddd, 1H, J=1.0 Hz, 7.5 Hz, 7.5 Hz), 7.12 (d, 1H, J=9.0 Hz), 7.10 (dd, 1H, J=2.5 Hz, 9.0 Hz), 6.99 (d, 2H, J=9.0 Hz), 6.98 (d, 2H, J=9.0 Hz), 6.88 (d, 4H, J=9.0 Hz), 6.40 (dd, 2H, J=1.5 Hz, 17.0 Hz), 6.13 (dd, 2H, J=10.5 Hz, 17.5 Hz), 5.82 (dd, 2H, J=1.5 Hz, 10.5 Hz), 4.30 (t, 2H, J=8.0 Hz), 4.18 (t, 4H, J=6.5 Hz), 3.95 (t, 4H, J=6.5 Hz), 2.58-2.70 (m, 4H), 2.31-2.35 (m, 8H), 1.66-1.82 (m, 18H), 1.31-1.54 (m, 14H), 0.90 (t, 3H, J=7.0 Hz)

Example 38

The same operation as in Example 37 was performed except that in Step 2, 17.84 g (total amount) of mixture 1 synthesized in Example 1 was changed to 17.91 g (total amount) of mixture 2 synthesized in Example 2; 2.18 g (15.81 mmol) of 2,5-dihydroxybenzaldehyde to 2.16 g (15.64 mmol); 4.80 g (47.44 mmol) of triethylamine to 4.75 g (46.92 mmol); and 5.13 g (20.56 mmol) of compound (3a) to 5.07 g (20.33 mmol). As a result, 11.39 g of polymerizable compound (IIIa) was obtained (yield: 62.2%).

Example 39

The same operation as in Example 37 was performed except that in Step 2, 17.84 g (total amount) of mixture 1 synthesized in Example 1 was changed to 17.70 g (total amount) of mixture 3 synthesized in Example 3; 2.18 g (15.81 mmol) of 2,5-dihydroxybenzaldehyde to 2.10 g (15.21 mmol); 4.80 g (47.44 mmol) of triethylamine to 4.62 g (45.63 mmol); and 5.13 g (20.56 mmol) of compound (3a) to 4.93 g (19.77 mmol). As a result, 10.97 g of polymerizable compound (IIIa) was obtained (yield: 61.6%).

Example 40

The same operation as in Example 37 was performed except that in Step 2, 17.84 g (total amount) of mixture 1 synthesized in Example 1 was changed to 17.36 g (total amount) of mixture 4 synthesized in Example 4; 2.18 g (15.81 mmol) of 2,5-dihydroxybenzaldehyde to 2.00 g (14.51 mmol); 4.80 g (47.44 mmol) of triethylamine to 4.40 g (43.53 mmol); and 5.13 g (20.56 mmol) of compound (3a) to 4.70 g (18.86 mmol). As a result, 10.83 g of polymerizable compound (IIIa) was obtained (yield: 63.8%).

Example 41

The same operation as in Example 37 was performed except that in Step 2, 17.84 g (total amount) of mixture 1 synthesized in Example 1 was changed to 18.48 g (total amount) of mixture 5 synthesized in Example 5; 2.18 g (15.81 mmol) of 2,5-dihydroxybenzaldehyde to 2.51 g (18.16 mmol); 4.80 g (47.44 mmol) of triethylamine to 5.51 g (54.49 mmol); and 5.13 g (20.56 mmol) of compound (3a) to 5.89 g (23.61 mmol). As a result, 13.50 g of polymerizable compound (IIIa) was obtained (yield: 63.5%)

Example 42

The same operation as in Example 37 was performed except that in Step 2, 17.84 g (total amount) of mixture 1 synthesized in Example 1 was changed to 17.74 g (total amount) of mixture 6 synthesized in Example 6; 2.18 g (15.81 mmol) of 2,5-dihydroxybenzaldehyde to 2.26 g (16.33 mmol); 4.80 g (47.44 mmol) of triethylamine to 4.96 g (48.99 mmol); and 5.13 g (20.56 mmol) of compound (3a) to 5.29 g (21.23 mmol). As a result, 12.14 g of polymerizable compound (IIIa) was obtained (yield: 63.5%).

Example 43

The same operation as in Example 37 was performed except that in Step 2, 17.84 g (total amount) of mixture 1 synthesized in Example 1 was changed to 17.76 g (total amount) of mixture 7 synthesized in Example 7; 2.18 g (15.81 mmol) of 2,5-dihydroxybenzaldehyde to 1.90 g (13.74 mmol); 4.80 g (47.44 mmol) of triethylamine to 4.17 g (41.22 mmol); and 5.13 g (20.56 mmol) of compound (3a) to 4.45 g (17.86 mmol). As a result, 9.96 g of polymerizable compound (IIIa) was obtained (yield: 61.9%).

Example 44

The same operation as in Example 37 was performed except that in Step 2, 17.84 g (total amount) of mixture 1 synthesized in Example 1 was changed to 16.29 g (total amount) of mixture 8 synthesized in Example 8; 2.18 g (15.81 mmol) of 2,5-dihydroxybenzaldehyde to 1.79 g (12.95 mmol); 4.80 g (47.44 mmol) of triethylamine to 3.93 g (38.85 mmol) of triethylamine; and 5.13 g (20.56 mmol) of compound (3a) to 4.20 g (16.83 mmol). As a result, 9.43 g of polymerizable compound (IIIa) was obtained (yield: 62.2%).

Example 45

The same operation as in Example 37 was performed except that in Step 2, 17.84 g (total amount) of mixture 1 synthesized in Example 1 was changed to 17.25 g (total amount) of mixture 9 synthesized in Example 9; 2.18 g (15.81 mmol) of 2,5-dihydroxybenzaldehyde to 1.96 g (14.19 mmol); 4.80 g (47.44 mmol) of triethylamine to 4.31 g (42.56 mmol); and 5.13 g (20.56 mmol) of compound (3a) to 4.60 g (18.44 mmol). As a result, 10.04 g of polymerizable compound (IIIa) was obtained (yield: 60.5%).

Example 46

The same operation as in Example 37 was performed except that in Step 2, 17.84 g (total amount) of mixture 1 synthesized in Example 1 was changed to 17.73 g (total amount) of mixture 10 synthesized in Example 10; 2.18 g (15.81 mmol) of 2,5-dihydroxybenzaldehyde to 1.99 g (14.38 mmol); 4.80 g (47.44 mmol) of triethylamine to 4.36 g (43.13 mmol); and 5.13 g (20.56 mmol) of compound (3a) to 4.66 g (18.69 mmol). As a result, 10.28 g of polymerizable compound (IIIa) was obtained (yield: 61.1%).

Example 47

The same operation as in Example 37 was performed except that in Step 2, 17.84 g (total amount) of mixture 1 synthesized in Example 1 was changed to 17.04 g (total amount) of mixture 11 synthesized in Example 11; 2.18 g (15.81 mmol) of 2,5-dihydroxybenzaldehyde to 2.07 g (14.97 mmol); 4.80 g (47.44 mmol) of triethylamine to 4.54 g (44.90 mmol); and 5.13 g (20.56 mmol) of compound (3a) to 4.85 g (19.46 mmol). As a result, 10.68 g of polymerizable compound (IIIa) was obtained (yield: 60.9%).

Example 48

The same operation as in Example 37 was performed except that in Step 2, 17.84 g (total amount) of mixture 1 synthesized in Example 1 was changed to 16.91 g (total amount) of mixture 12 synthesized in Example 12; 2.18 g (15.81 mmol) of 2,5-dihydroxybenzaldehyde to 2.31 g (16.70 mmol); 4.80 g (47.44 mmol) of triethylamine to 5.07 g (50.11 mmol); and 5.13 g (20.56 mmol) of compound (3a) to 5.41 g (21.71 mmol). As a result, 12.10 g of polymerizable compound (IIIa) was obtained (yield: 61.9%).

Example 49

The same operation as in Example 37 was performed except that in Step 2, 17.84 g (total amount) of mixture 1 synthesized in Example 1 was changed to 17.31 g (total amount) of mixture 13 synthesized in Example 13; 2.18 g (15.81 mmol) of 2,5-dihydroxybenzaldehyde to 2.19 g (15.89 mmol); 4.80 g (47.44 mmol) of triethylamine to 4.82 g (47.66 mmol); and 5.13 g (20.56 mmol) of compound (3a) to 5.15 g (20.65 mmol). As a result, 11.40 g of polymerizable compound (IIIa) was obtained (yield: 61.3%).

Example 50

The same operation as in Example 37 was performed except that in Step 2, 17.84 g (total amount) of mixture 1 synthesized in Example 1 was changed to 17.96 g (total amount) of mixture 14 synthesized in Example 14; 2.18 g (15.81 mmol) of 2,5-dihydroxybenzaldehyde to 2.15 g (15.57 mmol); 4.80 g (47.44 mmol) of triethylamine to 4.73 g (46.71 mmol); and 5.13 g (20.56 mmol) of compound (3a) to 5.05 g (20.24 mmol). As a result, 11.21 g of polymerizable compound (IIIa) was obtained (yield: 61.5%).

Example 51

The same operation as in Example 37 was performed except that in Step 2, 17.84 g (total amount) of mixture 1 synthesized in Example 1 was changed to 17.56 g (total amount) of mixture 15 synthesized in Example 15; 2.18 g (15.81 mmol) of 2,5-dihydroxybenzaldehyde to 2.12 g (15.32 mmol); 4.80 g (47.44 mmol) of triethylamine to 4.65 g (45.97 mmol); and 5.13 g (20.56 mmol) of compound (3a) to 4.97 g (19.92 mmol). As a result, 11.13 g of polymerizable compound (IIIa) was obtained (yield: 62.0%).

Example 52

The same operation as in Example 37 was performed except that in Step 2, 17.84 g (total amount) of mixture 1 synthesized in Example 1 was changed to 17.84 g (total amount) of mixture 16 synthesized in Example 16; 2.18 g (15.81 mmol) of 2,5-dihydroxybenzaldehyde to 2.04 g (14.77 mmol); 4.80 g (47.44 mmol) of triethylamine to 4.48 g (44.32 mmol); and 5.13 g (20.56 mmol) of compound (3a) to 4.79 g (19.20 mmol). As a result, 10.38 g of polymerizable compound (IIIa) was obtained (yield: 60.0%).

Example 53

The same operation as in Example 37 was performed except that in Step 2, 17.84 g (total amount) of mixture 1 synthesized in Example 1 was changed to 17.93 g (total amount) of mixture 17 synthesized in Example 17; 2.18 g (15.81 mmol) of 2,5-dihydroxybenzaldehyde to 2.17 g (15.70 mmol); 4.80 g (47.44 mmol) of triethylamine to 4.77 g (47.10 mmol); and 5.13 g (20.56 mmol) of compound (3a) to 5.09 g (20.41 mmol). As a result, 12.33 g of polymerizable compound (IIIa) was obtained (yield: 67.1%).

Example 54

The same operation as in Example 37 was performed except that in Step 2, 17.84 g (total amount) of mixture 1 synthesized in Example 1 was changed to 18.01 g (total amount) of mixture 18 synthesized in Example 18; 2.18 g (15.81 mmol) of 2,5-dihydroxybenzaldehyde to 2.14 g (15.52 mmol); 4.80 g (47.44 mmol) of triethylamine to 4.71 g (46.56 mmol); and 5.13 g (20.56 mmol) of compound (3a) to 5.03 g (20.18 mmol). As a result, 12.14 g of polymerizable compound (IIIa) was obtained (yield: 66.8%).

Example 55

The same operation as in Example 37 was performed except that in Step 2, 17.84 g (total amount) of mixture 1 synthesized in Example 1 was changed to 17.79 g (total amount) of mixture 19 synthesized in Example 19; 2.18 g (15.81 mmol) of 2,5-dihydroxybenzaldehyde to 2.08 g (15.07 mmol); 4.80 g (47.44 mmol) of triethylamine to 4.58 g (45.22 mmol); and 5.13 g (20.56 mmol) of compound (3a) to 4.89 g (19.59 mmol). As a result, 11.68 g of polymerizable compound (IIIa) was obtained (yield: 66.2%).

Example 56

The same operation as in Example 37 was performed except that in Step 2, 17.84 g (total amount) of mixture 1 synthesized in Example 1 was changed to 17.45 g (total amount) of mixture 20 synthesized in Example 20; 2.18 g (15.81 mmol) of 2,5-dihydroxybenzaldehyde to 1.98 g (14.34 mmol); 4.80 g (47.44 mmol) of triethylamine to 4.35 g (43.02 mmol); and 5.13 g (20.56 mmol) of compound (3a) to 4.65 g (18.64 mmol). As a result, 11.50 g of polymerizable compound (IIIa) was obtained (yield: 68.5%).

Example 57

The same operation as in Example 37 was performed except that in Step 2, 17.84 g (total amount) of mixture 1 synthesized in Example 1 was changed to 18.59 g (total amount) of mixture 21 synthesized in Example 21; 2.18 g (15.81 mmol) of 2,5-dihydroxybenzaldehyde to 2.51 g (18.14 mmol); 4.80 g (47.44 mmol) of triethylamine to 5.51 g (54.43 mmol); and 5.13 g (20.56 mmol) of compound (3a) to 5.88 g (23.59 mmol). As a result, 14.49 g of polymerizable compound (IIIa) was obtained (yield: 68.2%).

Example 58

The same operation as in Example 37 was performed except that in Step 2, 17.84 g (total amount) of mixture 1 synthesized in Example 1 was changed to 17.84 g (total amount) of mixture 22 synthesized in Example 22; 2.18 g (15.81 mmol) of 2,5-dihydroxybenzaldehyde to 2.24 g (16.23 mmol); 4.80 g (47.44 mmol) of triethylamine to 4.93 g (48.70 mmol); and 5.13 g (20.56 mmol) of compound (3a) to 5.26 g (21.10 mmol). As a result, 12.96 g of polymerizable compound (IIIa) was obtained (yield: 68.23%).

Example 59

The same operation as in Example 37 was performed except that in Step 2, 17.84 g (total amount) of mixture 1 synthesized in Example 1 was changed to 17.84 g (total amount) of mixture 23 synthesized in Example 23; 2.18 g (15.81 mmol) of 2,5-dihydroxybenzaldehyde to 1.87 g (13.55 mmol); 4.80 g (47.44 mmol) of triethylamine to 4.11 g (40.65 mmol); and 5.13 g (20.56 mmol) of compound (3a) to 4.39 g (17.62 mmol). As a result, 10.55 g of polymerizable compound (IIIa) was obtained (yield: 66.5%).

Example 60

The same operation as in Example 37 was performed except that in Step 2, 17.84 g (total amount) of mixture 1 synthesized in Example 1 was changed to 16.36 g (total amount) of mixture 24 synthesized in Example 24; 2.18 g (15.81 mmol) of 2,5-dihydroxybenzaldehyde to 1.76 g (12.71 mmol); 4.80 g (47.44 mmol) of triethylamine to 3.86 g (38.12 mmol); and 5.13 g (20.56 mmol) of compound (3a) to 4.12 g (16.52 mmol). As a result, 9.94 g of polymerizable compound (IIIa) was obtained (yield: 66.8%).

Example 61

The same operation as in Example 37 was performed except that in Step 2, 17.84 g (total amount) of mixture 1 synthesized in Example 1 was changed to 17.33 g (total amount) of mixture 25 synthesized in Example 25; 2.18 g (15.81 mmol) of 2,5-dihydroxybenzaldehyde to 1.93 g (14.00 mmol); 4.80 g (47.44 mmol) of triethylamine to 4.25 g (42.01 mmol); and 5.13 g (20.56 mmol) of compound (3a) to 4.54 g (18.20 mmol). As a result, 10.42 g of polymerizable compound (IIIa) was obtained (yield: 63.5%).

Example 62

The same operation as in Example 37 was performed except that in Step 2, 17.84 g (total amount) of mixture 1 synthesized in Example 1 was changed to 17.81 g (total amount) of mixture 26 synthesized in Example 26; 2.18 g (15.81 mmol) of 2,5-dihydroxybenzaldehyde to 1.96 g (14.21 mmol); 4.80 g (47.44 mmol) of triethylamine to 4.31 g (42.63 mmol); and 5.13 g (20.56 mmol) of compound (3a) to 4.61 g (18.47 mmol). As a result, 10.92 g of polymerizable compound (IIIa) was obtained (yield: 65.7%).

Example 63

The same operation as in Example 37 was performed except that in Step 2, 17.84 g (total amount) of mixture 1 synthesized in Example 1 was changed to 17.13 g (total amount) of mixture 27 synthesized in Example 27; 2.18 g (15.81 mmol) of 2,5-dihydroxybenzaldehyde to 2.05 g (14.81 mmol); 4.80 g (47.44 mmol) of triethylamine to 4.50 g (44.43 mmol); and 5.13 g (20.56 mmol) of compound (3a) to 4.80 g (19.25 mmol). As a result, 11.35 g of polymerizable compound (IIIa) was obtained (yield: 65.5%).

Example 64

The same operation as in Example 37 was performed except that in Step 2, 17.84 g (total amount) of mixture 1 synthesized in Example 1 was changed to 17.00 g (total amount) of mixture 28 synthesized in Example 28; 2.18 g (15.81 mmol) of 2,5-dihydroxybenzaldehyde to 2.29 g (16.61 mmol); 4.80 g (47.44 mmol) of triethylamine to 5.04 g (49.82 mmol); and 5.13 g (20.56 mmol) of compound (3a) to 5.38 g (17.70 mmol). As a result, 12.92 g of polymerizable compound (IIIa) was obtained (yield: 66.5%).

Example 65

The same operation as in Example 37 was performed except that in Step 2, 17.84 g (total amount) of mixture 1 synthesized in Example 1 was changed to 17.40 g (total amount) of mixture 29 synthesized in Example 29; 2.18 g (15.81 mmol) of 2,5-dihydroxybenzaldehyde to 2.18 g (15.77 mmol); 4.80 g (47.44 mmol) of triethylamine to 4.79 g (47.30 mmol); and 5.13 g (20.56 mmol) of compound (3a) to 5.11 g (20.50 mmol). As a result, 12.15 g of polymerizable compound (IIIa) was obtained (yield: 65.8%).

Example 66

The same operation as in Example 37 was performed except that in Step 2, 17.84 g (total amount) of mixture 1 synthesized in Example 1 was changed to 18.05 g (total amount) of mixture 30 synthesized in Example 30; 2.18 g (15.81 mmol) of 2,5-dihydroxybenzaldehyde to 2.13 g (15.45 mmol); 4.80 g (47.44 mmol) of triethylamine to 4.69 g (46.34 mmol); and 5.13 g (20.56 mmol) of compound (3a) to 5.01 g (20.08 mmol). As a result, 11.94 g of polymerizable compound (IIIa) was obtained (yield: 66.1%).

Example 67

The same operation as in Example 37 was performed except that in Step 2, 17.84 g (total amount) of mixture 1 synthesized in Example 1 was changed to 17.65 g (total amount) of mixture 31 synthesized in Example 31; 2.18 g (15.81 mmol) of 2,5-dihydroxybenzaldehyde to 2.10 g (15.19 mmol); 4.80 g (47.44 mmol) of triethylamine to 4.61 g (45.56 mmol); and 5.13 g (20.56 mmol) of compound (3a) to 4.92 g (19.74 mmol). As a result, 11.85 g of polymerizable compound (IIIa) was obtained (yield: 66.6%).

Example 68

The same operation as in Example 37 was performed except that in Step 2, 17.84 g (total amount) of mixture 1 synthesized in Example 1 was changed to 17.93 g (total amount) of mixture 32 synthesized in Example 32; 2.18 g (15.81 mmol) of 2,5-dihydroxybenzaldehyde to 2.02 g (14.62 mmol); 4.80 g (47.44 mmol) of triethylamine to 4.44 g (43.86 mmol); and 5.13 g (20.56 mmol) of compound (3a) to 4.74 g (19.01 mmol). As a result, 11.03 g of polymerizable compound (IIIa) was obtained (yield: 64.5%).

Example 69

The same operation as in Example 37 was performed except that in Step 2, 17.84 g (total amount) of mixture 1 synthesized in Example 1 was changed to 14.34 g (total amount) of mixture 33 synthesized in Example 33; 2.18 g (15.81 mmol) of 2,5-dihydroxybenzaldehyde to 2.17 g (15.70 mmol); 4.80 g (47.44 mmol) of triethylamine to 4.77 g (47.10 mmol); and 5.13 g (20.56 mmol) of compound (3a) to 5.09 g (20.41 mmol). As a result, 12.63 g of polymerizable compound (IIIa) was obtained (yield: 68.8%).

Example 70

The same operation as in Example 37 was performed except that in Step 2, 17.84 g (total amount) of mixture 1 synthesized in Example 1 was changed to 16.04 g (total amount) of mixture 34 synthesized in Example 34; 2.18 g (15.81 mmol) of 2,5-dihydroxybenzaldehyde to 2.51 g (18.14 mmol); 4.80 g (47.44 mmol) of triethylamine to 5.51 g (54.43 mmol); and 5.13 g (20.56 mmol) of compound (3a) to 5.88 g (23.59 mmol). As a result, 14.56 g of polymerizable compound (IIIa) was obtained (yield: 68.5%).

Example 71

The same operation as in Example 37 was performed except that in Step 2, 17.84 g (total amount) of mixture 1 synthesized in Example 1 was changed to 17.40 g (total amount) of mixture 35 synthesized in Example 35; 2.18 g (15.81 mmol) of 2,5-dihydroxybenzaldehyde to 2.18 g (15.77 mmol); 4.80 g (47.44 mmol) of triethylamine to 4.79 g (47.30 mmol); and 5.13 g (20.56 mmol) of compound (3a) to 5.11 g (20.50 mmol). As a result, 12.15 g of polymerizable compound (IIIa) was obtained (yield: 65.8%).

Example 72

The same operation as in Example 37 was performed except that in Step 2, 17.84 g (total amount) of mixture 1 synthesized in Example 1 was changed to 16.78 g (total amount) of mixture 36 synthesized in Example 36; 2.18 g (15.81 mmol) of 2,5-dihydroxybenzaldehyde to 1.72 g (12.48 mmol); 4.80 g (47.44 mmol) of triethylamine to 7.58 g (74.88 mmol); and 5.13 g (20.56 mmol) of compound (3a) to 4.05 g (16.22 mmol). As a result, 12.02 g of polymerizable compound (IIIa) was obtained (yield: 82.3%).

(Example 73) Synthesis of Polymerizable Compound (IIIa)

Step 1: Synthesis of Mixture 37

A three-necked reactor equipped with a thermometer was charged with 10.0 g (47.83 mmol) of trans-1,4-cyclohexanedicarboxylic acid dichloride, 84 ml of CPME and 31 ml of THF under a nitrogen stream. To the reactor was added 12.04 g (45.55 mmol) of 4-(6-acryloyloxy-hex-1-yloxy) phenol (manufactured by DKSH). The reactor was immersed in an ice bath to lower the internal temperature of the reaction solution to 0° C. 4.83 g (47.83 mmol) of triethylamine was slowly added dropwise over 5 minutes while keeping the internal temperature of the reaction solution at 10° C. or below. After completion of the dropwise addition, stirring was further performed for 1 hour while keeping the temperature of the whole mass to 10° C. or below.

To the obtained reaction solution was added 30 ml of distilled water. After heating the reaction solution to 50° C., the reaction solution was washed for 2 hours (for hydrolysis reaction) and the aqueous layer was withdrawn. Further, after newly adding 30 ml of distilled water to the obtained organic layer, the whole mass was washed at 50° C. for 2 hours (for hydrolysis reaction), and the aqueous layer was withdrawn. After cooling the obtained organic layer to 40° C., 50 g of a 1 mol/L buffer solution (pH 5.5) consisting of acetic acid and sodium acetate was further added and stirred for washing. This washing operation with a buffer solution was performed 5 times in total. The obtained organic layer was further washed with 30 ml of distilled water, and the aqueous layer was withdrawn.

To the obtained organic layer was added 214 ml of n-hexane at 40° C., and then cooled to 0° C. to precipitate crystals. The precipitated crystals were collected by filtration. The residues were washed with n-hexane and dried under vacuum to afford 16.78 g of mixture 37 as a white solid.

The obtained crystals were analyzed by HPLC and monoester and diester were quantitated using a calibration curve. It was confirmed that the crystals contained 11.49 g (27.45 mmol) of the target monoester and 5.29 g (7.96 mmol) of diester. Further, the obtained crystals were analyzed by $^{13}$C-NMR (DMF-d7) to calculate the content of cyclohexanedicarboxylic acid and it was confirmed that cyclohexanedicarboxylic acid was below detection limit. The molar proportions of the components calculated based on their compositional ratios were monoester: 77.52 mol % and diester: 22.48 mol %.

Step 2: Synthesis of Polymerizable Compound (IIIa)

A three-necked reactor equipped with a thermometer was charged with 16.78 g (total amount) of mixture 37 synthesized in Step 1 above, 115 g of chloroform and 4.0 g of DMF under a nitrogen stream, followed by cooling to 10° C. or lower. 3.76 g (31.57 mmol) of thionyl chloride was added dropwise while controlling the reaction temperature to 10° C. or lower. After completion of the dropwise addition, the temperature of the reaction solution was raised back to 25° C. and stirring was performed for 1 hour. After completion of the reaction, the reaction solution was concentrated to quarter of its volume on an evaporator. 28.7 g of chloroform was then added to afford a chloroform solution.

Separately, 1.72 g (12.48 mmol) of 2,5-dihydroxybenzaldehyde and 7.58 g (74.88 mmol) of triethylamine were dissolved in 57 g of chloroform under a nitrogen stream in a three-necked reactor equipped with a thermometer, followed by cooling to 10° C. or below. To this solution was slowly added dropwise the chloroform solution prepared above while keeping the internal temperature of the reaction solution at 10° C. or below. After completion of the dropwise addition, reaction was further effected for 1 hour while keeping the temperature of the reaction solution at 10° C. or below.

After completion of the reaction, 4.05 g (16.22 mmol) of compound (3a) synthesized in Example 37 above was added to the reaction solution while keeping the temperature at 10° C. or below, followed by addition of 45 g of 1.0N hydrochloric acid aqueous solution. The reaction solution was then heated to 40° C. and reacted for 3 hours. After completion of the reaction, the reaction solution was cooled to 25° C., and liquid separation was performed.

0.57 g of ROKAHELP #479 (Mitsui Mining & Smelting Co., Ltd.) was added to the obtained organic layer, and after stirring for 30 minutes, ROKAHELP #479 was filtered off. The reaction solution was then concentrated by withdrawing about 80% of its total weight on an evaporator. To this solution was added 23 g of THF and the mixture was stirred for 1 hour. Next, 92 g of n-hexane was added dropwise to this solution and then cooled to 0° C. to precipitate crystals. Thereafter, the precipitated crystals were collected by filtration.

To the obtained crystals were added 120 g of THF, 2.1 g of ROKAHELP #479 and 110 mg of 2,6-di-t-butyl-4-methylphenol, and after stirring for 30 minutes, ROKAHELP #479 was filtered off. Subsequently, 40 g of THF was distilled off from the obtained reaction solution on an evaporator. 134 g of methanol was added dropwise to the obtained solution, and the solution was cooled to 0° C. to precipitate crystals. The precipitated crystals were collected by filtration. The residues were washed with methanol and dried under vacuum to afford 12.02 g of polymerizable compound (IIIa) (yield: 82.3%).

(Comparative Example 6) Synthesis of Polymerizable Compound (IIIa)

Step 1: Synthesis of Compound (3a)

Compound (3a) was synthesized in the same manner as in Step 1 of Example 37.

Step 2: Production of Polymerizable Compound (IIIa)

A three-necked reactor equipped with a thermometer was charged with 19.96 g (total amount) of mixture A synthesized in Comparative Example 1, 150 g of toluene and 1.5 g of DMF under a nitrogen stream, followed by cooling to 10° C. or lower. 5.94 g (50.0 mmol) of thionyl chloride was added dropwise while controlling the reaction temperature to 10° C. or lower. After completion of the dropwise addition, the temperature of the reaction solution was raised back to 25° C. and stirring was performed for 1 hour. After completion of the reaction, the reaction solution was concentrated to half of its volume on an evaporator, toluene was added to compensate for the volume lost during concentration, and the reaction solution was again concentrated to half of its volume on the evaporator. This series of operations was repeated 5 times to afford a toluene solution.

Separately, 3.79 g (27.46 mmol) of 2,5-dihydroxybenzaldehyde and 8.33 g (82.37 mmol) of triethylamine were dissolved in 80 g of THF under a nitrogen stream in a three-necked reactor equipped with a thermometer, followed by cooling of the whole mass to 10° C. or below. To this solution was slowly added dropwise the toluene solution prepared above while keeping the reaction temperature at 10° C. or below. After completion of the dropwise addition, the whole mass was further stirred for 1 hour at 10° C. or below. The reaction solution became creamy due to precipitation of a hydrochloride salt of triethylamine produced by the reaction. After completion of the reaction, 8.90 g (35.69 mmol) of compound (3a) synthesized in Step 1 above was added to the reaction solution while keeping the temperature at 10° C. or below, followed by addition of 20 g of 1.0N hydrochloric acid aqueous solution. The reaction solution was then heated to 40° C. and reacted for 5 hours. The hydrochloride salt of triethylamine which had precipitated upon heating to 40° C. was dissolved, forming a clear two-layered solution of toluene and water. When the reaction solution was cooled to 25° C. after completion of the reaction, components insoluble both in toluene and water were abundantly observed. 300 g of ethyl acetate and 150 g of 10 wt % salt water were added for liquid separation. The obtained organic layer was further washed twice with 150 g of 2 wt % salt water. The performance of this liquid separation was so poor that an intermediate layer was produced. The intermediate layer was discarded together with the insoluble components. The organic layer was separated, and a volume of low-volatile component (solvent), corresponding to about 15% of total volume, was withdrawn from the obtained organic layer on an evaporator. Upon concentration, insoluble components precipitated again. Thus the concentrate was filtered using a filter aid (ROKAHELP #479, Mitsui Mining & Smelting Co., Ltd.). The obtained filtrate was brought to a temperature of 25° C. and a mixed solvent of 150 g methanol and 40 g water was slowly added dropwise thereto. The solution was then cooled to 10° C. to precipitate crystals and the precipitated crystals were collected by filtration. Further, 40 g of THF, 40 g of methanol and 10 mg of 2,6-di-tert-butyl-4-methylphenol were added to the crystals and the whole mass was heated to 50° C. to afford a homogenous solution. The solution was subjected to hot filtration at 50° C. The obtained filtrate was slowly cooled to 10° C. for recrystallization. The obtained crystals were isolated by filtration and dried using a vacuum dryer to afford 3.62 g of polymerizable compound (IIIa) (yield: 11.3%).

The structure of the target product was identified by $^1$H-NMR.

Comparative Example 7

The same operation as in Comparative Example 6 was performed except that in Step 2, 19.96 g (total amount) of mixture A synthesized in Comparative Example 1 was changed to 19.95 g (total amount) of mixture B synthesized in Comparative Example 2; 3.79 g (27.46 mmol) of 2,5-dihydroxybenzaldehyde to 3.60 g (26.06 mmol); 8.33 g (82.37 mmol) of triethylamine to 7.91 g (78.17 mmol); and 8.90 g (35.69 mmol) of compound (3a) to 8.45 g (33.87 mmol). As a result, 4.46 g of polymerizable compound (IIIa) was obtained (yield: 14.6%).

Comparative Example 8

The same operation as in Comparative Example 6 was performed except that in Step 2, 19.96 g (total amount) of mixture A synthesized in Comparative Example 1 was changed to 20.46 g (total amount) of mixture C synthesized in Comparative Example 3; 3.79 g (27.46 mmol) of 2,5-dihydroxybenzaldehyde to 4.32 g (31.25 mmol); 8.33 g (82.37 mmol) of triethylamine to 9.49 g (93.75 mmol); and 8.90 g (35.69 mmol) of compound (3a) to 10.13 g (40.62 mmol). As a result, 1.66 g of polymerizable compound (IIIa) was obtained (yield: 4.5%).

Comparative Example 9

The same operation as in Comparative Example 6 was performed except that in Step 2, 19.96 g (total amount) of mixture A synthesized in Comparative Example 1 was changed to 20.59 g (total amount) of mixture D synthesized in Comparative Example 4; 3.79 g (27.46 mmol) of 2,5-dihydroxybenzaldehyde to 4.05 g (29.32 mmol); 8.33 g (82.37 mmol) of triethylamine to 8.90 g (87.95 mmol); and 8.90 g (35.69 mmol) of compound (3a) to 9.50 g (38.11 mmol). As a result, 2.15 g of polymerizable compound (IIIa) was obtained (yield: 6.3%).

(Comparative Example 10) Synthesis of Polymerizable Compound (IIIa)

The same operation as in Example 73 was performed except that in Step 2, 16.78 g (total amount) of mixture 37 synthesized in Step 1 of Example 73 was changed to 18.72 g (total amount) of mixture E synthesized in Comparative Example 5. As a result, 0.98 g of polymerizable compound (IIIa) was obtained (yield: 6.71%).

(Comparative Example 11) Synthesis of Polymerizable Compound (IIIa)

Step 1: Synthesis of Mixture F

A three-necked reactor equipped with a thermometer was charged with 10.0 g (47.83 mmol) of trans-1,4-cyclohexanedicarboxylic acid dichloride, 84 ml of CPME and 31 ml of THF under a nitrogen stream. To the reactor was added 12.04 g (45.55 mmol) of 4-(6-acryloyloxy-hex-1-yloxy) phenol (manufactured by DKSH). The reactor was immersed in an ice bath to lower the internal temperature of the reaction solution to 0° C. 4.83 g (47.83 mmol) of triethylamine was slowly added dropwise over 5 minutes while keeping the internal temperature of the reaction solution at 10° C. or below. After completion of the dropwise addition, stirring was further performed for 1 hour while keeping the temperature of the whole mass to 10° C. or below.

To the obtained reaction solution was added 30 ml of distilled water. After heating the reaction solution to 50° C., the reaction solution was washed for 2 hours (for hydrolysis reaction) and the aqueous layer was withdrawn. Further, after newly adding 30 ml of distilled water to the obtained organic layer, the whole mass was washed at 50° C. for 2 hours (for hydrolysis reaction), and the aqueous layer was withdrawn. After cooling the obtained organic layer to 40° C., 214 ml of n-hexane was added at 40° C., and then the organic layer was cooled to 0° C. to precipitate crystals. The precipitated crystals were collected by filtration. The residues were washed with n-hexane and dried under vacuum to afford 18.72 g of mixture F as a white solid.

The obtained crystals were analyzed by HPLC and monoester and diester were quantitated using a calibration curve. It was confirmed that the crystals contained 11.50 g (27.48 mmol) of the target monoester and 5.30 g (7.97 mmol) of diester. Further, the obtained crystals were analyzed by $^{13}$C-NMR (DMF-d7) and it was confirmed that the crystals contained 1.92 g (11.56 mmol) of cyclohexanedicarboxylic acid. The molar proportions of the components calculated based on their compositional ratios were monoester: 58.46 mol %, diester: 16.95 mol %, and cyclohexanedicarboxylic acid: 24.59 mol %.

Step 2: Synthesis of Polymerizable Compound (IIIa)

A three-necked reactor equipped with a thermometer was charged with 18.72 g (total amount) of mixture F synthesized in Step 1 above, 115 g of chloroform and 4.0 g of DMF under a nitrogen stream, followed by cooling to 10° C. or lower. 6.92 g (58.19 mmol) of thionyl chloride was added dropwise while controlling the reaction temperature to 10° C. or lower. After completion of the dropwise addition, the temperature of the reaction solution was raised back to 25° C. and stirring was performed for 1 hour. After completion of the reaction, the reaction solution was concentrated to quarter of its volume on an evaporator. 28.7 g of chloroform was then added to afford a chloroform solution.

Separately, 1.72 g (12.48 mmol) of 2,5-dihydroxybenzaldehyde and 7.58 g (74.88 mmol) of triethylamine were dissolved in 57 g of chloroform under a nitrogen stream in a three-necked reactor equipped with a thermometer, followed by cooling to 10° C. or below. To this solution was slowly added dropwise the chloroform solution prepared above while keeping the internal temperature of the reaction solution at 10° C. or below. After completion of the dropwise addition, reaction was further effected for 1 hour while keeping the temperature of the reaction solution at 10° C. or below.

After completion of the reaction, 4.05 g (16.22 mmol) of compound (3a) synthesized in Example 37 above was added to the reaction solution while keeping the temperature at 10° C. or below, followed by addition of 45 g of 1.0N hydrochloric acid aqueous solution. The reaction solution was then heated to 40° C. and reacted for 3 hours. After completion of the reaction, the reaction solution was cooled to 25° C., and liquid separation was performed.

0.57 g of ROKAHELP #479 (Mitsui Mining & Smelting Co., Ltd.) was added to the obtained organic layer, and after stirring for 30 minutes, ROKAHELP #479 was filtered off. The reaction solution was then concentrated by withdrawing about 80% of its total weight on an evaporator. To this solution was added 23 g of THF and the mixture was stirred for 1 hour. Next, 92 g of n-hexane was added dropwise to this solution and then cooled to 0° C. to precipitate crystals. Thereafter, the precipitated crystals were collected by filtration.

To the obtained crystals were added 120 g of THF, 2.1 g of ROKAHELP #479 and 110 mg of 2,6-di-t-butyl-4-methylphenol, and after stirring for 30 minutes, ROKAHELP #479 was filtered off. Subsequently, 40 g of THF was distilled off from the obtained reaction solution on an evaporator. 134 g of methanol was added dropwise to the obtained solution, and the solution was cooled to 0° C. to precipitate crystals. The precipitated crystals were collected by filtration. The residues were washed with methanol and dried under vacuum to afford 1.02 g of polymerizable compound (IIIa) (yield: 6.98%).

The above results are summarized in Tables 1 to 6 below.

In the tables, the "Hildebrand solubility parameter" of each mixed solvent was calculated following the additivity rule.

The amount of solvent used (fold by weight) was based on the weight of trans-1,4-cyclohexanedicarboxylic acid dichloride. For example, when 200 ml of CPME was used per 10 g of trans-1,4-cyclohexanedicarboxylic acid dichloride, the amount of solvent used is expressed as 20 (fold by weight) in the tables.

Reaction conversion (%) was based on 4-(6-acryloyloxyhex-1-yloxy) phenol.

Monoester selectivity (%) was determined using the following formula:

Monoester selectivity (%)=(LC-area of monoester)/[(LC-area of monoester)+(LC-area of diester)]×100 where LC-area represents an area indicated by a calibration curve of HPLC.

TABLE 1

| | Mixture | Solvent type | Solubility parameter (MPa$^{1/2}$) | Amount used (fold by weight) | Monoester selectivity (%) | Reaction Conversion (%) | Buffer solution |
|---|---|---|---|---|---|---|---|
| Ex. 1 | 1 | CPME | 17.2 | 20 | 68.53% | 98.0% | Potassium hydrogen phthalate + Sodium hydroxide |
| Ex. 2 | 2 | THF | 18.6 | 15 | 67.28% | 98.7% | |
| Ex. 3 | 3 | MTBE | 15.6 | 20 | 65.94% | 97.8% | |
| Ex. 4 | 4 | Diethyl ether | 15.1 | 20 | 63.65% | 96.4% | |
| Ex. 5 | 5 | Dibutyl ether | 14.9 | 30 | 77.99% | 99.5% | |
| Ex. 6 | 6 | Diisopropyl ether | 14.1 | 30 | 71.72% | 96.8% | |
| Ex. 7 | 7 | 1,2-Dimethoxyethane | 19.2 | 20 | 58.09% | 99.8% | |
| Ex. 8 | 8 | 2-Butanone | 19.0 | 20 | 59.61% | 91.2% | |
| Ex. 9 | 9 | Chloroform | 19.0 | 20 | 62.40% | 96.0% | |
| Ex. 10 | 10 | Ethyl acetate | 18.6 | 20 | 61.46% | 98.9% | |
| Ex. 11 | 11 | Toluene | 18.2 | 20 | 67.54% | 93.8% | |
| Ex. 12 | 12 | Cyclohexane + THF | 17.4 | 13 + 7 | 78.06% | 91.0% | |
| Ex. 13 | 13 | Cyclohexane + CPME | 17.0 | 10 + 15 | 71.38% | 94.5% | |
| Ex. 14 | 14 | Dibutyl ether + CPME | 16.1 | 10 + 10 | 66.71% | 99.1% | |
| Ex. 15 | 15 | Dibutyl ether + Toluene | 15.7 | 15 + 5 | 67.14% | 96.8% | |
| Ex. 16 | 16 | CPME + Toluene | 17.5 | 15 + 5 | 63.05% | 99.2% | |
| Ex. 17 | 17 | CPME | 17.2 | 20 | 68.53% | 98.0% | Sodium acetate + Acetic acid |
| Ex. 18 | 18 | THF | 18.6 | 15 | 67.28% | 98.7% | |
| Ex. 19 | 19 | MTBE | 15.6 | 20 | 65.94% | 97.8% | |
| Ex. 20 | 20 | Diethyl ether | 15.1 | 20 | 63.65% | 96.4% | |

TABLE 2

| | Mixture | Solvent type | Solubility parameter (MPa$^{1/2}$) | Amount used (fold by weight) | Monoester selectivity (%) | Reaction Conversion (%) | Buffer solution |
|---|---|---|---|---|---|---|---|
| Ex. 21 | 21 | Dibutyl ether | 14.9 | 30 | 77.99% | 99.5% | Sodium acetate + Acetic acid |
| Ex. 22 | 22 | Diisopropyl ether | 14.1 | 30 | 71.72% | 96.8% | |
| Ex. 23 | 23 | 1,2-Dimethoxyethane | 19.2 | 20 | 58.09% | 99.8% | |
| Ex. 24 | 24 | 2-Butanone | 19.0 | 20 | 59.61% | 91.2% | |
| Ex. 25 | 25 | Chloroform | 19.0 | 20 | 62.40% | 96.0% | |
| Ex. 26 | 26 | Ethyl acetate | 18.6 | 20 | 61.46% | 98.9% | |
| Ex. 27 | 27 | Toluene | 18.2 | 20 | 67.54% | 93.8% | |
| Ex. 28 | 28 | Cyclohexane + THF | 17.4 | 13 + 7 | 78.06% | 91.0% | |
| Ex. 29 | 29 | Cyclohexane + CPME | 17.0 | 10 + 15 | 71.38% | 94.5% | |
| Ex. 30 | 30 | Dibutyl ether + CPME | 16.1 | 10 + 10 | 66.71% | 99.1% | |
| Ex. 31 | 31 | Dibutyl ether + Toluene | 15.7 | 15 + 5 | 67.14% | 96.8% | |
| Ex. 32 | 32 | CPME + Toluene | 17.5 | 15 + 5 | 63.05% | 99.2% | |
| Ex. 33 | 33 | CPME | 17.2 | 20 | 68.53% | 98.0% | |
| Ex. 34 | 34 | Dibutyl ether | 14.9 | 30 | 77.99% | 99.5% | |
| Ex. 35 | 35 | NMP | 23.1 | 30 | 68.52% | 98.0% | |
| Ex. 36 | 36 | CPME +THE | 17.6 | 8.4 + 3.1 | 63.29% | 98.0% | |
| Comp. Ex. 1 | A | CPME | 17.2 | 20 | 68.53% | 98.0% | No buffer solution used |
| Comp. Ex. 2 | B | Dibutyl ether | 14.9 | 30 | 77.99% | 99.5% | |
| Comp. Ex. 3 | C | NMP | 23.1 | 10 | 36.76% | 97.0% | |

TABLE 2-continued

| | Mixture | Solvent type | Solubility parameter (MPa$^{1/2}$) | Amount used (fold by weight) | Monoester selectivity (%) | Reaction Conversion (%) | Buffer solution |
|---|---|---|---|---|---|---|---|
| Comp. Ex. 4 | D | -Butyrolactone | 25.8 | 10 | 49.26% | 100.0% | |
| Comp. Ex. 5 | E | CPME + THF | 17.6 | 8.4 + 3.1 | 63.29% | 98.0% | |
| Comp. Ex 11 | F | CPME + THF | 17.6 | 8.4 + 3.1 | 63.29% | 98.0% | |

TABLE 3

| | Mixture | Acquired amounts of mixture components (g) | | | | Proportions of mixture components (mol %) | | |
|---|---|---|---|---|---|---|---|---|
| | | Monoester | Diester | Cyclohexane dicarboxylic acid | Total | Monoester | Diester | Cyclohexane dicarboxylic acid |
| Ex. 1 | 1 | 13.04 | 4.76 | 0.040 | 17.84 | 80.84% | 18.56% | 0.60% |
| Ex. 2 | 2 | 12.89 | 4.98 | 0.041 | 17.91 | 79.94% | 19.44% | 0.61% |
| Ex. 3 | 3 | 12.52 | 5.14 | 0.043 | 17.70 | 78.94% | 20.39% | 0.67% |
| Ex. 4 | 4 | 11.91 | 5.40 | 0.048 | 17.36 | 77.20% | 22.05% | 0.75% |
| Ex. 5 | 5 | 15.07 | 3.38 | 0.027 | 18.48 | 87.30% | 12.32% | 0.38% |
| Ex. 6 | 6 | 13.48 | 4.22 | 0.038 | 17.74 | 83.06% | 16.37% | 0.57% |
| Ex. 7 | 7 | 11.26 | 6.45 | 0.050 | 17.76 | 72.91% | 26.30% | 0.79% |
| Ex. 8 | 8 | 10.56 | 5.68 | 0.058 | 16.29 | 73.96% | 25.05% | 0.99% |
| Ex. 9 | 9 | 11.63 | 5.57 | 0.050 | 17.25 | 76.24% | 22.97% | 0.79% |
| Ex. 10 | 10 | 11.80 | 5.88 | 0.047 | 17.73 | 75.57% | 23.69% | 0.74% |
| Ex. 11 | 11 | 12.30 | 4.70 | 0.046 | 17.04 | 80.04% | 19.23% | 0.73% |
| Ex. 12 | 12 | 13.79 | 3.08 | 0.038 | 16.91 | 87.17% | 12.25% | 0.59% |
| Ex. 13 | 13 | 13.10 | 4.17 | 0.041 | 17.31 | 82.77% | 16.59% | 0.63% |
| Ex. 14 | 14 | 12.83 | 5.09 | 0.041 | 17.96 | 79.54% | 19.85% | 0.62% |
| Ex. 15 | 15 | 12.61 | 4.90 | 0.043 | 17.56 | 79.80% | 19.53% | 0.67% |
| Ex. 16 | 16 | 12.14 | 5.65 | 0.045 | 17.84 | 76.80% | 22.51% | 0.69% |
| Ex. 17 | 17 | 13.14 | 4.79 | 0.000 | 17.93 | 81.33% | 18.67% | 0.00% |
| Ex. 18 | 18 | 12.99 | 5.02 | 0.000 | 18.01 | 80.44% | 19.56% | 0.00% |
| Ex. 19 | 19 | 12.61 | 5.18 | 0.000 | 17.79 | 79.47% | 20.53% | 0.00% |
| Ex. 20 | 20 | 12.00 | 5.44 | 0.000 | 17.45 | 77.79% | 22.21% | 0.00% |

TABLE 4

| | Mixture | Acquired amounts of mixture components (g) | | | | Proportions of mixture components (mol %) | | |
|---|---|---|---|---|---|---|---|---|
| | | Monoester | Diester | Cyclohexane dicarboxylic acid | Total | Monoester | Diester | Cyclohexane dicarboxylic acid |
| Ex. 21 | 21 | 15.19 | 3.40 | 0.000 | 18.59 | 87.63% | 12.37% | 0.00% |
| Ex. 22 | 22 | 13.59 | 4.25 | 0.000 | 17.84 | 83.53% | 16.47% | 0.00% |
| Ex. 23 | 23 | 11.34 | 6.50 | 0.000 | 17.84 | 73.49% | 26.51% | 0.00% |
| Ex. 24 | 24 | 10.64 | 5.72 | 0.000 | 16.36 | 74.70% | 25.30% | 0.00% |
| Ex. 25 | 25 | 11.72 | 5.61 | 0.000 | 17.33 | 76.85% | 23.15% | 0.00% |
| Ex. 26 | 26 | 11.89 | 5.92 | 0.000 | 17.81 | 76.13% | 23.87% | 0.00% |
| Ex. 27 | 27 | 12.39 | 4.73 | 0.000 | 17.13 | 80.63% | 19.37% | 0.00% |
| Ex. 28 | 28 | 13.90 | 3.10 | 0.000 | 17.00 | 87.68% | 12.32% | 0.00% |
| Ex. 29 | 29 | 13.20 | 4.20 | 0.000 | 17.40 | 83.30% | 16.70% | 0.00% |
| Ex. 30 | 30 | 12.93 | 5.12 | 0.000 | 18.05 | 80.03% | 19.97% | 0.00% |
| Ex. 31 | 31 | 12.71 | 4.94 | 0.000 | 17.65 | 80.34% | 19.66% | 0.00% |
| Ex. 32 | 32 | 12.24 | 5.70 | 0.000 | 17.93 | 77.34% | 22.66% | 0.00% |
| Ex. 33 | 33 | 13.14 | 1.20 | 0.000 | 14.34 | 94.57% | 5.43% | 0.00% |
| Ex. 34 | 34 | 15.19 | 0.85 | 0.000 | 16.04 | 96.59% | 3.41% | 0.00% |
| Ex. 35 | 35 | 13.19 | 4.81 | 0.000 | 18.00 | 81.32% | 18.68% | 0.00% |
| Ex. 36 | 36 | 11.49 | 5.29 | 0.000 | 16.78 | 77.52% | 22.48% | 0.00% |
| Comp. Ex. 1 | A | 13.14 | 4.79 | 2.024 | 19.96 | 62.34% | 14.31% | 23.34% |
| Comp. Ex. 2 | B | 15.19 | 3.40 | 1.362 | 19.95 | 73.58% | 10.38% | 16.04% |
| Comp. Ex. 3 | C | 6.98 | 9.54 | 3.945 | 20.46 | 30.92% | 26.60% | 42.48% |
| Comp. Ex. 4 | D | 9.64 | 7.89 | 3.065 | 20.59 | 43.70% | 22.51% | 33.78% |
| Comp. Ex. 5 | E | 11.50 | 5.30 | 1.920 | 18.72 | 58.46% | 16.95% | 24.59% |

TABLE 5

| | 2,5-Dihydroxybenzaldehyde | | Triethylamine | | Compound 3a | | Polymerizable compound (IIIa) | | |
|---|---|---|---|---|---|---|---|---|---|
| | mmol | g | mmol | g | mmol | g | mmol | g | yield |
| Ex. 37 | 15.81 | 2.18 | 47.44 | 4.80 | 20.56 | 5.13 | 9.88 | 11.57 | 62.5% |
| Ex. 38 | 15.64 | 2.16 | 46.92 | 4.75 | 20.33 | 5.07 | 9.73 | 11.39 | 62.2% |
| Ex. 39 | 15.21 | 2.10 | 45.63 | 4.62 | 19.77 | 4.93 | 9.37 | 10.97 | 61.6% |
| Ex. 40 | 14.51 | 2.00 | 43.53 | 4.40 | 18.86 | 4.70 | 9.25 | 10.83 | 63.8% |
| Ex. 41 | 18.16 | 2.51 | 54.49 | 5.51 | 23.61 | 5.89 | 11.53 | 13.50 | 63.5% |
| Ex. 42 | 16.33 | 2.26 | 48.99 | 4.96 | 21.23 | 5.29 | 10.37 | 12.14 | 63.5% |
| Ex. 43 | 13.74 | 1.90 | 41.22 | 4.17 | 17.86 | 4.45 | 8.51 | 9.96 | 61.9% |
| Ex. 44 | 12.95 | 1.79 | 38.85 | 3.93 | 16.83 | 4.20 | 8.06 | 9.43 | 62.2% |
| Ex. 45 | 14.19 | 1.96 | 42.56 | 4.31 | 18.44 | 4.60 | 8.58 | 10.04 | 60.5% |
| Ex. 46 | 14.38 | 1.99 | 43.13 | 4.36 | 18.69 | 4.66 | 8.79 | 10.28 | 61.1% |
| Ex. 47 | 14.97 | 2.07 | 44.90 | 4.54 | 19.46 | 4.85 | 9.12 | 10.68 | 60.9% |
| Ex. 48 | 16.70 | 2.31 | 50.11 | 5.07 | 21.71 | 5.41 | 10.34 | 12.10 | 61.9% |
| Ex. 49 | 15.89 | 2.19 | 47.66 | 4.82 | 20.65 | 5.15 | 9.74 | 11.40 | 61.3% |
| Ex. 50 | 15.57 | 2.15 | 46.71 | 4.73 | 20.24 | 5.05 | 9.57 | 11.21 | 61.5% |
| Ex. 51 | 15.32 | 2.12 | 45.97 | 4.65 | 19.92 | 4.97 | 9.51 | 11.13 | 62.0% |
| Ex. 52 | 14.77 | 2.04 | 44.32 | 4.48 | 19.20 | 4.79 | 8.87 | 10.38 | 60.0% |
| Ex. 53 | 15.70 | 2.17 | 47.10 | 4.77 | 20.41 | 5.09 | 10.54 | 12.33 | 67.1% |
| Ex. 54 | 15.52 | 2.14 | 46.56 | 4.71 | 20.18 | 5.03 | 10.37 | 12.14 | 66.8% |
| Ex. 55 | 15.07 | 2.08 | 45.22 | 4.58 | 19.59 | 4.89 | 9.98 | 11.68 | 66.2% |
| Ex. 56 | 14.34 | 1.98 | 43.02 | 4.35 | 18.64 | 4.65 | 9.82 | 11.50 | 68.5% |

TABLE 6

| | 2,5-Dihydroxybenzaldehyde | | Triethylamine | | Compound 3a | | Polymerizable compound (IIIa) | | |
|---|---|---|---|---|---|---|---|---|---|
| | mmol | g | mmol | g | mmol | g | mmol | g | Yield |
| Ex. 57 | 18.14 | 2.51 | 54.43 | 5.51 | 23.59 | 5.88 | 12.38 | 14.49 | 68.2% |
| Ex. 58 | 16.23 | 2.24 | 48.70 | 4.93 | 21.10 | 5.26 | 11.08 | 12.96 | 68.2% |
| Ex. 59 | 13.55 | 1.87 | 40.65 | 4.11 | 17.62 | 4.39 | 9.02 | 10.55 | 66.5% |
| Ex. 60 | 12.71 | 1.76 | 38.12 | 3.86 | 16.52 | 4.12 | 8.49 | 9.94 | 66.8% |
| Ex. 61 | 14.00 | 1.93 | 42.01 | 4.25 | 18.20 | 4.54 | 8.90 | 10.42 | 63.5% |
| Ex. 62 | 14.21 | 1.96 | 42.63 | 4.31 | 18.47 | 4.61 | 9.33 | 10.92 | 65.7% |
| Ex. 63 | 14.81 | 2.05 | 44.43 | 4.50 | 19.25 | 4.80 | 9.69 | 11.35 | 65.5% |
| Ex. 64 | 16.61 | 2.29 | 49.82 | 5.04 | 21.59 | 5.38 | 11.04 | 12.92 | 66.5% |
| Ex. 65 | 15.77 | 2.18 | 47.30 | 4.79 | 20.50 | 5.11 | 10.38 | 12.15 | 65.8% |
| Ex. 66 | 15.45 | 2.13 | 46.34 | 4.69 | 20.08 | 5.01 | 10.20 | 11.94 | 66.1% |
| Ex. 67 | 15.19 | 2.10 | 45.56 | 4.61 | 19.74 | 4.92 | 10.12 | 11.85 | 66.6% |
| Ex. 68 | 14.62 | 2.02 | 43.86 | 4.44 | 19.01 | 4.74 | 9.43 | 11.03 | 64.5% |
| Ex. 69 | 15.70 | 2.17 | 47.10 | 4.77 | 20.41 | 5.09 | 10.79 | 12.63 | 68.8% |
| Ex. 70 | 18.14 | 2.51 | 54.43 | 5.51 | 23.59 | 5.88 | 12.44 | 14.56 | 68.5% |
| Ex. 71 | 15.77 | 2.18 | 47.30 | 4.79 | 20.50 | 5.11 | 10.38 | 12.15 | 65.8% |
| Ex. 72 | 12.48 | 1.72 | 74.88 | 7.58 | 16.22 | 4.05 | 10.27 | 12.02 | 82.3% |
| Ex. 73 | 12.48 | 1.72 | 74.88 | 7.58 | 16.22 | 4.05 | 10.27 | 12.02 | 82.3% |
| Comp. Ex. 6 | 27.46 | 3.79 | 82.37 | 8.33 | 35.69 | 8.90 | 3.09 | 3.62 | 11.3% |
| Comp. Ex. 7 | 26.06 | 3.60 | 78.17 | 7.91 | 33.87 | 8.45 | 3.81 | 4.46 | 14.6% |
| Comp. Ex. 8 | 31.25 | 4.32 | 93.75 | 9.49 | 40.62 | 10.13 | 1.42 | 1.66 | 4.54% |
| Comp. Ex. 9 | 29.32 | 4.05 | 87.95 | 8.90 | 38.11 | 9.50 | 1.83 | 2.15 | 6.25% |
| Comp. Ex. 10 | 12.48 | 1.72 | 74.88 | 7.58 | 16.22 | 4.05 | 0.84 | 0.98 | 6.71% |
| Comp. Ex. 11 | 12.48 | 1.72 | 74.88 | 7.58 | 16.22 | 4.05 | 0.87 | 1.02 | 6.98% |

It can be seen from the results shown in Tables 1 to 6 that performing a reaction in a water-immiscible organic solvent and performing a washing step using a weakly acidic buffer solution after completion of the reaction achieves high-yield production of a mixture wherein the monoester accounts for 50 mol % or more of the entire mixture and 1,4-cyclohexanedicarboxylic acid accounts for less than 5 mol % of the entire mixture (Examples 1 to 36).

It can also be seen that the use of mixtures 1 to 36 (mixtures disclosed herein) achieves high-yield production of polymerizable compound (IIIa) (Examples 37 to 73).

On the other hand, it can be seen that mixtures A to F prepared in Comparative Examples 1 to 4 wherein 1,4-cyclohexanedicarboxylic acid content is 5 mol % or more (notably, mixtures C and D wherein monoester content is less than 50 mol %) cannot achieve high-yield production of polymerizable compound (IIIa) (Comparative Examples 6 to 11).

(Example 74) Synthesis of Polymerizable Compound (IIIb)

Polymerizable compound (IIIb)

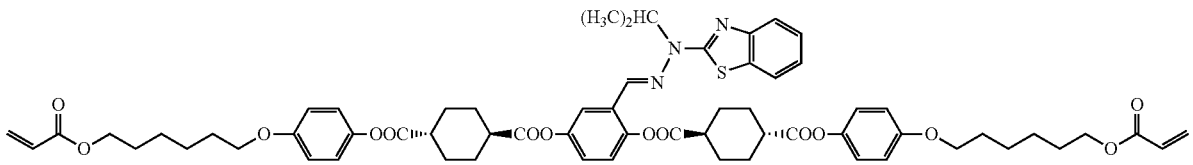

Step 1: Synthesis of Compound (3b)

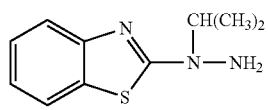

Compound (3b)

30.0 g (181.6 mmol) of 2-hydrazinobenzothiazole was dissolved in 500 ml of DMF under a nitrogen stream in a three-necked reactor equipped with a thermometer. To this solution was added 118.3 g (363.2 mmol) of cesium carbonate and the mixture was cooled to 0° C. 33.3 g (272.3 mmol) of 2-bromopropane was added. The whole mass was stirred at 0° C. for 1 hour, and further stirred at 25° C. for 20 hours. 1,500 ml of distilled water was then added to the reaction solution and the mixture was extracted twice with 1,000 ml of ethyl acetate. After drying the organic layer over anhydrous sodium sulfate, sodium sulfate was filtered off. The filtrate was concentrated on a rotary evaporator and the concentrate was purified by silica gel column chromatography (THF/toluene=1:9) to afford 11.1 g of compound (3b) as a white solid (yield: 29%).

The structure of the target product was identified by $^1$H-NMR.

$^1$H-NMR (500 MHz, DMSO-d$_6$, TMS, δ ppm): 7.65 (dd, 1H, J=1.0 Hz, 8.0 Hz), 7.35 (dd, 1H, J=1.0 Hz, 8.0 Hz), 7.20 (dt, 1H, J=1.0 Hz, 7.5 Hz), 6.98 (dt, 1H, J=1.0 Hz, 7.5 Hz), 5.10 (s, 2H), 4.61-4.72 (m, 1H), 1.17 (d, 6H, J=6.5 Hz)

Step 2: Synthesis of Polymerizable Compound (IIIb)

The same operation as in Example 73 was performed except that in Step 2, 4.05 g (16.22 mmol) of compound (3a) synthesized in Example 37 was changed to 3.36 g (16.22 mmol) of compound (3b) synthesized in Step 1 above. As a result, 11.08 g of polymerizable compound (IIIb) was obtained (yield: 78.7%).

The structure of the target product was identified by $^1$H-NMR.

$^1$H-NMR (500 MHz, CDCl$_3$, TMS, δ ppm): 8.08 (s, 1H), 7.74 (d, 1H, J=2.5 Hz), 7.69 (dd, 1H, J=1.0 Hz, 8.0 Hz), 7.65 (d, 1H, J=8.0 Hz), 7.33 (dt, 1H, J=1.0 Hz, 7.5 Hz), 7.16 (dt, 1H, J=1.0 Hz, 7.5 Hz), 7.08-7.13 (m, 2H), 6.99 (d, 2H, J=9.0 Hz), 6.98 (d, 2H, J=9.0 Hz), 6.88 (d, 4H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 5.29-5.39 (m, 1H), 4.17 (t, 4H, J=6.5 Hz), 3.94 (t, 4H, J=6.5 Hz), 2.54-2.74 (m, 4H), 2.25-2.39 (m, 8H), 1.65-1.84 (m, 16H), 1.62 (d, 6H, J=7.0 Hz), 1.41-1.55 (m, 8H)

(Example 75) Synthesis of Polymerizable Compound (IIIc)

Polymerizable compound (IIIc)

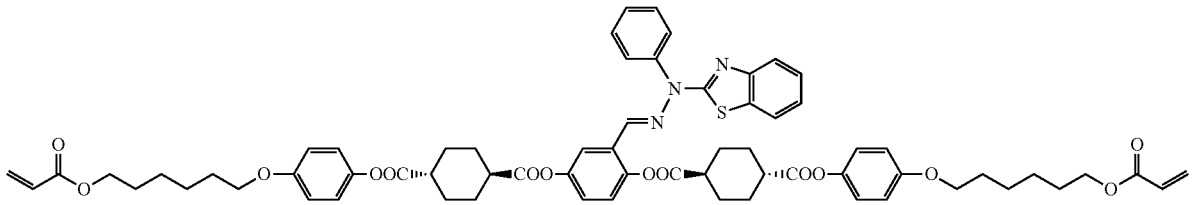

Step 1: Synthesis of Compound (3c)

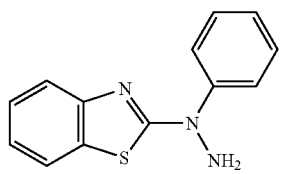

Compound (3c)

15.0 g (88.45 mmol) of 2-chlorobenzothiazole and 38.25 g (353.7 mmol) of phenylhydrazine were dissolved in 150 ml of ethylene glycol under a nitrogen stream in a three-necked reactor equipped with a thermometer. This solution was heated to 140° C. and stirred for 5 hours. After completion of the reaction, 1,000 ml of distilled water was added to the reaction solution and the mixture was extracted twice with 500 ml of ethyl acetate. After drying the organic layer over anhydrous sodium sulfate, sodium sulfate was filtered off. After concentrating the filtrate on a rotary evaporator, 50 ml of THF was added to dissolve the concentrate. The solution was poured into 1,000 ml of distilled water and the precipitated solid was collected by filtration. The residues were washed with distilled water and dried under vacuum to afford a yellow solid. The yellow solid was placed in a flask, 250 ml of toluene was added, and the mixture was stirred for 30 minutes, followed by filtration to remove solid components insoluble in toluene. The filtrate was concentrated on a rotary evaporator and the concentrate was purified by silica gel column chromatography (THF/toluene=2:50) to afford 4.70 g of compound (3c) as a yellow oil (yield: 22%).

The structure of the target product was identified by $^1$H-NMR.

$^1$H-NMR (500 MHz, DMSO-$d_6$, TMS, δ ppm): 8.01 (dd, 2H, J=1.0 Hz, 9.0 Hz), 7.78 (dd, 1H, J=1.0 Hz, 8.0 Hz), 7.51 (dd, 1H, J=1.0 Hz, 8.0 Hz), 7.43 (dd, 2H, J=7.5 Hz, 8.5 Hz), 7.28 (dt, 1H, J=1.0 Hz, 7.5 Hz), 7.08-7.16 (m, 2H), 6.26 (s, 2H)

Step 2: Synthesis of Polymerizable Compound (IIIc)

The same operation as in Example 73 was performed except that in Step 2, 4.05 g (16.22 mmol) of compound (3a) synthesized in Example 37 was changed to 3.91 g (16.22 mmol) of compound (3c) synthesized in Step 1 above. As a result, 10.65 g of polymerizable compound (IIIc) was obtained (yield: 73.4%).

The structure of the target product was identified by $^1$H-NMR.

$^1$H-NMR (500 MHz, CDCl$_3$, TMS, δ ppm): 7.82 (d, 1H, J=2.5 Hz), 7.73 (dd, 1H, J=1.0 Hz, 8.0 Hz), 7.64-7.70 (m, 2H), 7.60 (d, 2H, J=7.5 Hz), 7.35-7.42 (m, 3H), 7.30 (dt, 1H, J=1.0 Hz, 7.5 Hz), 7.18 (dt, 1H, J=1.0 Hz, 7.5 Hz), 7.03-7.12 (m, 2H), 7.00 (d, 2H, J=9.0 Hz), 6.99 (d, 2H, J=9.0 Hz), 6.90 (d, 2H, J=9.0 Hz), 6.89 (d, 2H, J=9.0 Hz), 6.41 (dd, 1H, J=1.5 Hz, 17.5 Hz), 6.41 (dd, 1H, J=1.5 Hz, 17.5 Hz), 6.13 (dd, 1H, J=10.5 Hz, 17.5 Hz), 6.13 (dd, 1H, J=10.5 Hz, 17.5 Hz), 5.82 (dd, 1H, J=1.5 Hz, 10.5 Hz), 5.82 (dd, 1H, J=1.5 Hz, 10.5 Hz), 4.18 (t, 2H, J=6.5 Hz), 4.18 (t, 2H, J=6.5 Hz), 3.92-3.98 (m, 4H), 2.56-2.71 (m, 2H), 2.41-2.50 (m, 1H), 2.27-2.40 (m, 5H), 2.12-2.22 (m, 2H), 1.64-1.91 (m, 14H), 1.41-1.56 (m, 10H), 1.19-1.31 (m, 2H)

(Example 76) Synthesis of Polymerizable Compound (IIId)

Step 1: Synthesis of Compound (3d)

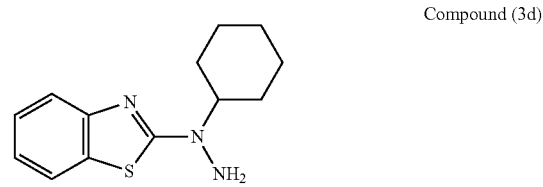 [SMILES: NN(c1nc2ccccc2s1)C1CCCCC1]

Compound (3d)

12.5 g (83.0 mmol) of cyclohexylhydrazine hydrochloride was dissolved in 40 ml of triethylamine under a nitrogen stream in a four-necked reactor equipped with a thermometer. To this solution was added 28.15 g (166.0 mmol) of 2-chlorobenzothiazole and the whole mass was stirred at 80° C. for 5 hours. After completion of the reaction, the reaction solution was cooled to 20° C., poured into 500 ml of saturated aqueous solution of sodium bicarbonate, and the mixture was extracted with 1,000 ml of ethyl acetate. After drying the ethyl acetate layer over anhydrous sodium sulfate, sodium sulfate was filtered off. Ethyl acetate was distilled off under reduced pressure from the filtrate on a rotary evaporator to afford a yellow solid. This yellow solid was purified by silica gel column chromatography (hexane/ethyl acetate=75:25) to afford 5.10 g of compound (3d) as a white solid (yield: 24.8%).

The structure of the target product was identified by $^1$H-NMR.

$^1$H-NMR (400 MHz, CDCl$_3$, TMS, δ ppm): 7.58 (d, 1H, J=7.8 Hz), 7.52 (d, 1H, J=8.2 Hz), 7.26 (dd, 1H, J=7.4 Hz, 8.2 Hz), 7.05 (dd, 1H, J=7.4 Hz, 7.8 Hz), 4.25-4.32 (m, 1H), 4.04 (s, 2H), 1.84-1.88 (m, 4H), 1.68-1.73 (m, 1H), 1.43-1.59 (m, 4H), 1.08-1.19 (m, 1H)

Step 2: Synthesis of Polymerizable Compound (IIId)

The same operation as in Example 73 was performed except that in Step 2, 4.05 g (16.22 mmol) of compound (3a) synthesized in Example 37 was changed to 4.01 g (16.22 mmol) of compound (3d) synthesized in Step 1 above. As a result, 11.11 g of polymerizable compound (IIId) was obtained (yield: 76.2%).

The structure of the target product was identified by $^1$H-NMR.

$^1$H-NMR (500 MHz, CDCl$_3$, TMS, δ ppm): 8.15 (s, 1H), 7.72 (d, 1H, J=1.5 Hz), 7.68 (dd, 1H, J=1.5 Hz, 8.0 Hz), 7.66 (dd, 1H, J=1.5 Hz, 8.0 Hz), 7.31-7.35 (m, 1H), 7.14-7.18 (m, 1H), 7.13 (d, 1H, J=9.0 Hz), 7.10 (dd, 1H, J=1.5 Hz, 9.0 Hz),

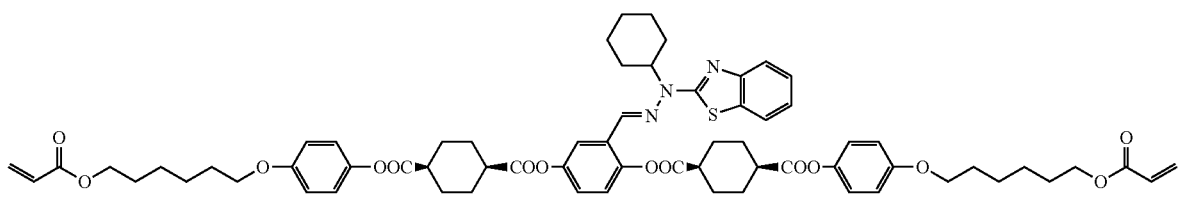

Polymerizable compound (IIId)

6.96-7.00 (m, 4H), 6.86-6.90 (m, 4H), 6.40 (dd, 2H, J=1.5 Hz, 17.0 Hz), 6.13 (dd, 2H, J=10.0 Hz, 17.0 Hz), 5.82 (dd, 2H, J=1.5 Hz, 10.0 Hz), 4.62-4.70 (m, 1H), 4.17 (t, 4H, J=6.5 Hz), 3.94 (t, 4H, J=6.5 Hz), 2.55-2.74 (m, 4H), 2.27-2.47 (m, 10H), 1.90-2.00 (m, 4H), 1.65-1.85 (m, 16H), 1.42-1.55 (m, 10H), 1.24-1.33 (m, 2H)

(Example 77) Synthesis of Polymerizable Compound (IIIe)

Step 1: Synthesis of Compound (3e)

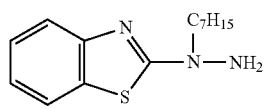

Compound (3e)

10.0 g (60.5 mmol) of 2-hydrazinobenzothiazole was dissolved in 150 ml of DMF under a nitrogen stream in a three-necked reactor equipped with a thermometer. To this solution was added 39.4 g (121.0 mmol) of cesium carbonate and the mixture was cooled to 0° C. 16.4 g (72.5 mmol) of iodoheptane was added dropwise over 5 minutes. After completion of the dropwise addition, the whole mass was stirred at 25° C. for 3 hours. After completion of the reaction, 1,000 ml of water was added to the reaction solution and the mixture was extracted twice with 500 ml of ethyl acetate. After drying the organic layer over anhydrous sodium sulfate, sodium sulfate was filtered off. After concentrating the filtrate on a rotary evaporator, the concentrate was purified by silica gel column chromatography (n-hexane/ethyl acetate=85:15) to afford 9.05 g of compound (3e) as a white solid (yield: 56.9%).

The structure of the target product was identified by $^1$H-NMR.

$^1$H-NMR (500 MHz, CDCl$_3$, TMS, δ ppm): 7.59 (dd, 1H, J=1.5 Hz, 8.0 Hz), 7.53 (dd, 1H, J=1.5 Hz, 8.0 Hz), 7.06-7.28 (m, 2H), 4.22 (s, 2H), 3.75 (t, 2H, J=7.0 Hz), 1.29-1.38 (m, 10H), 0.88 (t, 3H, J=7.0 Hz)

Step 2: Synthesis of Polymerizable Compound (IIIe)

The same operation as in Example 73 was performed except that in Step 2, 4.05 g (16.22 mmol) of compound (3a) synthesized in Example 37 was changed to 4.27 g (16.22 mmol) of compound (3e) synthesized in Step 1 above. As a result, 11.96 g of polymerizable compound (IIIe) was obtained (yield: 80.9%).

Polymerizable compound (IIIe)

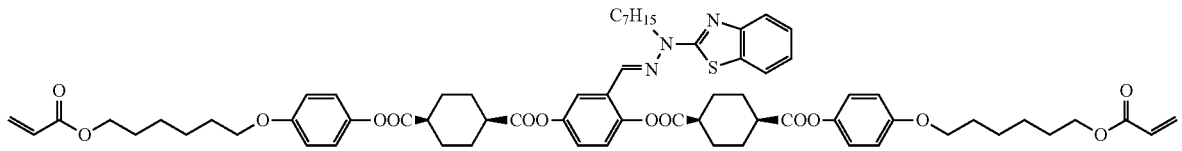

The structure of the target product was identified by $^1$H-NMR.

$^1$H-NMR (500 MHz, CDCl$_3$, TMS, δ ppm): 7.75 (d, 1H, J=1.5 Hz), 7.66-7.70 (m, 3H), 7.34 (ddd, 1H, J=1.5 Hz, 8.0 Hz, 8.0 Hz), 7.17 (ddd, 1H, J=1.5 Hz, 8.0 Hz, 8.0 Hz), 7.08-7.14 (m, 2H), 6.95-7.01 (m, 4H), 6.87-6.90 (m, 4H), 6.40 (dd, 2H, J=1.5 Hz, 17.5 Hz), 6.12 (dd, 2H, J=10.5 Hz, 17.5 Hz), 5.82 (dd, 2H, J=1.5 Hz, 10.5 Hz), 4.30 (t, 2H, J=7.0 Hz), 4.18 (t, 4H, J=7.0 Hz), 3.95 (t, 4H, J=7.0 Hz), 2.55-2.73 (m, 4H), 2.26-2.40 (m, 8H), 1.65-1.84 (m, 16H), 1.36-1.55 (m, 14H), 1.25-1.35 (m, 4H), 0.87 (t, 3H, J=7.0 Hz)

(Example 78) Synthesis of Polymerizable Compound (IIIf)

Polymerizable compound (IIIf)

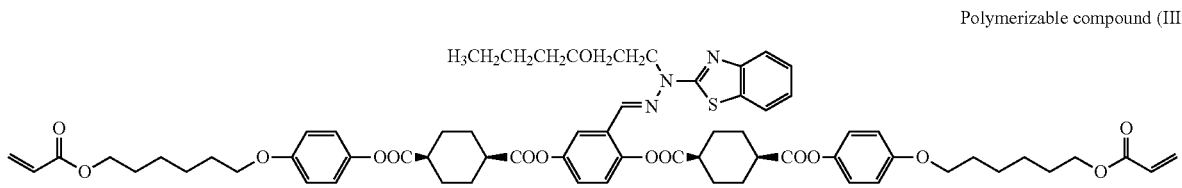

Step 1: Synthesis of Compound (3f)

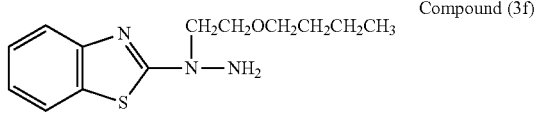

Compound (3f)

10.0 g (60.5 mmol) of 2-hydrazinobenzothiazole was dissolved in 150 ml of DMF under a nitrogen stream in a three-necked reactor equipped with a thermometer. To this solution was added 39.4 g (121.0 mmol) of cesium carbonate and the mixture was cooled to 0° C. 9.90 g (72.5 mmol) of butyl 2-chloroethyl ether was added dropwise over 5 minutes. After completion of the dropwise addition, the whole mass was stirred at 25° C. for 3 hours. After completion of the reaction, 1,000 ml of water was added to the reaction solution and the mixture was extracted twice with 500 ml of ethyl acetate. After drying the organic layer over anhydrous sodium sulfate, sodium sulfate was filtered off. After concentrating the filtrate on a rotary evaporator, the concentrate was purified by silica gel column chromatography (n-hexane/ethyl acetate=75:25) to afford 8.50 g of compound (3f) as a white solid (yield 53.0%).

The structure of the target product was identified by $^1$H-NMR.

$^1$H-NMR (500 MHz, CDCl$_3$, TMS, δ ppm): 7.61 (dd, 1H, J=1.0 Hz, 8.0 Hz), 7.50 (dd, 1H, J=1.0 Hz, 8.0 Hz), 7.27-7.29 (m, 1H), 7.04-7.08 (m, 1H), 4.70 (s, 2H), 4.01 (t, 2H, J=5.0 Hz), 3.82 (t, 2H, J=5.0 Hz), 3.44 (t, 2H, J=7.0 Hz), 1.52-1.57 (m, 2H), 1.31-1.39 (m, 2H), 0.90 (t, 3H, J=7.0 Hz)

Step 2: Synthesis of Polymerizable Compound (IIIf)

The same operation as in Example 73 was performed except that in Step 2, 4.05 g (16.22 mmol) of compound (3a) synthesized in Example 37 was changed to 4.30 g (16.22 mmol) of compound (3f) synthesized in Step 1 above. As a result, 11.77 g of polymerizable compound (HID was obtained (yield: 79.5%).

The structure of the target product was identified by $^1$H-NMR.

$^1$H-NMR (500 MHz, CDCl$_3$, TMS, δ ppm): 8.03 (s, 1H), 7.76 (d, 1H, J=1.5 Hz), 7.65-7.71 (m, 2H), 7.34 (ddd, 1H, J=1.5 Hz, 8.0 Hz, 8.0 Hz), 7.17 (ddd, 1H, J=1.5 Hz, 8.0 Hz, 8.0 Hz), 7.09-7.12 (m, 2H), 6.96-7.00 (m, 4H), 6.87-6.90 (m, 4H), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.45 (t, 2H, J=5.5 Hz), 4.18 (t, 4H, J=7.0 Hz), 3.95 (t, 4H, J=7.0 Hz), 3.79 (t, 2H, J=5.5 Hz), 3.44 (t, 2H, J=7.0 Hz), 2.55-2.74 (m, 4H), 2.28-2.40 (m, 8H), 1.65-1.83 (m, 16H), 1.42-1.55 (m, 10H), 1.25-1.34 (m, 2H), 0.85 (t, 3H, J=7.0 Hz)

(Example 79) Synthesis of Polymerizable Compound (IIIi)

four-necked reactor equipped with a thermometer. 14.9 g (45.8 mmol) of cesium carbonate and 4.94 g (36.6 mmol) of 4-bromo-1-butene were added to this solution and the whole mass was stirred at 25° C. for 7 hours. After completion of the reaction, the reaction solution was poured into 200 ml of water and the mixture was extracted with 300 ml of ethyl acetate. After drying the ethyl acetate layer over anhydrous sodium sulfate, sodium sulfate was filtered off. Ethyl acetate was distilled off under reduced pressure from the filtrate on a rotary evaporator to afford a yellow solid. This yellow solid was purified by silica gel column chromatography (hexane/ethyl acetate=70:30) to afford 4.40 g of compound (3i) as a white solid (yield: 65.8%).

The structure of the target product was identified by $^1$H-NMR.

$^1$H-NMR (500 MHz, CDCl$_3$, TMS, δ ppm): 7.60 (dd, 1H, J=1.0 Hz, 8.0 Hz), 7.54 (dd, 1H, J=1.0 Hz, 8.0 Hz), 7.28 (ddd, 1H, J=1.0 Hz, 7.5 Hz, 8.0 Hz), 7.06 (ddd, 1H, J=1.0 Hz, 7.5 Hz, 8.0 Hz), 5.89 (ddt, 1H, J=7.0 Hz, 10.5 Hz, 17.0 Hz), 5.17 (ddt, 1H, J=1.5 Hz, 3.0 Hz, 17.0 Hz), 5.09 (ddt, 1H, J=1.0 Hz, 3.0 Hz, 10.5 Hz), 4.26 (s, 2H), 3.85 (t, 2H, J=7.0 Hz), 2.52 (dddt, 2H, J=1.0 Hz, 1.5 Hz, 7.0 Hz, 7.0 Hz)

Step 2: Synthesis of Polymerizable Compound (IIIi)

The same operation as in Example 73 was performed except that in Step 2, 4.05 g (16.22 mmol) of compound (3a) synthesized in Example 37 was changed to 3.56 g (16.22 mmol) of compound (3i) synthesized in Step 1 above. As a result, 9.88 g of polymerizable compound (IIIi) was obtained (yield: 69.4%).

The structure of the target product was identified by $^1$H-NMR.

$^1$H-NMR (500 MHz, CDCl$_3$, TMS, δ ppm): 7.76 (d, 1H, J=2.5 Hz), 7.67-7.70 (m, 3H), 7.35 (ddd, 1H, J=1.5 Hz, 7.5

Polymerizable compound (IIIi)

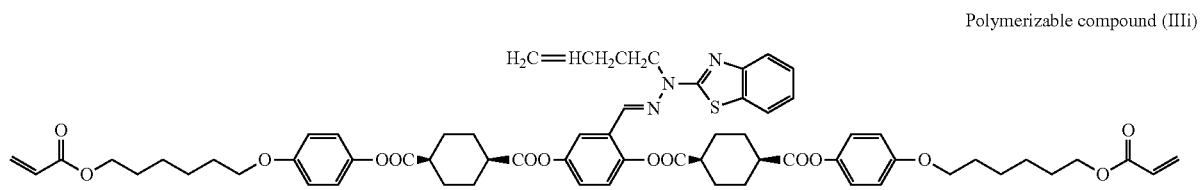

Step 1: Synthesis of Compound (3i)

Compound (3i)

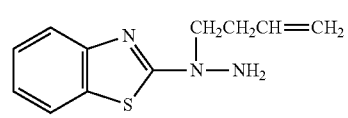

5.04 g (30.5 mmol) of 2-hydrazinobenzothiazole was dissolved in 50 ml of DMF under a nitrogen stream in a Hz, 8.0 Hz), 7.18 (ddd, 1H, J=1.5 Hz, 7.5 Hz, 8.0 Hz), 7.10-7.14 (m, 2H), 6.99 (d, 2H, J=9.5 Hz), 6.98 (d, 2H, J=9.5 Hz), 6.88 (d, 4H, J=9.5 Hz), 6.40 (dd, 2H, J=1.5 Hz, 17.5 Hz), 6.13 (dd, 2H, J=10.5 Hz, 17.5 Hz), 5.89 (ddt, 1H, J=6.5 Hz, 10.5 Hz, 17.0 Hz), 5.82 (dd, 2H, J=1.5 Hz, 10.5 Hz), 5.18 (dd, 1H, J=1.5 Hz, 17.0 Hz), 5.15 (dd, 1H, J=1.5 Hz, 10.5 Hz), 4.38 (t, 2H, J=7.0 Hz), 4.18 (t, 4H, J=6.5 Hz), 3.95 (t, 4H, J=6.5 Hz), 2.58-2.68 (m, 4H), 2.51 (dt, 2H, J=6.5 Hz, 7.0 Hz), 2.31-2.35 (m, 8H), 1.76-1.85 (m, 4H), 1.65-1.74 (m, 12H), 1.41-1.54 (m, 8H)

(Example 80) Synthesis of Polymerizable Compound (IIIj)

Polymerizable compound (IIIj)

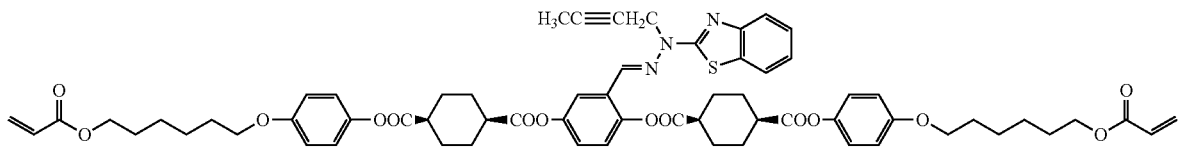

Step 1: Synthesis of Compound (3j)

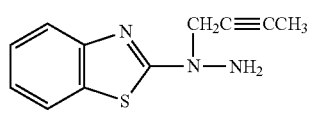

Compound (3j)

10.0 g (60.5 mmol) of 2-hydrazinobenzothiazole was dissolved in 150 ml of DMF under a nitrogen stream in a four-necked reactor equipped with a thermometer. To this solution were added 39.4 g (121.0 mmol) of cesium carbonate and 9.65 g (72.5 mmol) of 1-bromo-2-butyne, and the whole mass was stirred at 25° C. for 20 hours. After completion of the reaction, the reaction solution was added to 1,000 ml of water and the mixture was extracted with 500 ml of ethyl acetate. After drying the ethyl acetate layer over anhydrous sodium sulfate, sodium sulfate was filtered off. Ethyl acetate was distilled off from the filtrate under reduced pressure on a rotary evaporator to afford a brown solid. This brown solid was purified by silica gel column chromatography (n-hexane/ethyl acetate=85:15) to afford 6.25 g of compound (3j) as a white solid (yield: 47.5%).

The structure of the target product was identified by $^1$H-NMR.

$^1$H-NMR (500 MHz, CDCl$_3$, TMS, δ ppm): 7.63 (dd, 1H, J=1.3 Hz, 7.8 Hz), 7.58 (dd, 1H, J=1.3 Hz, 7.8 Hz), 7.29 (ddd, 1H, J=1.3 Hz, 7.8 Hz, 7.8 Hz), 7.10 (ddd, 1H, J=1.3 Hz, 7.8 Hz, 7.8 Hz), 4.56 (q, 2H, J=2.5 Hz), 4.36 (s, 2H), 1.84 (t, 3H, J=2.5 Hz)

Step 2: Synthesis of Polymerizable Compound (IIIj)

The same operation as in Example 73 was performed except that in Step 2, 4.05 g (16.22 mmol) of compound (3a) synthesized in Example 37 was changed to 3.52 g (16.22 mmol) of compound (3j) synthesized in Step 1 above. As a result, 9.46 g of polymerizable compound (IIIj) was obtained (yield: 66.6%).

The structure of the target product was identified by $^1$H-NMR.

$^1$H-NMR (500 MHz, CDCl$_3$, TMS, δ ppm): 7.90 (s, 1H), 7.78 (d, 1H, J=1.3 Hz), 7.67-7.73 (m, 2H), 7.35 (ddd, 1H, J=1.3 Hz, 7.5 Hz, 7.5 Hz), 7.18 (ddd, 1H, J=1.3 Hz, 7.5 Hz, 7.5 Hz), 7.09-7.15 (m, 2H), 6.95-7.01 (m, 4H), 6.85-6.91 (m, 4H), 6.40 (dd, 2H, J=1.5 Hz, 17.0 Hz), 6.13 (dd, 2H, J=10.5 Hz, 17.0 Hz), 5.82 (dd, 2H, J=1.5 Hz, 10.5 Hz), 5.06 (d, 2H, J=2.0 Hz), 4.18 (t, 4H, J=6.0 Hz), 3.95 (t, 4H, J=6.0 Hz), 2.55-2.76 (m, 4H), 2.26-2.43 (m, 8H), 1.64-1.83 (m, 19H), 1.41-1.55 (m, 8H)

(Example 81) Synthesis of Polymerizable Compound (IIIk)

Polymerizable compound (IIIk)

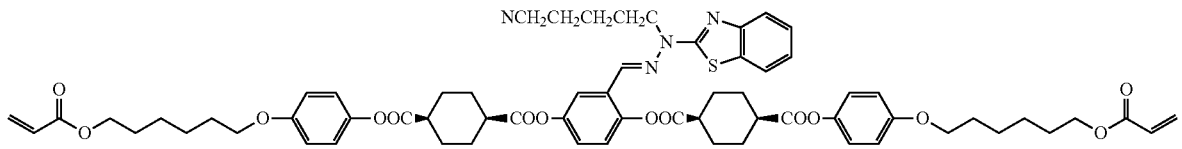

Step 1: Synthesis of Compound (3k)

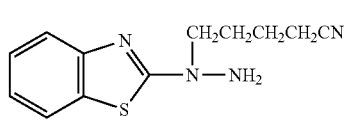

Compound (3k)

10.0 g (60.5 mmol) of 2-hydrazinobenzothiazole was dissolved in 100 ml of DMF under a nitrogen stream in a four-necked reactor equipped with a thermometer. To this solution were added 41.8 g (304 mmol) of potassium carbonate and 10.34 g (63.8 mmol) of 5-bromovaleronitrile and the whole mass was stirred at 60° C. for 8 hours. After completion of the reaction, the reaction solution was cooled to 20° C. and added to 1,000 ml of water, and the mixture was extracted with 1,000 ml of ethyl acetate. After drying the ethyl acetate layer over anhydrous sodium sulfate, sodium sulfate was filtered off. Ethyl acetate was distilled off under reduced pressure from the filtrate on a rotary evaporator to afford a yellow solid. This yellow solid was purified by silica gel column chromatography (n-hexane/ethyl acetate=60:40) to afford 6.82 g of compound (3k) as a white solid (yield: 45.7%).

The structure of the target product was identified by $^1$H-NMR.

¹H-NMR (400 MHz, CDCl₃, TMS, δ ppm): 7.60 (d, 1H, J=7.8 Hz), 7.51 (d, 1H, J=8.1 Hz), 7.28 (dd, 1H, J=7.3 Hz, 8.1 Hz), 7.07 (dd, 1H, J=7.3 Hz, 7.8 Hz), 4.23 (s, 2H), 3.81 (t, 2H, J=6.9 Hz), 2.46 (t, 2H, J=7.1 Hz), 1.88-1.95 (m, 2H), 1.71-1.79 (m, 2H)

Step 2: Synthesis of Polymerizable Compound (IIIk)

The same operation as in Example 73 was performed except that in Step 2, 4.05 g (16.22 mmol) of compound (3a) synthesized in Example 37 was changed to 4.00 g (16.22 mmol) of compound (3k) synthesized in Step 1 above. As a result, 11.23 g of polymerizable compound (IIIk) was obtained (yield: 77.1%).

The structure of the target product was identified by ¹H-NMR.

¹H-NMR (500 MHz, CDCl₃, TMS, δ ppm): 7.74 (d, 1H, J=1.5 Hz), 7.64-7.72 (m, 3H), 7.35 (ddd, 1H, J=1.5 Hz, 8.0 Hz, 8.0 Hz), 7.19 (ddd, 1H, J=1.5 Hz, 8.0 Hz, 8.0 Hz), 7.10-7.14 (m, 2H), 6.96-7.01 (m, 4H), 6.86-6.91 (m, 4H), 6.40 (dd, 2H, J=1.5 Hz, 17.0 Hz), 6.12 (dd, 2H, J=10.5 Hz, 17.0 Hz), 5.82 (dd, 2H, J=1.5 Hz, 10.5 Hz), 4.22 (t, 2H, J=6.5 Hz), 4.18 (t, 4H, J=6.5 Hz), 3.95 (t, 4H, J=6.5 Hz), 2.58-2.75 (m, 4H), 2.55 (t, 2H, J=6.5 Hz), 2.26-2.40 (m, 8H), 1.96 (tt, 2H, J=6.5 Hz, 6.5 Hz), 1.66-1.83 (m, 18H), 1.42-1.55 (m, 8H)

(Example 82) Synthesis of Polymerizable Compound (IIIm)

Step 1: Synthesis of Compound (3m)

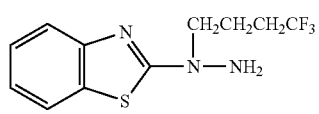

Compound (3m)

14.5 g (87.5 mmol) of 2-hydrazinobenzothiazole was dissolved in 200 ml of DMF under a nitrogen stream in a four-necked reactor equipped with a thermometer. To this solution were added 36.3 g (263 mmol) of potassium carbonate and 25.0 g (105 mmol) of 1,1,1-trifluoro-4-iodobutane and the whole mass was stirred at 80° C. for 8 hours. After completion of the reaction, the reaction solution was cooled to 20° C. and added to 1,000 ml of water, and the mixture was extracted with 1,000 ml of ethyl acetate. After drying the ethyl acetate layer over anhydrous sodium sulfate, sodium sulfate was filtered off. Ethyl acetate was distilled off under reduced pressure from the filtrate on a rotary evaporator to afford a yellow solid. This yellow solid was purified by silica gel column chromatography (n-hexane/ethyl acetate=85:15) to afford 9.61 g of compound (3m) as a white solid (yield: 39.9%).

The structure of the target product was identified by ¹H-NMR.

¹H-NMR (500 MHz, CDCl₃, TMS, δ ppm): 7.61 (d, 1H, J=8.0 Hz), 7.54 (d, 1H, J=7.8 Hz), 7.30 (dd, 1H, J=7.8 Hz, 7.8 Hz), 7.09 (dd, 1H, J=7.8 Hz, 8.0 Hz), 4.24 (s, 2H), 3.81 (t, 2H, J=7.0 Hz), 2.16-2.26 (m, 2H), 1.99-2.05 (m, 2H)

Step 2: Synthesis of Polymerizable Compound (IIIm)

The same operation as in Example 73 was performed except that in

Step 2, 4.05 g (16.22 mmol) of compound (3a) synthesized in Example 37 was changed to 4.47 g (16.22 mmol) of compound (3m) synthesized in Step 1 above. As a result, 11.81 g of polymerizable compound (IIIm) was obtained (yield: 79.1%).

Polymerizable compound (IIIm)

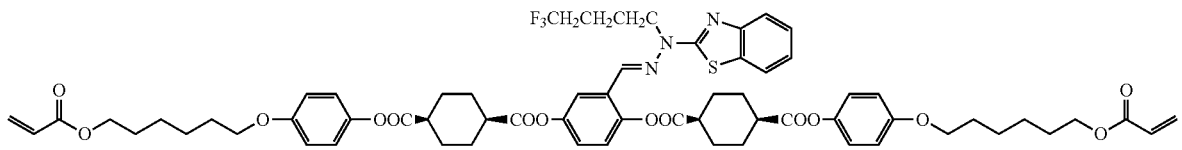

The structure of the target product was identified by ¹H-NMR.

¹H-NMR (500 MHz, CDCl₃, TMS, δ ppm): 7.75 (s, 1H), 7.65-7.71 (m, 3H), 7.34 (ddd, 1H, J=1.0 Hz, 7.5 Hz, 7.5 Hz), 7.17 (ddd, 1H, J=1.0 Hz, 7.5 Hz, 7.5 Hz), 7.08-7.14 (m, 2H), 6.96-7.01 (m, 4H), 6.86-6.91 (m, 4H), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.42 (t, 2H, J=7.5 Hz), 4.18 (t, 4H, J=6.5 Hz), 3.95 (t, 4H, J=6.5 Hz), 2.55-2.73 (m, 4H), 2.25-2.38 (m, 10H), 2.04 (tt, 2H, J=7.5 Hz, 7.5 Hz), 1.64-1.84 (m, 16H), 1.42-1.55 (m, 8H)

(Example 83) Synthesis of Polymerizable Compound (IIIn)

Polymerizable compound (IIIn)

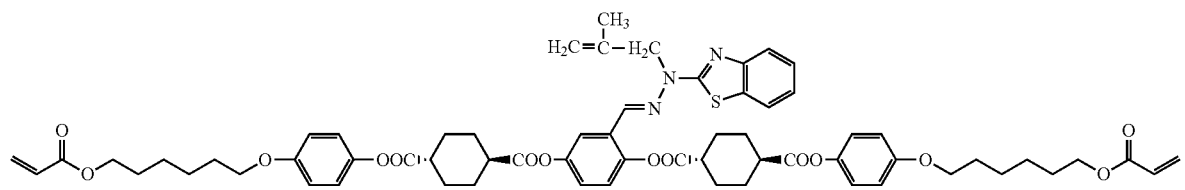

Step 1: Synthesis of Compound (3n)

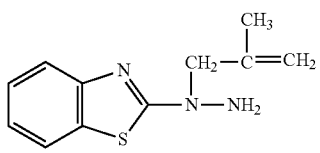

Compound (3n)

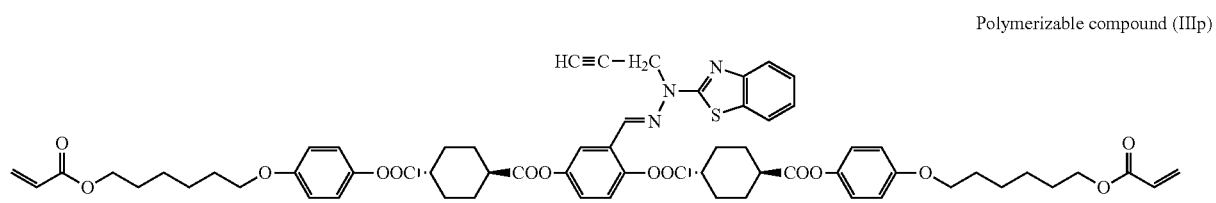

Polymerizable compound (IIIp)

40.0 g (241.6 mmol) of 2-hydrazinobenzothiazole was dissolved in 300 ml of DMF under a nitrogen stream in a four-necked reactor equipped with a thermometer. To this solution were added 118 g (363 mmol) of cesium carbonate and 39.2 g (291 mmol) of 3-bromo-2-methyl-1-propene and the whole mass was stirred at 25° C. for 18 hours. After completion of the reaction, the reaction solution was added to 1,500 ml of water and the mixture was extracted with 2,000 ml of ethyl acetate. After drying the ethyl acetate layer over anhydrous sodium sulfate, sodium sulfate was filtered off. Ethyl acetate was distilled off under reduced pressure from the filtrate on a rotary evaporator to afford a yellow solid. This yellow solid was purified by silica gel column chromatography (hexane/ethyl acetate=80:20) to afford 5.88 g of compound (3n) as a white solid (yield: 11.1%).

The structure of the target product was identified by $^1$H-NMR.

$^1$H-NMR (500 MHz, CDCl$_3$, TMS, δ ppm): 7.59 (dd, 1H, J=1.0 Hz, 8.0 Hz), 7.52 (dd, 1H, J=1.5 Hz, 8.0 Hz), 7.26 (ddd, 1H, J=1.0 Hz, 7.5 Hz, 8.0 Hz), 7.05 (ddd, 1H, J=1.5 Hz, 7.5 Hz, 8.0 Hz), 4.98 (s, 1H), 4.86 (s, 1H), 4.29 (s, 2H), 4.12 (s, 2H), 1.71 (s, 3H)

Step 2: Synthesis of Polymerizable Compound (IIIn)

The same operation as in Example 73 was performed except that in Step 2, 4.05 g (16.22 mmol) of compound (3a) synthesized in Example 37 was changed to 3.56 g (16.22 mmol) of compound (3n) synthesized in Step 1 above. As a result, 10.05 g of polymerizable compound (IIIn) was obtained (yield: 70.6%).

The structure of the target product was identified by $^1$H-NMR.

$^1$H-NMR (500 MHz, CDCl$_3$, TMS, δ ppm): 7.74 (d, 1H, J=2.5 Hz), 7.70 (d, 1H, J=7.5 Hz), 7.67 (d, 1H, J=8.0 Hz), 7.63 (s, 1H), 7.34 (dd, 1H, J=7.5 Hz, 8.0 Hz), 7.18 (dd, 1H, J=7.5 Hz, 7.5 Hz), 7.12 (d, 1H, J=9.0 Hz), 7.10 (dd, 1H, J=2.5 Hz, 9.0 Hz), 6.99 (d, 2H, J=9.0 Hz), 6.98 (d, 2H, J=9.0 Hz), 6.88 (d, 4H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.98 (s, 1H), 4.90 (s, 2H), 4.83 (s, 1H), 4.18 (t, 4H, J=6.5 Hz), 3.95 (t, 4H, J=6.5 Hz), 2.56-2.66 (m, 4H), 2.31-2.36 (m, 8H), 1.76-1.82 (m, 7H), 1.64-1.74 (m, 12H), 1.40-1.55 (m, 8H)

(Example 84) Synthesis of Polymerizable Compound (IIIp)

Step 1: Synthesis of Compound (3p)

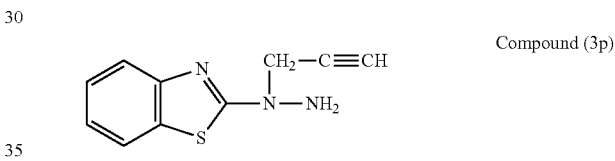

Compound (3p)

20.0 g (121.1 mmol) of 2-hydrazinobenzothiazole was dissolved in 400 ml of DMF under a nitrogen stream in a three-necked reactor equipped with a thermometer. To this solution were added 78.9 g (242.1 mmol) of cesium carbonate and 17.3 g (145.3 mmol) of propargyl bromide and the whole mass was stirred at 25° C. for 15 hours. After completion of the reaction, 1,500 ml of distilled water was added to the reaction solution and the mixture was extracted twice with 1,000 ml of ethyl acetate. After drying the organic layer over anhydrous sodium sulfate, sodium sulfate was filtered off. After concentrating the filtrate on a rotary evaporator, the concentrate was purified by silica gel column chromatography (THF/toluene=1:19) to afford 6.90 g of compound (3p) as a pale yellow solid (yield: 28%).

The structure of the target product was identified by $^1$H-NMR.

$^1$H-NMR (500 MHz, DMSO-d$_6$, TMS, δ ppm): 7.73 (dd, 1H, J=1.0 Hz, 8.0 Hz), 7.44 (dd, 1H, J=1.0 Hz, 8.0 Hz), 7.26 (dt, 1H, J=1.0 Hz, 7.5 Hz), 7.06 (dt, 1H, J=1.0 Hz, 7.5 Hz), 5.31 (s, 2H), 4.52 (d, 2H, J=2.5 Hz), 3.35 (t, 1H, J=2.5 Hz)

Step 2: Synthesis of Polymerizable Compound (IIIp)

The same operation as in Example 73 was performed except that in Step 2, 4.05 g (16.22 mmol) of compound (3a) synthesized in Example 37 was changed to 3.30 g (16.22 mmol) of compound (3p) synthesized in Step 1 above. As a result, 10.12 g of polymerizable compound (Hip) was obtained (yield: 72.1%).

The structure of the target product was identified by ¹H-NMR.

¹H-NMR (500 MHz, CDCl₃, TMS, δ ppm): 7.92 (s, 1H), 7.67-7.78 (m, 3H), 7.36 (dt, 1H, J=1.0 Hz, 7.5 Hz), 7.20 (dt, 1H, J=1.0 Hz, 7.5 Hz), 7.11-7.17 (m, 2H), 6.99 (d, 2H, J=9.0 Hz), 6.98 (d, 2H, J=9.0 Hz), 6.88 (d, 2H, J=9.0 Hz), 6.88 (d, 2H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 5.14 (d, 2H, J=2.0 Hz), 4.17 (t, 4H, J=6.5 Hz), 3.94 (t, 4H, J=6.5 Hz), 2.54-2.76 (m, 4H), 2.24-2.42 (m, 9H), 1.64-1.84 (m, 16H), 1.41-1.56 (m, 8H)

(Example 85) Synthesis of Polymerizable Compound (IIIq)

Step 1: Synthesis of Compound (3q)

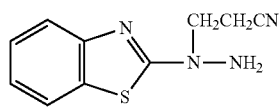

Compound (3q)

20.0 g (121.1 mmol) of 2-hydrazinobenzothiazole was dissolved in 400 ml of DMF under a nitrogen stream in a three-necked reactor equipped with a thermometer. To this solution were added 78.9 g (242.1 mmol) of cesium carbonate and 19.5 g (145.3 mmol) of 3-bromopropionitrile and the whole mass was stirred at 25° C. for 15 hours. After completion of the reaction, 1,500 ml of distilled water was added to the reaction solution and the mixture was extracted twice with 1,000 ml of ethyl acetate. After drying the organic layer over anhydrous sodium sulfate, sodium sulfate was filtered off. After concentrating the filtrate on a rotary evaporator, 200 ml of toluene was added to the concentrate and the mixture was cooled to 0° C. The precipitated crystals were collected by filtration and dried in vacuum to afford 11.2 g of compound (3q) as a white solid (yield: 42%).

The structure of the target product was identified by ¹H-NMR.

¹H-NMR (500 MHz, DMSO-d₆, TMS, δ ppm): 7.70 (dd, 1H, J=1.0 Hz, 8.0 Hz), 7.42 (dd, 1H, J=1.0 Hz, 8.0 Hz), 7.24 (dt, 1H, J=1.0 Hz, 7.5 Hz), 7.03 (dt, 1H, J=1.0 Hz, 7.5 Hz), 5.47 (s, 2H), 3.99 (t, 2H, J=6.5 Hz), 2.97 (t, 2H, J=6.5 Hz)

Step 2: Synthesis of Polymerizable Compound (IIIq)

The same operation as in Example 73 was performed except that in Step 2, 4.05 g (16.22 mmol) of compound (3a) synthesized in Example 37 was changed to 3.54 g (16.22 mmol) of compound (3q) synthesized in Step 1 above. As a result, 10.22 g of polymerizable compound (IIIq) was obtained (yield: 71.9%).

Polymerizable compound (IIIq)

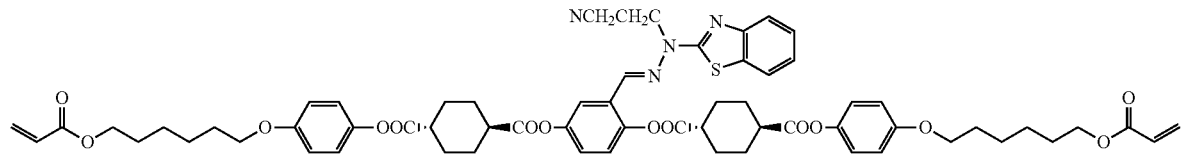

The structure of the target product was identified by ¹H-NMR.

¹H-NMR (500 MHz, CDCl₃, TMS, δ ppm): 7.84 (s, 1H), 7.66-7.76 (m, 3H), 7.38 (dt, 1H, J=1.0 Hz, 7.5 Hz), 7.22 (dt, 1H, J=1.0 Hz, 7.5 Hz), 7.13-7.16 (m, 2H), 6.99 (d, 2H, J=9.0 Hz), 6.98 (d, 2H, J=9.0 Hz), 6.88 (d, 2H, J=9.0 Hz), 6.87 (d, 2H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.62 (t, 2H, J=7.0 Hz), 4.17 (t, 4H, J=6.5 Hz), 3.94 (t, 2H, J=6.5 Hz), 3.94 (t, 4H, J=6.5 Hz), 2.85 (t, 2H, J=7.0 Hz), 2.70-2.80 (m, 1H), 2.54-2.70 (m, 3H), 2.25-2.41 (m, 8H), 1.64-1.85 (m, 16H), 1.41-1.55 (m, 8H)

(Example 86) Synthesis of Polymerizable Compound (IIIr)

Polymerizable compound (IIIr)

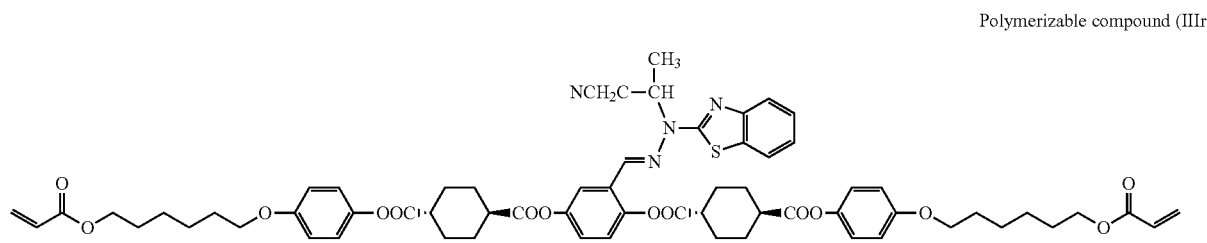

Step 1: Synthesis of Compound (3r)

Compound (3r)

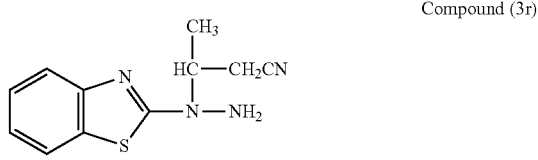

10.0 g (60.5 mmol) of 2-hydrazinobenzothiazole was dissolved in 200 ml of DMF under a nitrogen stream in a three-necked reactor equipped with a thermometer. To this solution were added 39.5 g (121 mmol) of cesium carbonate and 10.8 g (72.7 mmol) of 3-bromobutyronitrile and the whole mass was stirred at 25° C. for 15 hours. After completion of the reaction, 1,000 ml of distilled water was added to the reaction solution and the mixture was extracted twice with 500 ml of ethyl acetate. After drying the organic layer over anhydrous sodium sulfate, sodium sulfate was filtered off. After concentrating the filtrate on a rotary evaporator, the concentrate was purified by silica gel column chromatography (THF/toluene=1:9) to afford 10.2 g of compound (3r) as a white solid (yield: 72%).

The structure of the target product was identified by $^1$H-NMR.

$^1$H-NMR (500 MHz, DMSO-$d_6$, TMS, δ ppm): 7.70 (dd, 1H, J=1.0 Hz, 8.0 Hz), 7.42 (dd, 1H, J=1.0 Hz, 8.0 Hz), 7.24 (dt, 1H, J=1.0 Hz, 7.5 Hz), 7.03 (dt, 1H, J=1.0 Hz, 7.5 Hz), 5.47 (s, 2H), 3.99 (t, 2H, J=6.5 Hz), 2.97 (t, 2H, J=6.5 Hz)

Step 2: Synthesis of Polymerizable Compound (IIIr)

The same operation as in Example 73 was performed except that in Step 2, 4.05 g (16.22 mmol) of compound (3a) synthesized in Example 37 was changed to 3.77 g (16.22 mmol) of compound (3r) synthesized in Step 1 above. As a result, 9.47 g of polymerizable compound (IIIr) was obtained (yield: 65.8%).

The structure of the target product was identified by $^1$H-NMR.

$^1$H-NMR (500 MHz, CDCl$_3$, TMS, δ ppm): 8.18 (s, 1H), 7.65-7.76 (m, 3H), 7.37 (dt, 1H, J=1.0 Hz, 7.5 Hz), 7.21 (dt, 1H, J=1.0 Hz, 7.5 Hz), 7.13-7.16 (m, 2H), 6.98 (d, 2H, J=9.0 Hz), 6.98 (d, 2H, J=9.0 Hz), 6.88 (d, 2H, J=9.0 Hz), 6.88 (d, 2H, J=9.0 Hz), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.85-4.94 (m, 1H), 4.17 (t, 4H, J=6.5 Hz), 3.94 (t, 2H, J=6.5 Hz), 3.94 (t, 2H, J=6.5 Hz), 3.28-3.46 (m, 2H), 2.53-2.80 (m, 4H), 2.23-2.41 (m, 8H), 1.64-1.84 (m, 19H), 1.41-1.55 (m, 8H)

(Example 87) Synthesis of Polymerizable Compound (IIIs)

Step 1: Synthesis of Compound (3s)

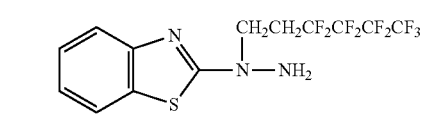

Compound (3s)

20.0 g (121 mmol) of 2-hydrazinobenzothiazole was dissolved in 300 ml of DMF under a nitrogen stream in a four-necked reactor equipped with a thermometer. To this solution were added 78.9 g (242 mmol) of cesium carbonate and 50.0 g (134 mmol) of 2-(nonafluorobutyl)ethyl iodide and the whole mass was stirred at 25° C. for 20 hours. After completion of the reaction, the reaction solution was added to 1,000 ml of water and the mixture was extracted with 1,000 ml of ethyl acetate. After drying the ethyl acetate layer over anhydrous sodium sulfate, sodium sulfate was filtered off. Ethyl acetate was distilled off under reduced pressure from the filtrate on a rotary evaporator to afford a brown solid. This brown solid was purified by silica gel column chromatography (n-hexane/ethyl acetate=9:1) to afford 11.5 g of compound (3s) as a white solid (yield: 22.9%).

The structure of the target product was identified by $^1$H-NMR.

$^1$H-NMR (500 MHz, CDCl$_3$, TMS, δ ppm): 7.63 (dd, 1H, J=1.0 Hz, 7.5 Hz), 7.57 (dd, 1H, J=1.0 Hz, 7.5 Hz), 7.32 (ddd, 1H, J=1.0 Hz, 7.5 Hz, 7.5 Hz), 7.11 (ddd, 1H, J=1.0 Hz, 7.5 Hz, 7.5 Hz), 4.35 (s, 2H), 4.08 (t, 2H, J=7.5 Hz), 2.56-2.70 (m, 2H)

Step 2: Synthesis of Polymerizable Compound (IIIs)

The same operation as in Example 73 was performed except that in Step 2, 4.05 g (16.22 mmol) of compound (3a) synthesized in Example 37 was changed to 6.67 g (16.22 mmol) of compound (3s) synthesized in Step 1 above. As a result, 10.34 g of polymerizable compound (IIIs) was obtained (yield: 62.2%).

The structure of the target product was identified by $^1$H-NMR.

$^1$H-NMR (500 MHz, CDCl$_3$, TMS, δ ppm): 7.74-7.78 (m, 2H), 7.69-7.73 (m, 2H), 7.38 (ddd, 1H, J=1.0 Hz, 7.5 Hz, 7.5 Hz), 7.21 (ddd, 1H, J=1.0 Hz, 7.5 Hz, 7.5 Hz), 7.11-7.17 (m, 2H), 6.95-7.01 (m, 4H), 6.85-6.91 (m, 4H), 6.40 (dd, 2H, J=1.5 Hz, 17.5 Hz), 6.13 (dd, 2H, J=10.0 Hz, 17.5 Hz), 5.82 (dd, 2H, J=1.5 Hz, 10.0 Hz), 4.61-4.69 (m, 2H), 4.18 (t, 4H, J=6.5 Hz), 3.95 (t, 4H, J=6.5 Hz), 2.52-2.71 (m, 6H), 2.25-2.40 (m, 8H), 1.61-1.84 (m, 16H), 1.41-1.55 (m, 8H)

Polymerizable compound (IIIs)

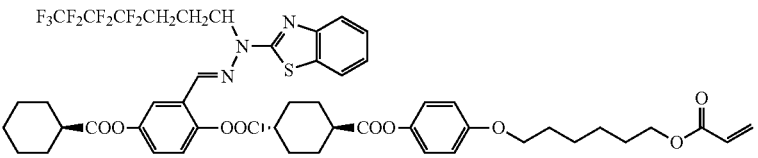

The invention claimed is:

1. A mixture comprising:
compound (I) having the following Formula (I):

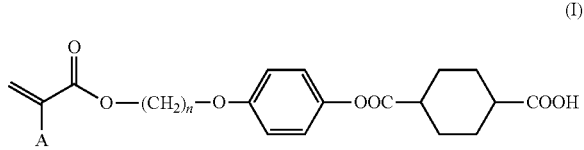

(I)

where A represents hydrogen, methyl group or chlorine, and n represents an integer of 1 to 20; and polymerizable compound (II) having the following Formula (II):

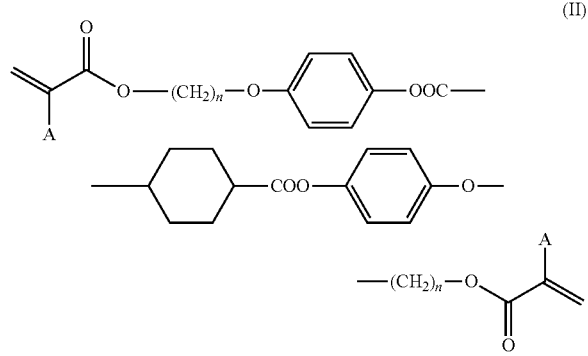

(II)

where A and n are as defined above wherein compound (I) accounts for 50 mol % or more of the entire mixture, and 1,4-cyclohexanedicarboxylic acid as an impurity accounts for less than 5 mol % of the entire mixture.

2. A method of producing a mixture of claim 1, comprising:

reacting in a water-immiscible organic solvent 1,4-cyclohexanedicarboxylic acid dichloride with compound (IV) having the following formula (IV):

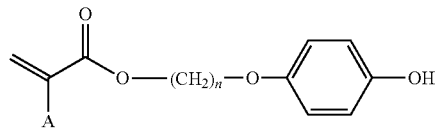

(IV)

where A represents hydrogen, methyl group or chlorine, and n represents an integer of 1 to 20 in the presence of a base to afford a reaction solution; and washing the reaction solution with a buffer solution having a pH of 5.0 to 6.0.

3. A method of producing a mixture of claim 1, comprising:

reacting in a water-immiscible organic solvent 1,4-cyclohexanedicarboxylic acid dichloride with compound (IV) having the following formula (IV):

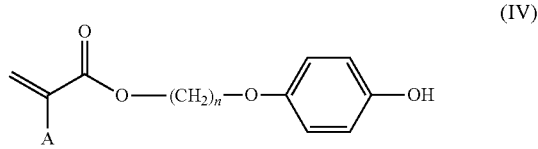

(IV)

where A represents hydrogen, methyl group or chlorine, and n represents an integer of 1 to 20 in the presence of a base to afford a reaction solution;

washing the reaction solution with water; and washing the reaction solution after washing with water with a buffer solution having a pH of 5.0 to 6.0.

4. The method of claim 2, wherein the buffer solution is a mixed buffer solution of acetic acid and sodium acetate, or a mixed buffer solution of potassium hydrogen phthalate and sodium hydroxide.

5. The method of claim 2, wherein the water-immiscible organic solvent is an organic solvent having a Hildebrand solubility parameter of 14.0 to 22.0 (MPa$^{1/2}$).

6. The method of claim 2, further comprising, after washing with the buffer solution, cooling an obtained organic layer to 5° C. or lower to precipitate polymerizable compound (II), and removing the precipitate.

* * * * *